United States Patent [19]
Bateson et al.

[11] Patent Number: 6,048,852
[45] Date of Patent: Apr. 11, 2000

[54] β-THIOPROPIONYL-AMINOACID DERIVATIVES AND THEIR USE AS β-LACTAMASE INHIBITORS

[75] Inventors: John Hargreaves Bateson, Reigate; David R Witty, Hertford; Brian Charles Gasson, Redhill; Desmond John Best, Little Hadham, all of United Kingdom; David John Payne, Collegeville, Pa.

[73] Assignee: SmithKline Beecham p.l.c., Brentford, United Kingdom

[21] Appl. No.: 09/125,245

[22] PCT Filed: Feb. 3, 1997

[86] PCT No.: PCT/EP97/00516

§ 371 Date: Jan. 13, 1999

§ 102(e) Date: Jan. 13, 1999

[87] PCT Pub. No.: WO97/30027

PCT Pub. Date: Aug. 21, 1997

[30] Foreign Application Priority Data

| Feb. 13, 1996 | [GB] | United Kingdom | 9602860 |
| May 24, 1996 | [GB] | United Kingdom | 9610907 |
| Sep. 13, 1996 | [GB] | United Kingdom | 961947 |

[51] Int. Cl.$^7$ ................................... A61K 31/195
[52] U.S. Cl. ................................... 514/210; 514/197
[58] Field of Search ..................... 514/197, 210

[56] References Cited

FOREIGN PATENT DOCUMENTS

WO/9533495  12/1995  WIPO .

OTHER PUBLICATIONS

Chemical Abstract. vol.: 120, No.:17, p. 1075, Abstract No.: 217613h, Apr. 25, 1994.

Ito, et al., "Synthesis and Pharmacological Activities of Novel Cyclic Disulfide and Cyclic Sulfide Derivatives as Hepatoprotective Agents," *Chem. Pharm. Bull.* 41(6): pp. 1066–1073 (1993).

Walker, et al., "Effect of Redox Environment on the in Vivo and in Vitro Folding of RTEM–1 β–Lactamase and *Escherichia coli* Alkaline Phosphatase," *The Journal of Biological Chemistry*, 269(45), pp. 28487–28493 (1994).

*Primary Examiner*—Robert Gerstl
*Attorney, Agent, or Firm*—James M. Kanagy; Charles M. Kinzig

[57] ABSTRACT

A method of treatment of bacterial infections in humans or animals which comprises administering, in combination with a β-lactam antibiotic, a therapeutically effective amount of an amino acid derivative of Formula (I) or a pharmaceutically acceptable salt, solvate or in vivo hydrolysable ester thereof,

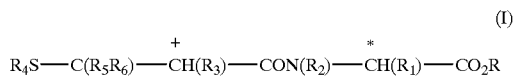

wherein:

R is hydrogen, a salt forming cation or an in vivo hydrolysable ester-forming group; $R_1$ is hydrogen, $(C_{1-6})$alkyl optionally substituted by up to three halogen atoms or by a mercapto, $(C_{1-6})$alkoxy, hydroxy, amino, nitro, carboxy, $(C_{1-6})$alkylcarbonyloxy, $(C_{1-6})$alkoxycarbonyl, formyl or $(C_{1-6})$alkylcarbonyl group, $(C_{3-7})$cycloalkyl, $(C_{3-7})$cycloalkyl$(C_{2-6})$alkyl, $(C_{2-6})$alkenyl, $(C_{2-6})$alkynyl, aryl, aryl$(C_{1-6})$alkyl, heterocyclyl or heterocyclyl$(C_{1-6})$alkyl; $R_2$ is hydrogen, $(C_{1-6})$alkyl or aryl$(C_{1-6})$alkyl; $R_3$ is hydrogen, $(C_{1-6})$alkyl optionally substituted by up to three halogen atoms, $(C_{3-7})$cycloalkyl, fused aryl$(C_{3-7})$cycloalkyl, $(C_{3-7})$cycloalkyl$(C_{2-6})$alkyl, $(C_{2-6})$alkenyl, $(C_{2-6})$alkynyl, aryl, aryl-$(CHR_{10})_m$—X—$(CHR_{11})_n$, heterocyclyl or heterocyclyl-$(CHR_{10})_m$—X—$(CHR_{11})_n$, where m is 0 to 3, n is 1 to 3, each $R_{10}$ and $R_{11}$ is independently hydrogen or $(C_{1-4})$alkyl and X is O, $S(O)_x$ where x is 0–2, or a bond; $R_4$ is hydrogen, or an in vivo hydrolysable acyl group; and $R_5$ and $R_6$ are independently hydrogen and $(C_{1-6})$alkyl or together represent $(CH_2)_p$ where p is 2 to 5. Some compounds are claimed per se.

23 Claims, No Drawings

β-THIOPROPIONYL-AMINOACID DERIVATIVES AND THEIR USE AS β-LACTAMASE INHIBITORS

This invention relates to chemical compounds having metallo-β-lactamase inhibitory and antibacterial properties. The invention also relates to methods for the preparation of such compounds, to pharmaceutical compositions containing them, and to uses thereof.

Metallo-β-lactamases confer resistance to the vast majority of β-lactam based therapies, including carbapenems and jeopardise the future use of all such agents. As a result of the increased use of carbapenems and other β-lactam antibiotics the clinical climate is becoming more favourable for the survival of clinical strains which produce metallo-β-lactamases, and metallo-β-lactamases have now been identified in common pathogens such as *Bacillus fragilis*, Klebsiella, *Pseudomonas aeruginosa* and *Serratia marcescens*. Emerging knowledge emphasises that metallo-β-lactamases have the potential to present a crisis situation for antimicrobial chemotherapy.

U.S. Pat. No. 4,513,009 discloses amino acid derivatives including thiorphan having enkephalinase-inhibiting, antalgic, antidiarrhea and hypotensive. Analgesic effects are disclosed for thiorphan (B. P. Roques et al, *Nature*, 1980, 288, 286) and for other mercapto amino acid derivatives (JO 3002-117-A). Mercapto amino acid derivatives are disclosed as inhibitors of angiotensin-converting enzyme (ACE) (J. L. Stanton, et al, *J. Med. Chem*, 1983, 26, 1257, U.S. Pat. No. 4,053,651 and GB 2090-591); as conferring antihypotensive effects (WO 9308162); as enkephalinase (neutral endopeptidase (NEP)) inhibitors (U.S. Pat. No. 4,474,799 and Mimura et al, *J. Med. Chem*., 1992, 35, 602 and references cited therein); as dual inhibitors of ACE and NEP (Fournie-Zaluski et al., *J. Med. Chem*., 1994, 37(8), 1070, WO 9417036); as inhibitors of endothelin-converting enzyme (ECE) (WO 9311154, Burtenshaw, et al, *Bioorg. Med. Chem. Lett*., 1993, 3(10), 1953 and Deprez et al., *Bioorg. Med. Chem. Lett*., 1996, 6(19), 2317); as metalloproteinase inhibitors (WO 9425435); and having radioprotective action and cytotoxicity (M. Hikita et al, *J. Radiat. Res*., 1975, 16(3), 162 and DE2,349,707). DE3819539 (Squibb) discloses amino acids and peptide derivatives as inhibitors of neutral endopeptidase and their use as antihypertensives and diuretics.

Other references to amino acid derivatives having the abovementioned activities include: Gordon et al., Life Sciences 1983, 33 (Supp. I), 113–6; Waller et al., J, Med. Chem. 1993, 36, 2390–2403; Saunders et al., J. Comp. Aided Mole. Des. 1987, 1, 133–42; Gomez-Monterrey et al., J. Med. Chem. 1993, 36, 87–94; Oya et al., Chem. Pharm. Bull. 1981, 29(4), 940–7; Trapani et al., Biochem. Mol. Biol. Int 1993, 31(5), 861–7; Baxter et al., J. Med. Chem. 1992, 35(20), 3718–20; Condon et al., J. Med. Chem. 1982, 25(3), 250–8; Cheung et al., J. Biol. Chem. 1980, 255(2), 401–7; Cushman et al., Biochemistry 1977, 16(25), 5484–91; EP0539848, EP0419327, EP0254032, EP0355784, EP0449523, EP0153755, U.S. Pat. No. 5,061,710, U.S. Pat. No. 4,339,600, U.S. Pat. No. 4,401,677, U.S. Pat. No. 4,199,512, DE2717548, DE2711225, JP54052073, JP54063017, JP54092937, JP55055165, JP54063017, W09407481, W08202890 and BE890398.

Other amino acid derivatives are described by: Fuchs et al., Arzneim.-Forsch. 1985, 35(9)1394–402, having mitochondrial dysfunction and postischemic myocardial damage activity; Rajkovic et al., Biochem. Pharmacol. 1984, 33(8), 1249–50, having enhancement of neutrophil response and modulation of superoxide and hydrogen peroxide production; Sakurai et al., Chem. Pharam. Bull. 1979, 27(12), 3022–8 forming a peptide/cytochrome P-450 heme system; and Sugiura et al., J. Am. Chem. Soc. 1977, 99(5), 1581–5, forming copper(II) and nickel(II) complexes.

According to the present invention there is provided a method of treatment of bacterial infections in humans or animals which comprises administering, in combination with a β-lactam antibiotic, a therapeutically effective amount of a compound of formula (I) or a pharmaceutically acceptable salt, solvate or in vivo hydrolysable ester thereof:

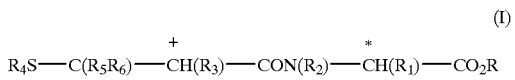

(I)

wherein:

R is hydrogen, a salt forming cation or an in vivo hydrolysable ester-forming group;

$R_1$ is hydrogen, $(C_{1-6})$alkyl optionally substituted by up to three halogen atoms or by a mercapto, $(C_{1-6})$alkoxy, hydroxy, amino, nitro, carboxy, $(C_{1-6})$alkylcarbonyloxy, $(C_{1-6})$alkoxycarbonyl, formyl or $(C_{1-6})$ alkylcarbonyl group, $(C_{3-7})$cycloalkyl, $(C_{3-7})$cycloalkyl$(C_{2-6})$alkyl, $(C_{2-6})$alkenyl, $(C_{2-6})$alkynyl, aryl$(C_{1-6})$alkyl, heterocyclyl or heterocyclyl$(C_{1-6})$alkyl;

$R_2$ is hydrogen, $(C_{1-6})$alkyl or aryl$(C_{1-6})$alkyl;

$R_3$ is hydrogen, $(C_{1-6})$alkyl optionally substituted by up to three halogen atoms, $(C_{3-7})$cycloalkyl, fused aryl$(C_{3-7})$cycloalkyl, $(C_{3-7})$cycloalkyl$(C_{2-6})$alkyl, $(C_{2-6})$alkenyl, $(C_{2-6})$alkynyl, aryl, aryl-$(CHR_{10})_m$—X—$(CHR_{11})_n$, heterocyclyl or heterocyclyt-$(CHR_{10})_m$—X—$(CHR_{11})_n$, where m is 0 to 3, n is 1 to 3, each $R_{10}$ and $R_{11}$ is independently hydrogen or $(C_{1-4})$alkyl and X is O, $S(O)_x$ where x is 0–2, or a bond;

$R_4$ is hydrogen, or an in vivo hydrolysable acyl group; and $R_5$ and $R_6$ are independently hydrogen and $(C_{1-6})$alkyl or together represent $(CH_2)_p$ where p is 2 to 5.

In one aspect X is O, S or a bond and $R_{10}$ and $R_{11}$ are each hydrogen.

The compound of formula (I) may exist in a number of isomeric forms, all of which, including racemic and diastereoisomeric forms, are encompassed within the scope of the present invention.

It is preferred that the stereochemistry at the carbon atom marked * is D-, particularly where $R_1$ is phenyl.

Although racemic and other mixtures of (*) D- and L-diastereomers of known compounds of formula (I) have been described, there has been little or no attempt to isolate pure D- isomers as herein defined because the antihypertensive activity of the compounds has been found to reside predominantly in the L-isomer.

The preferred stereochemistry at the carbon atom marked (+) is S.

Examples of $R_1$ optionally substituted alkyl include methyl, isobutyl, carboxymethyl, mercaptomethyl and 1-hydroxyethyl. Examples of $R_1$ arylalkyl include optionally substituted benzyl. Examples of $R_1$ aryl include phenyl optionally substituted with up to five, preferably up to three, groups selected from halogen, mercapto, $(C_{1-6})$ alkyl optionally substituted by 1-3 halo, phenyl, $(C_{1-6})$ alkoxy optionally substituted by 1-3 halo, hydroxy$(C_{1-6})$alkyl, mercapto$(C_{1-6})$alkyl, hydroxy, amino, nitro, carboxy, $(C_{1-6})$alkylcarbonyloxy, $(C_{1-6})$alkoxycarbonyl, formyl or $(C_{1-6})$alkylcarbonyl groups, preferably unsubstituted phenyl.

Examples of $R_1$ heteroaryl include indolyl, thienyl, isoimidazolyl, thiazolyl, furyl and benzothienyl, preferably 2-thienyl, 2-furyl or 2-benzothienyl. $R_1$ is most preferably unsubstituted phenyl.

Certain compounds of formula (I) including compounds where $R_1$ is aryl or heterocyclyl and $R_3$ is aryl-$(CHR_{10})_m$—X—$(CHR_{11})_n$, hereafter referred to as compounds of formula (IA), compounds where $R_5$ and $R_6$ are not hydrogen, hereafter referred to as compounds of formula (IB) and compounds of formula (I) where the stereochemistry at the carbon marked * is D-, hereafter referred to as compounds of formula (IC), are novel and as such form part of the invention.

Suitable examples of $R_2$ include hydrogen, methyl and benzyl.

$R_2$ is preferably hydrogen.

Examples of $R_3$ include methyl, isobutyl, phenyl-$(CH_2)_{1-5}$, phenoxyethyl, 1-indanyl, 3,4-dihydroxybenzyl, 4-hydroxycarbonyl-phenylethyl, 2-trifluoromethylquinolin-6-yl, 4-difluoromethoxy-phenylethyl and 3-methyl-2,4,5-tricarbonylimidazolidin-1-yl.

Preferably $R_3$ is aryl-$(CH_2)_m$—X—$(CH_2)_n$, most preferably benzyl, 2-phenethyl or 3-phenylpropyl. When X is $S(O)_x$, x is preferably 0.

$R_4$ is preferably hydrogen.

$R_5$ and $R_6$ are preferably independently hydrogen or methyl.

Suitable pharmaceutically acceptable salts of the carboxylic acid group of the compound of formula (I) (or of other carboxylic acid groups which may be present as optional substituents) include those in which R is a metal ion e.g. aluminium salts, alkali metal salts (e.g. sodium, lithium or potassium salts), alkaline earth metal salts (e.g. calcium or magnesium salts), ammonium salts, and substituted ammonium salts, for example those with lower alkylamines (e.g.triethylamine), hydroxy-lower alkylamines (e.g. 2-hydroxyethylamine), bis-(2-hydroxyethyl)amine, tris-(2-hydroxyethyl) amine, lower-cycloalkylamines (e.g. dicyclohexyl-amine), or with procaine, dibenzylarnine, N,N-dibenzyl-ethylenediamine, 1-ephenamine, N-methylmorpholine, N-ethylpiperidine, N-benzyl-β-phenethylamine, dehydroabietylamine, ethylenediamine, N,N-bishydroabietylethylenediamine, bases of the pyridine type (e.g. pyridine, collidine and quinoline), and other amines which have been or can be used to form quaternary ammonium salts.

Pharmaceutically acceptable salts may also be acid addition salts of any amino or substituted amino group(s) that may be present as optional substituents on the compound of formula (I), or of a heterocyclic group ring nitrogen atom. Suitable salts include for example hydrochlorides, sulphates, hydrogen sulphates, acetates, phosphates etc. and other pharmaceutically acceptable salts will be apparent to those skilled in the art. Suitable addition salts are the hydrochlorides and hydrogen sulphates.

Preferred salts are sodium salts.

Examples of suitable pharmaceutically acceptable in vivo hydrolysable ester-forming groups R include those forming esters which break down readily in the human body to leave the parent acid or its salt. Suitable groups of this type include those of part formulae (i), (ii), (iii), (iv) and (v):

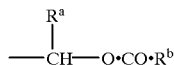

(i)

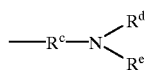

(ii)

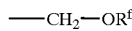

(iii)

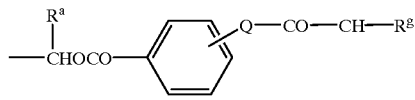

(iv)

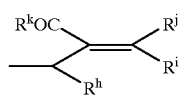

(v)

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl)amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^i$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester-forming groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl, α-ethoxycarbonyloxyethyl and propoxycarbonyloxyethyl; dialkylaminoalkyl especially di-loweralkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl)but-2-enyl; and lactone groups such as phthalidyl and dimethoxyphthalidyl.

A further suitable pharmaceutically acceptable in vivo hydrolysable ester-forming group is that of the formula:

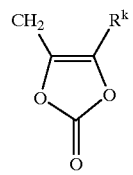

wherein $R^k$ is hydrogen, $C_{1-6}$ alkyl or phenyl.

R is preferably hydrogen.

When used herein the term 'aryl' includes phenyl and naphthyl, each optionally substituted with up to five, preferably up to three, groups selected from halogen, mercapto, ($C_{1-6}$) alkyl optionally substituted by 1-3 halo, phenyl, ($C_{1-6}$) alkoxy optionally substituted by 1-3 halo, hydroxy($C_{1-6}$)alkyl, mercapto($C_{1-6}$)alkyl, hydroxy, amino, nitro, carboxy, ($C_{1-6}$) alkylcarbonyloxy, alkoxycarbonyl, formyl, or ($C_{1-6}$) alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, ($C_{1-6}$)alkyl, ($C_{1-6}$) alkoxy, $CF_3$, halo($C_{1-6}$)alkyl, hydroxy, carboxy, carboxy salts, carboxy esters such as ($C_{1-6}$)alkoxycarbonyl, ($C_{1-6}$) alkoxycarbonyl($C_{1-6}$)alkyl, aryl, and oxo groups. Each heterocyclic ring suitably has from 4 to 7, preferably 5 or 6, ring atoms. The term 'heteroaryl' refers to heteroaromatic heterocyclic ring or ring system, suitably having 5 or 6 ring atoms in each ring. A fused heterocyclic ring system may include carbocyclic rings and need include only one heterocyclic ring. Examples of heterocyclyl groups include indolyl, thienyl, isoimidazolyl, thiazolyl, furyl, quinolinyl, imidazolidinyl and benzothienyl. Compounds within the invention containing a heterocyclyl group may occur in two or more tautomeric forms depending on the nature of the heterocyclyl group; all such tautomeric forms are included within the scope of the invention.

When used herein the terms 'lower alkyl', 'lower alkenyl', 'lower alkynyl' and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

It will be appreciated that also included within the scope of the invention are pharmaceutically acceptable salts and pharmaceutically acceptable esters, including in vivo hydrolysable esters, of any carboxy groups that may be present as optional substituents in compounds of formula (I).

Some compounds of formula (I), (IA), (IB) and (IC) may be crystallised or recrystallised from solvents such as organic solvents. In such cases solvates may be formed. This invention includes within its scope stoichiometric solvates including hydrates as well as compounds containing variable amounts of solvents such as water that may be produced by processes such as lyophilisation. Compounds of formula (I), (IA), (IB) and (IC) may be prepared in crystalline form by for example dissolution of the compound in water, preferably in the minimum quantity thereof, followed by admixing of this aqueous solution with a water miscible organic solvent such as a lower aliphatic ketone such as a di-($C_{1-6}$) alkyl ketone, or a ($C_{1-6}$) alcohol, such as acetone or ethanol.

The compounds of formulae (I), (IA), (IB) and (IC) are metallo-β-lactarnase inhibitors and are intended for use in pharmaceutical compositions. Therefore it will readily be understood that they are preferably each provided in substantially pure form, for example at least 60% pure, more suitably at least 75% pure and preferably at least 85% pure, especially at least 95% pure particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I), (IA), (IB) or (IC) or salt, solvate or in vivo hydrolysable ester thereof.

Compounds of formula (I) may generally be prepared by processes analogous to those described in the prior art references listed above.

The present invention also provides a process for the preparation of a compound of formula (IA), (IB) or (IC) as defined above, which comprises reacting a compound of formula (II)

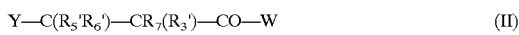

$$Y\text{—}C(R_5{'}R_6{'})\text{—}CR_7(R_3{'})\text{—}CO\text{—}W \qquad (II)$$

with a compound of formula (III)

$$X^1\text{—}CH(R_1{'})\text{—}CO_2R^x \qquad (III)$$

wherein W is a leaving group, Y is Y' where Y' is $R_4{'}S$ or a group convertible hereto and $R_7$ is H, or Y and $R_7$ together form a bond, $R^x$ is R or a carboxylate protecting group, $X^1$ is $N_3$ or $NHR_2{'}$ and $R_1{'}$, $R_2{'}$, $R_3{'}$, $R_4{'}$, $R_5{'}$ and $R_6{'}$ are $R_1$, $R_2$, $R_3$, $R_4$, $R_5$ and $R_6$ or groups convertible thereto, wherein R, $R_1$, $R_2$, $R_3$, $R_4$, $R_5$ and $R_6$ are as defined in formula (IA), (IB) or (IC), and thereafter, where Y and $R_7$ form a bond, reacting the product with a nucleophilic sulphur reagent Y'H, where necessary, converting Y' into $R_4{'}S$, $R^x$, $R_1{'}$, $R_2{'}$, $R_3{'}$ $R_4{'}$, $R_5{'}$ and/or $R_6{'}$ into R, $R_1$, $R_2$, $R_3$, $R_4$, $R_5$ and/or $R_6$ and optionally inter-converting R, $R_1$, $R_2$, $R_3$, $R_4$, $R_5$ and/or $R_6$.

Suitable ester-forming carboxyl-protecting groups $R^x$ other than in vivo hydrolysable ester forming groups are those which may be removed under conventional conditions. Such groups for $R^x$ include methyl, ethyl, benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl (such as trimethylsilyl), stannyl or phosphorus- containing group or an oxime radical of formula —N=$CHR^7$ where $R^7$ is aryl or heterocyclyl, or an in vivo hydrolysable ester radical such as defined below.

Certain compounds of formulae (II) and (III) may include an amino group which may be protected. Suitable amino protecting groups are those well known in the art which may be removed under conventional conditions if required without disruption of the remainder of the molecule.

Examples of amino protecting groups include ($C_{1-6}$) alkanoyl; benzoyl; benzyl optionally substituted in the phenyl ring by one or two substituents selected from ($C_{1-4}$) alkyl, ($C_{1-4}$) alkoxy, trifluoromethyl, halogen, or nitro; ($C_{1-4}$) alkoxycarbonyl; benzyloxycarbonyl or trityl substituted as for benzyl above; allyloxycarbonyl, trichloroethoxycarbonyl or chloroacetyl.

When $X^1$ in the compound of formula (III) is $NHR_2{'}$, the compound is preferably presented as the anion prepared by treatment of the amine with an organic base such as triethylamine, pyridine or morpholine, and suitable examples of the leaving W group in the compound of formula (II) include halo such as chloro and mixed sulphonic anhydrides such as those where W is methanesulphonyloxy, toluene-p-sulphonyloxy or trifluoromethanesulphonyloxv in mixed sulphonic anhydrides. The compound of formula (III) may be presented as the trimethylsilyl ester hydrochloride.

The reaction of the compounds of formula (II) and (III) is preferably carried out at ambient temperature, for example 15–25° C., in an inert solvent such as chloroform tetrahydrofuran, dichloromethane, dioxan or dimethylformamide.

When X in the compound of formula (III) is $N_3$, the leaving group W in the compound of formula (II) is preferably SH and the reaction is carried out at elevated temperature, such as at reflux, in an inert solvent such as toluene.

Examples of Y' convertible into $R_4'S$ include halo such as bromo which may be displaced by thiobenzoic acid or thioacteic acid.

Where $R_7$ and Y together represent a bond, the group $R_4'S$ may be introduced by addition of a nucleophilic sulphur reagent Y'H. Y' is $R_4'S$ or a group convertible thereto. Thiolacetic acid is a suitable sulphur reagent.

Examples of groups $R_1'$, $R_2'$, $R_3'$, $R_4'$ convertible to $R_1$, $R_2$. $R_3$ and $R_4$ include those where any carboxy or amino group is protected by carboxy or amino protecting groups.

$R_4'$ in the compound of formula (II) is preferably other than hydrogen, for example acetyl.

The acid derivative of formula (II) is preferably prepared from the corresponding free acid by treatment with strong base such as sodium hydride followed by a source of the anion leaving group W, such as oxalyl chloride where W is Cl, or hydrogen sulphide where W is SH.

The initial product of the reaction of compounds of formulae (II) and (III) is a compound of formula (IV):

$$Y\text{---}C(R_5'R_6')\text{---}CR_7(R_3')\text{---}CON(R_2')\text{---}CH(R_1')\text{---}CO_2R^x \quad (IV)$$

wherein the variables are as defined in formulae (II) and (III). Novel intermediates of formula (IV) wherein $R^x$ is other than R when $R_1'$, $R_2'$, $R_3$, $R_4'$, $R_5'$ and $R_6'$ are $R_1$, $R_2$, $R_3$, $R_4$, $R_5$ and $R_6$ also form part of the invention. In one aspect Y is $R_4'S$ and $R_7$ is H.

When $R^x$ is other than hydrogen, the carboxy group —$COOR^x$ may be deprotected, that is to say, converted to a free carboxy, carboxy salt or carboxy ester group —COOR in a conventional manner, for example as described in EP0232966A.

Simultaneous deprotection of —$COOR^x$ and $R_4'S$ may be achieved by treatment with sodium sulphide nonahydrate in water/methanol.

When it is desired to obtain a free acid or salt of the preferred isomer of the formula (I) from an isomeric mixture, this may be effected by chromatographic separation of the diastereomers of the product. Where this is an ester and/or where $R_4'$ is other than hydrogen, the desired isomer may then be deprotected to-give the corresponding free acid or salt. In some cases, however, it has been found particularly convenient first to deprotect the isomeric mixture to give an isomeric mixture of the free acid or salt of formula (I), followed by fractional recrystallisation to give the desired acid or salt isomer. Where *D isomer of formula (I) is desired, it is preferred to use the corresponding *D isomer of the intermediate of formula (III).

When an enatiomerically pure form of (III) is used in the preparation of (I), the preferred diastereomer at position (+) of (I) can also be separated by chromatography. An enantiomerically pure form of (II) may also be used.

A carboxyl group may be regenerated from any of the above esters by usual methods appropriate to the particular $R^x$ group, for example, acid- and base-catalysed hydrolysis, or by enzymically-catalysed hydrolysis, or by hydrogenolysis under conditions wherein the remainder of the molecule is substantially unaffected. For example, in the case of acetonyl, by hydrolysis in acetonitrile with 0.1M aqueous potassium hydroxide solution.

Pharmaceutically acceptable salts may be prepared from such acids by treatment with a base, after a conventional work-up if necessary. Suitable bases include sodium hydrogen carbonate to form sodium salts.

Crystalline forms of the compounds of formula (I) where R is a salt forming cation may for example be prepared by dissolving the compound (I) in the minimum quantity of water, suitably at ambient temperature, then adding a water miscible organic solvent such as a ($C_{1-6}$) alcohol or ketone such as ethanol or acetone, upon which crystahisation occurs and which may be encouraged for example by cooling or trituration.

Compounds of formulae (II) and (III) are known compounds or may be prepared by procedures analogous to those described in the prior art references listed above.

$R_5'/R_6'$ substituted compounds of formula (II) where Y is Y' and $R_7$ is H may generally be prepared from an acrylic, crotonic, β-substituted acrylic, or β, β-disubstituted acrylic acid or ester of formula (V):

(V)

in which Z is H or a hydrolysable ester forming group and the remaining variables are as previously defined, by addition of a nucleophilic sulphur reagent Y'H. Thiolacetic acid is a suitable sulphur reagent. Subsequent conversion of the carboxylate group $CO_2Z$ to a reactive acid derivative COW, provides the compound of structure (II).

Compounds of formula (II) where Y and $R_7$ are a bond may be obtained from compounds of formula (V) by conversion of the acid group to a leaving group COW.

Compounds of formula (V) are prepared conventionally, for example, by the reaction of a carbonyl compound $R_5'COR_6'$ with a phosphorane $R_3'C(PPh_3)CO_2Z$.

Novel compounds of formula (III), which are cc-amino acids, may be prepared by any conventional amino acid synthesis, for example from the corresponding α-keto ester $R_1'$—CO—$CO_2R^x$ via the oxime ester $R_1'$—C(=N—OH)—$CO_2R^x$ by conventional routes. The α-keto ester is obtainable from the $R_1'$—H, $R_1'$—$CH_2CO_2R^x$ or $R_1'$—$CO_2R^x$ by routine methods (J. March, vide infra). Alternatively the compounds of formula (III) may be prepared from the aldehyde intermediate $R_1'$—CHO by the Strecker synthesis [cf. Advanced Organic Chemistry; Mechanism and Structure, 4th Edn, by J. March, Section 6-50, p.965; 1992, John Wiley and Sons Inc, ISBN 0-471-60180-21].

A compound of formula (I), (IA), (IB) or (IC) or a salt, solvate or in vivo hydrolysable ester thereof, may be administered in the form of a pharmaceutical composition together with or a pharmaceutically acceptable carrier. The compounds of formula (I) have metallo-β-lactamase inhibitory properties, and are useful for the treatment of infections in animals, especially mammals, including humans, in particular in humans and domesticated (including farm)animals. The compounds may be used, for example, for the treatment of infections of, inter alia, the respiratory tract, the urinary tract, and soft tissues and blood, especially in humans.

The compounds may be used in combination with an antibiotic partner for the treatment of infections caused by metallo-β-lactamase producing strains, in addition to those infections which are subsumed within the antibacterial spectrum of the antibiotic partner. Metallo-β-lactamase producing strains include:- *Pseudomonas aeruginosa, Klebsiella pneumoniae, Xanthomonas maltophilia, Bacteroides fragilis, Serratia marcescens, Bacteroides distasonis, Pseudomonas cepacia, Aeronomas hydrophila, Aeromonas sobria, Aeromonas salmonicida, Bacillus cereus, Legionella gormanii* and Flavobacterium spp.

It is generally advantageous to use a compound according to the invention in admixture or conjunction with a carbapenem, penicillin, cephalosporin or other β-lactam antibiotic and that can result in a synergistic effect, because of the metallo-β-lactamase inhibitory properties of the compounds according to the invention. In such cases, the compound of formula (I), (IA), (IB) or (IC) and the β-lactam antibiotic can be administered separately or in the form of a single composition containing both active ingredients as discussed in more detail below. The compositions of the invention include those in a form adapted for oral, topical or parenteral use and may be used for the treatment of bacterial infection in mammals including humans. The compounds of formula (I), (IA), (IB) and (IC) are particularly suitable for parenteral administration.

The compounds of formula (I), (IA), (IB) or (IC) may be formulated for administration in any convenient way for use in human or veterinary medicine, by analogy with other antibiotics and other β-lactam antibiotic/β-lactamase inhibitor combinations.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I), (IA), (IB) or (IC) or a pharmaceutically acceptable salt thereof is administered in the above-mentioned dosage range.

A composition according to the invention may comprise a compound of formula (I), (IA), (IB) or (IC) or a salt, solvate or in vivo hydrolysable ester thereof together with one or more additional active ingredients or therapeutic agents, for example a β-lactam antibiotic such as a carbapenem, penicillin or cephalosporin or pro-drug thereof. Carbapenems, penicillins, cephalosporins and other β-lactam antibiotics suitable for co-administration with the compound of formula (I), (IA), (IB) or (IC)—whether by separate administration or by inclusion in the compositions according to the invention—include both those known to show instabilityto or to be otherwise susceptible to metallo-β-lactamases and also those known to have a degree of resistance to metallo-β-lactamases.

A serine β-lactamase inhibitor such as clavulanic acid, sulbactam or tazobactam may also be co-administered with the compound of the invention and the β-lactam antibiotic, either by separate administration, or co-formulation with one, other or both of the compounds of the invention and the β-lactam antibiotic.

Examples of carbapenems that may be co-administered with the compounds according to the invention include imipenem, meropenem, biapenem, BMS181139 ([4R-[4alpha,5beta,6beta(R*)]]-4-[2-[(aminoiminomethyl) amino]ethyl]-3-[(2-cyanoethyl)thio]-6-(1-hydroxyethyl)-7-oxo-1-azabicyclo[3.2.0]hept-2-ene-2-carboxylic acid), BO2727 ([4R-3[3S*,5S *(R*)], 4alpha,5beta,6beta(R*)]]-6-(1-hydroxyethyl)-3-[[5-[1-hydroxy-3-(methylamino) propyl]-3-pyrrolidinyl]thio]-4-methyl-7-oxo-1-azabicyclo [3.2.0]hept-2-ene-2-carboxylic acid monohydrochloride), ER35786 ((1R, 5S, 6S)-6-[1(R)-Hydroxymethyl]-2-[2(S)-[1 (R)-hydroxy-1-[pyrrolidin-3(R)-yl]methyl]pyrrolidin-4(S)-ylsulfanyl]-1-methyl-1-carba-2-penem-3-carboxylic acid hydrochloride) and S4661 ((1R,5S,6S)-2-[(3S,5S)-5-(sulfamoylaminomethyl) pyrrolidin-3-yl]thio-6-[(1R)-1-hydroxyethyl]-1-methylcarbapen-2-em-3-carboxylic acid).

Examples of penicillins suitable for co-administration with the compounds according to the invention include benzylpenicillin, phenoxymethylpenicillin, carbenicillin, azidocillin, propicillin, ampicillin, amoxyciuin, epicillin, ticarcillin, cyclacillin, pirbenicillin, azlocillin, meziocillin, sulbenicillin, piperacillin, and other known penicillins. The penicillins may be used in the form of pro-drugs thereof, for example as in vivo hydrolysable esters,for example the acetoxymethyl, pivaloyloxymethyl, α-ethoxycarbonyloxyethyl and phthalidyl esters of ampicillin, benzylpenicillin and amoxycillin; as aldehyde or ketone adducts of penicillins containing a 6-α-aminoacetamido side chain (for example hetacillin, metampicillin and analogous derivatives of amoxycillin); and as α-esters of carbenicillin and ticarcillin, for example the phenyl and indanyl α-esters.

Examples of cephalosporins that may be co-administered with the compounds according to the invention include, cefatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftazidime, cefuroxime, cefmetazole, cefotaxime, ceftriaxone, and other known cephalosporins, all of which may be used in the form of pro-drugs thereof.

Examples of ,-lactam antibiotics other than penicillins and cephalosporins that may be co-administered with the compounds according to the invention include aztreonam, latamoxef (Moxalactam—Trade Mark), and other known β-lactam antibiotics, all of which may be used in the form of pro-drugs thereof.

Particularly suitable penicillins for co-administration with the compounds according to the invention include ampicillin, amoxycillin, carbenicillin, piperacillin, azlocillin, mezlocillin, and ticarcillin. Such penicillins may be used in the form of their pharmaceutically acceptable salts, for example their sodium salts. Alternatively, ampicillin or amoxycillin may be used in the form of fine particles of the zwitterionic form (generally as ampicillin trihydrate or amoxycillin trihydrate) for use in an injectable or infusable suspension, for example, in the manner hereinbefore described in relation to the compounds according to the invention. Amoxycillin, for example in the form of its sodium salt or the trihydrate, is particularly preferred for use in synergistic compositions according to the invention.

Particularly suitable cephalosporins for co-administration with the compounds according to the invention include cefotaxime and ceftazidime, which may be used in the form of their pharmaceutically acceptable salts, for example their sodium salts.

A compound of formula (I), (IA), (IB) or (IC) may be administered to the patient in conjunction with a β-lactam antibiotic such as a carbapenem, penicillin or cephalosporin in a synergistically effective amount.

The compounds of formula (I), (IA), (IB) or (IC) may suitably be administered to the patient at a daily dosage of from 0.7 to 50 mg/kg of body weight. For an adult human (of approximately 70 kg body weight), from 50 to 3000 mg, preferably from 100 to 1000 mg, of a compound according to the invention may be administered daily, suitably in from 1 to 6, preferably from 2 to 4, separate doses. Higher or lower dosages may, however, be used in accordance with clinical practice.

When the compositions according to the invention are presented in unit dosage form, each unit dose may suitably comprise from 25 to 1000 mg, preferably from 50 to 500 mg, of a compound according to the invention. Each unit dose may, for example, be 62.5, 100, 125, 150, 200 or 250 mg of a compound according to the invention.

When the compounds of formula (I), (IA), (IB) or (IC) are co-administered with a penicillin, cephalosporin, carbapenem or other β-lactam antibiotic, the ratio of the amount of the compound according to the invention to the amount of the other β-lactam antibiotic may vary within a wide range. The said ratio may, for example, be from 100:1 to 1:100; more particularly, it may, for example, be from 2:1 to 1:30.

The amount of carbapenem, penicillin, cephalosporin or other β-lactam antibiotic in a synergistic composition according to the invention will normally be approximately similar to the amount in which it is conventionally used per se, for example from about 50 mg, advantageously from about 62.5 mg, to about 3000 mg per unit dose, more usually about 125, 250, 501) or 1000 mg per unit dose.

The present invention further provides a compound of formula (I) or a pharmaceutically acceptable salt, solvate or in vivo hydrolysable ester thereof, and in particular a compound of formula (IA), (IB) or (IC), for use in the treatment of bacterial infections.

The present invention also includes the use of a compound of formula (I) or a pharmaceutically acceptable salt, solvate or in vivo hydrolysable ester thereof, in the manufacture of a medicament for the treatment of bacterial infections The present invention also includes the use of a compound of formula (I) or a pharmaceutically acceptable salt, solvate or in vivo hydrolysable ester thereof as a metallo-β-lactamase inhibitor.

In a further aspect, the invention provides a method of treatment of bacterial infections in humans or animals which comprises administering, in combination with a carbapenem antibiotic, a therapeutically effective amount of a metallo-β-lactamase inhibitor.

A further composition according to the invention comprises a metallo-β-lactamase inhibitor together with a carbapenem antibiotic and a pharmaceutically acceptable carrier.

Such method and composition may be administered as described above for uses of compounds of formula (I).

All the above compositions and methods may optionally include a serine β-lactamase inhibitor as above described.

The compounds of the present invention are active against metallo-β-lactamase enzymes produced by a wide range of organisms including both Gram-negative organisms and Gram-positive organisms.

The following Examples illustrate compounds useful in the present invention, and intermediates in their preparation. (All temperatures are in ° C).

EXAMPLES

Example 1

N-[2'-Benzyl-3'-mercaptopropionyl]phenylalanine
a) N-[S-Acetyl-2'-benzyl-3'-mercaptopropionyl]phenylalanine methyl ester
Prepared by Method B of Example 19 but using a 1:1 mixture of D and L-phenylalanine methyl ester hydrochlorides (238 mg, 1.0 mmol, Aldrich) and 2-acetylthiomethyl-3-phenylpropanoic acid [EP 0361365] (113 mg, 0.5 mmol). The title compound was obtained in 77% yield as a semi-crystalline mass, an approximately equimolar mixture of diastereoisomers. These were partially separated.

Less polar: $\delta_H$ (CDCl$_3$) 2.34 (3H, s, MeCOS), 2.58 (1H, m, CH$_2$C$\underline{H}$CH$_2$), 2.75–3.15 (6H, m, C$\underline{H}_2$CHCH$_2$, C$\underline{H}_2$Ar), 3.61 (3H, MeO), 4.74 (1H, app.dq HCN), 5.77 (1H, bd, NH), 7.05–7.30 (10H, m, Ar-H).

More polar: $\delta_H$ (CDCl$_3$) 2.32 (3H, s, MeCOS), 2.56 (1H, m, CH$_2$C$\underline{H}$CH$_2$), 2.68–3.13 (6H, m, C$\underline{H}_2$CHC$\underline{H}_2$, C$\underline{H}_2$Ar), 3.66 (3H, MeO), 4.85 (1H, app.dq HCN), 5.81 (1H, bd, NH), 6.60 (2H, dd, Ar-H) 7.05–7.35 (8H, m, Ar-H).

b) N-[2'-Benzyl-3'-mercaptopropionyl]-phenylalanine

Prepared by Method C of Example 19 but using N-(S-acetyl-2'-benzyl-3'-mercaptopropionyl)-phenylalanine methyl ester (60 mg, 0.15 mmol). The title compound was obtained as a clear oil, an approximately equimolar mixture of diastereomers.

$\delta_H$ (CDCl$_3$) 2.45–2.60 (1H, m, CH$_2$CHCH$_2$), 2.75–3.28 (6H, m, CH$_2$CH$_2$CHCH$_2$, CH$_2$Ar), 4.83–4.93 (1H, m, HCN), 5.86 (1H, bd, NH), 6.75 (1H, dd, Ar-H), 7.10–7.30 (9H, m, Ar-H); m/z (ESI) 344 (M+H$^+$, 100%).

Example 2

N-[2'-Benzyl-3'-mercaptopropionyl]leucine a) D-Leucine methyl ester hydrochloride Prepared by Method A of Example 19 but using D-Leucine (1.0 g, 7.6 mmol, Aldrich). The title compound was formed as a white foam in quantitative yield.

$\delta_H$ (CD$_3$OD) 1.0, 1.02 (6H, 2d, (CH$_3$)$_2$CH), 1.6–1.9 (3H, m, Me$_2$CHCH$_2$), 7.90 (3H, m, MeO), 4.12 (1H, app.t, HCN).

b) N-[S-Acetyl-2'-benzyl-3'-mercaptopropionyl]leucine methyl ester Prepared by Method B of Example 19 but on a 1:1 mixture of D and L-leucine methyl ester hydrochlorides (113 mg, 0.5 mmol, L isomer from Aldrich) and using S-acetyl-2-benzyl-3-mercaptopropionic acid (0.5 mmol). This gave the title compound as a clear oil in 81% yield, an approximately equimolar mixture of diastereoisomers. These were partially separated.

Less polar: $\delta_H$ (CDCl$_3$) 0.91, 0.93 (6H, 2d, (CH$_3$)$_2$CH), 1.40–1.65 (3H, m, Me$_2$CHCH—$_2$), 2.32 (3H, s, MeCOS), 2.63 (1H, m, CH$_2$CHCH$_2$), 2.78–3.08 (4H, m, CH$_2$CHCH$_2$), 3.62 (3H, MeO), 4.53 (1H, app.dq HCN), 5.70 (1H, bd, NH), 7.10–7.25 (5H, m, Ar-H).

More polar: $\delta_H$ (CDCl$_3$) 0.75, 0.77 (6H, 2d, (CH$_3$)$_2$CH), 0.80–1.40 (3H, m, Me$_2$CHCH$_2$), 2.32 (3H, s, MeCOS), 2.62 (1H, m, CH$_2$CHCH$_2$), 2.88, 3.10 (4H, 2bd, CH$_2$CHCH$_2$), 3.65 (3H, MeO), 4.48 (1H, app.dq HCN), 5.61 (1H, bd, NH), 7.10–7.28 (5H, m, Ar-H).

c) N-[2'-Benzyl-3'-mercaptopropionyl]leucine

Prepared by Method C of Example 19 but on N-(S-acetyl-2'-benzyl-3'-mercaptopropionyl)-leucine methyl ester (60 mg, 0.20 mmol) in a 4:1 mixture of methanol: water over four hours. The product was subjected to silica gel flash chromatography eluting with formic acid-methyl formate-hexane to give the title compound as an approximately equimolar mixture of diastereoisomers in 75% yield.

$\delta_H$ (CDCl$_3$) 0.75, 0.78, 0.88, 0.91 (6H, 4d, (CH$_3$)$_2$CH), 0.90–1.80 (3H, m, Me$_2$CHCH$_2$), 2.47–2.65 (1H, m, CH$_2$CHCH$_2$), 2.75–3.00 (4H, m CH$_2$CHCH$_2$), 4.40–4.53 (1H, m, HCN), 5.84, 5.95 (1H, 2d, NH), 6.3 (2H, bs, SH, CO$_2$H), 7.05–7.30 (5H, m, Ar-H).

Example 3

N-[2'-Benzyl-3'-mercaptopropionyl]alanine a) D-Alanine methyl ester hydrochloride Prepared by Method A of Example 19 but utilising D-alanine (Aldrich) as the amino acid. This gave the title compound as a white crystaline solid in quantitative yield.

b) N-[S-Acetyl-2'-benzyl-3'-mereaptopropionyl]alanine methyl ester

Prepared by Method B of Example 19 but using S-acetyl-2-benzyl-3-mercaptopropionic acid (150 mg, 0.63 mmol) and a 1:1 mixture of D and L-alanine methyl ester hydrochlorides (100 mg, 0.7 mmol L-isomer from Aldrich). This gave the title compound as an approximately equimolar mixture of diastereoisomers in 82% yield as a clear oil.

$\delta_H$ (CDCl$_3$) 1.09, 1.33, (3H, 2d, CHCHN), 1.95, 1.94 (3H, 2s, MeO), 2.53–2.66 (1H, m, CH$_2$CHCH$_2$), 2.78–3.11 (4H, m, CH$_2$CHCH$_2$), 3.67, 3.70 (3H, 2s, MeO), 4.40–4.53 (1H, m, HCN), 5.78, 5.92 (1H, 2bd, NH), 7.15–7.30 (5H, Ar-H).

c) N-[2'-Benzyl-3'-mercaptopropionyl]alanine

Prepared by Method A of Example 19 but using N-(S-acetyl-2'-benzyl-3'-mercaptopropionyl)alanine methyl ester. The title compound was obtained as a clear oil, an approximately equimolar mixture of diastereoisomers.

$\delta_H$ (CDCl$_3$) 1.10, 1.35 (3H, 4d, (CH$_3$CHN), 2.49–2.66 (1H, m, CH$_2$CHCH$_2$), 2.79–3.08 (4H, m, CH$_2$CHCH$_2$), 4.41–4.52 (1H, m, HCN), 5.85, 5.93 (1H, 2d, NH), 6.5 (2H, bs, SH, CO$_2$H), 7.05–7.30 (5H, m, Ar-H); m/z (CI+) 268 (M+H$^+$ 100%), 286 M+NH$_4^+$ 85%).

Example 4

N-[2'-Benzyl-3'-mercaptopropionyl]aspartic acid a) N-[S-Acetyl-2'-benzyl-3'-mercaptopropionyl]aspartic acid dimethyl ester Prepared by Method B of Example 19 but using DL-aspartic acid dimethyl ester hydrochloride (Aldrich). This gave the title compound as a clear oil, an approximately equimolar mixture of diastereoisomers, in 61% yield. $\delta_H$ (CDCl$_3$) 2.30, 2.33 (3H, MeCS), 2.55–2.70 (1H, m, CH$_2$C HCH$_2$), 2.80–3.15 (6H, m, CHCHCH$_2$, CH$_2$CO$_2$), 3.56, 3.68, 3.69, 3.70 (6H, 4s, MeO), 4.7–4.8 (1H, m, HCN), 6.25, 6.39 (1H, 2bd, NH), 7.10–7.30 (5H, m, Ar-H).

b) N-[2'-Benzyl-3'-mercaptopropionyl]aspartic acid

Prepared by Method C of Example 19 but utilising N-(S-acetyl-2'-benzyl-3'-mercaptopropionyl)aspartic acid dimethyl ester and stirring with sodium sulphide for 3 hours. This afforded the title compound as a clear oil, an approximately equimolar mixture of diastereoisomers.

$\delta_H$ (O=C(CD$_3$)$_2$) 2.45–3.06 (7H, m, CH$_2$CHCH$_2$, CH$_2$CO$_2$), 4.65–4.75 (1H, m, HCN), 7.15–7.30 (5H, m, Ar-H), 7.50, 7.60 (1H, 2bd, NH).

Example 5

N-[2'-Benzyl-3'-mercaptopropionyl]tryptophan a) N-[2'-Benzyl-3'-mercaptopropionyl]tryptophan methyl ester Prepared by the Method B of Example 19 but on a 1:1 mixture of D and L-tryptophan methyl ester hydrochlorides (178 mg, 0.7 mmol, Aldrich). This afforded the title compound as a clear oil in 80% yield, as an approximately equimolar mixture of diastereoisomers. These were partially separated.

Less polar: $\delta_H$ (CDCl$_3$) 2.27 (3H, s, MeCOS), 2.55 (1H, m, CH$_2$CHCH$_2$), 2.75–3.08 (4H, m, CH$_2$CHCH$_2$), 3.25 (2H, d, CH$_2$CN), 3.56 (3H, MeO), 4.85 (1H, app.dq HCN), 5.88 (1H, bd, NH-amide), 6.90 (1H, d, Ar-H), 7.00–7.50 (9H, m, Ar-H), 8.2 (1H, bs, NH-indole).

More polar: $\delta_H$ (CDCl$_3$) 1.29 (3H, s, MeCOS), 2.53 (1H, m, CH$_2$CHCH$_2$), 2.75–3.10 (4H, m, CH$_2$CHCH$_2$), 3.23 (2H, d, CHCN), 3.62 (3H, MeO), 4.85 (1H, app.dq HCN), 5.93 (1H, bd, NH-amide), 6.29 (1H, d, Ar-H), 7.00–7.50 (9H, m, Ar-H), 8.0 (1H, bs, NH-indole).

b) N-[2'-Benzyl-3'-mercaptopropionyl]-D-tryptophan methyl ester

Prepared by the method for the racemate [Example 5a)] but using D-tryptophan methyl ester. The title compound was obtained as two diastereomers partially separated into a (a): a 2:1 mixture of the less and more polar isomers and (b): the pure more polar isomer. Both were waxes with corresponding n.m.r. spectra to those described for the racemate.

c) N-[2'-Benzyl-3'-mercaptopropionyl]-L-tryptophan methyl ester

Prepared by the method for the racemate [Example 5a] but using L-tryptophan methyl ester. The title compound was obtained as two diastereomers partially separated into a (c) a 3:1 mixture of the less and more polar isomers and (d) a 1:2 mixture of the less and more polar isomers. Both were waxes with corresponding n.m.r. spectra to those described for the racemate d) N-[2'-Benzyl-3'-mercaptopropionyl]tryptophan Prepared by Method C of Example 19 but on N-(S-acetyl-2'-benzyl-3'-mercaptopropionyl)-tryptophan methyl ester (60 mg, 0.14 mmol). This afforded the title compound as a clear oil, an approximately equimolar mixture of diastereoisomers.

$\delta_H$ (O=C(CD$_3$)$_2$) 2.35–2.55 (1H, m, CH$_2$CHCH$_2$), 2.60–3.00 (4H, m, CH$_2$CHCH$_2$), 3.10–3.40 (2H, m, H$_2$CHCN), 4.75–4.90 (1H, H$_2$CHCN), 6.80–7.40 (10H, m, Ar-H), 7.50, 7.60 (1H, 2d, NH-amide), 10.0, 10.1 (1H, 2bs, NH-indole).

e) N-[2'-Benzyl-3'-mercaptopropionyl]-D-tryptophan

Prepared as for the racemate [Example 5d] but using the partially separated isomer mixtures of N-[2'-benzyl-3'-mercaptopropionyl]-D-tryptophan methyl ester independantly.

From the less polar ester mixture (a): $\delta_H$ (O=C(CD$_3$)$_2$) 2.35–2.55 (1H, m, CH$_2$CHCH$_2$), 2.60–3.00 (4H, m, C H$_2$CHCH$_2$), 3.10–3.40 (2H, mn, H$_2$CHCN), 4.75–4.90 (1H, H$_2$CHCN), 6.80–7.40 (10H, m, Ar-H), 7.65 (1H, d, NH-amide), 10.1 (1H, bs, NH-indole); m/z (NH$_3$ DCI) 383 (M+H$^+$ 35%), 132 100%.

From the more polar ester (b): $\delta_H$ (O=C(CD$_3$)$_2$) 2.35–2.55 (1H, m, CH$_2$CHCH$_2$), 2.60–3.00 (4H, m, C H,CHCH$_2$), 3.10–3.20 (2H, m, H$_2$CHCN), 4.7–4.85 (1H, H$_2$CHCN), 6.80–7.40 (10H, m, Ar-H), 7.50, 7.55 (1H, d, NH-amide), 10.0 (1H, bs, NH-indole).

f) N-[2'-Benzyl-3'-mercaptopropionyl]-L-tryptophan

Prepared in an identical manner to that described for the D-isomers [Example 5e] but using each isomer of N-[2'-benzyl-3'-mercaptopropionyl]-L-tryptophan methyl ester mixtures (c) and (d) in turn. The products were obtained with corresponding n.m.r. spectra to those described for the D-isomer.

Example 6

N-[2'-Benzyl-3'-mercaptopropionyl]threonine a) D-Threonine methyl ester hydrochloride Prepared by Method A of Example 19 but on D-threonine (750 mg, 0.16 mmol, Aldrich) over 3 days. This gave the title compound in quantitative yield as a hygroscopic sticky oil.

$\delta_H$ (CD$_3$OD) 1.34 (3H, d, MeCO), 3.87 (3H, s, MeO), 3.94 (1H, d, HCN), 4.29 (1H, dq, HCO)

b) L-Threonine methyl ester hydrochloride

Prepared by Method A of Example 19 but on L-Threonine (750 mg, 0.16 mmol, Aldrich) over 3 days. This gave the title compound in quantitative yield as a hygroscopic sticky oil with an identical n.m.r. spectrum to the D-isomer.

c) N-[S-Acetyl-2'-benzyl-3'-mercaptopropionyl]threonine methyl ester

Prepared by Method B of Example 19 but on a 1:1 mixture of D and L threonine methyl ester hydrochlorides (119 mg, 0.7 mmol). This afforded the title compound as a clear oil, an approximately 1:1 mixture of diastereomers in 42% yield.

$\delta_H$ (CDCl$_3$) 0.78, 1.20 (1H, 2d, MeCHOH), 2.1 (1H, bs, OH), 2.34 (3H, 2s, MeCOS), 2.70–3.15 (5H, m, CH$_2$CHCH$_2$), 3.65, 3.74 (3H. 2s, MeO), 4.12, 4.28 (1H, 2dq HCOH), 4.44, 4.53 (1H, 2dd, HCN), 6.12, 6.20 (1H, 2bd, NH), 7.15–7.30 (5H, m, Ar-H).

d) N-[2'-Benzyl-3'-mereaptopropionyl]threonine

Prepared by Method C of Example 19 but on N-(S-acetyl-2'-benzyl-3'-mercaptopropionyl)threonine methyl ester (60 mg, 0.17 mmol). This gave the title compound as a clear oil, an approximately equimolar mixture of diastereoisomers.

$\delta_H$ (O=C(CD$_3$)$_2$) 0.89, 1.20 (1H, 2d, MeCHOH), 2.45–3.10 (5H, m, CH$_2$CHCH$_2$), 4.40–4.60 (2H, m, OCHCHN), 5.9 (3H, bs, SH,CO$_2$H, OH), 7.10–7.30 (5H, m, Ar-H), 7.70, 7.75 (1H, 2d, NH).

Example 7

N-[2'-Benzyl-3'-mercaptopropionyl]cysteine a) D-Cystine dimethyl ester dihydrochloride Prepared by Method A of Example 19 but utilising D-cystine (Aldrich). This afforded the title compound as a white crystalline solid in quantitative yield.

$\delta_H$ (CD$_3$OD) 3.38 (4H, ddd, CH$_2$), 3.89 (6H, s, MeO), 4.48 (2H, dd, HCN).

b) N-[S-Acetyl-2'-benzyl-3'-mercaptopropionyl]cystine methyl ester

Prepared by Method B of Example 19 but utilising a 1:1 mixture of D and L-cystine methyl ester hydrochlorides (120 mg, 0.35 mmol, L-isomer from Aldrich) and 2-acetylthiomethyl-3-phenylpropanoic acid (150 mg, 0.63 mmol). This afforded the title compound a s a clear oil, an approximately equimolar mixture of diastereoisomers, in 43% overall yield.

$\delta_H$ (CDCl$_3$) 2.34, 2.35 (6H, 2s, MeCS), 2.60–3.15 (14H, m, CH$_2$CHCH$_2$, CH$_2$S), 3.70, 3.74 (6H, 2s, MeO), 4.6–4.8 (1H, m, HCN), 6.35 (2H, bs, NH), 7.15–7.30 (10H, m, Ar-H).

c) N-[2'-Benzyl-3'-mercaptopropionyl]cysteine

N-(S-Acetyl-2'-benzyl-3'-mercaptopropionyl)cystine methyl ester (50 mg) was dissolved in degassed methanol (5 ml) and treated with sodium sulfide nonahydrate (300 mg) and dithiothreitol (122 mg). The mixture was stirred at RT for 14 hours then poured into water (30 ml) and extracted with chloroform (2×20 ml), the aqueous phase acidified to pH 1–2 and re-extraced with ethyl acetate (3×10 ml), dried, (MgSO$_4$) filtered and evaporated to a clear oil, the title compound as an approximately equimolar mixture of diastereoisomers, in 86% yield.

$\delta_H$ (CDCl$_3$) 2.55–3.30 (7H, m CH$_2$CHCH$_2$, CH$_2$S), 4.25–4.40 (1H, m, HCN), 6.30, 6.40 (1H, 2d, NH), 7.15–7.33 (5H, m, Ar-H); m/z (ESI$^+$) 298 (M-H$^-$, 100%).

Example 8

N-[2'-Benzyl-3'-mercaptopropionyl]tyrosine a) D-Tyrosine methyl ester hydrochloride Prepared by Method A of Example 19 using D-tyrosine (Aldrich) as the amino acid. This gave the title compound as a white crystalline solid in quantitative yield.

$\delta_H$ (CD$_3$OD) 3.05, 3.18 (2H, 2dd, arCH$_2$), 4.22 (1H, dd, HCN), 6.79, 7.07 (4H, 2d, Ar-H).

b) N-[S-Acetyl-2'-benzyl-3'-mereaptopropionyl]tyrosine methyl ester

Prepared by Method B of Example 19 and utilising a 1:1 mixture of D and L-tyrosine methyl ester hydrochlorides (232 mg, 1 mmol, L isomer from Aldrich) with the addition of triethylamine (101.2 mg, 1 mmol). This gave the title compound as a sticky wax, an approximately equimolar mixture of diastereoisomers, in 75% yield.

$\delta_H$ (CDCl$_3$) 2.30, 2.32 (3H, 2s, MeCS), 2.55–2.70 (1H, m, CH$_2$CHCH$_2$), 2.80–3.37 (6H, m, CHCHCH$_2$, CH$_3$Ar), 3.60, 3.68 (3H, 2s, MeO), 4.74, 4.82 (1H, 2app.dq, HCN), 5.90, 5.93 (1H, 2bd, NH), 6.41, 6.58, 6.69, 6.93 (4H, 4d, Ar-H), 7.10–7.35 (5H, m, Ar-H).

c) N-[2'-Benzyl-3'-mercaptopropionyl]tyrosine

Prepared by Method C of Example 19 but utilising N-(S-acetyl-2'-benzyl-3'-mercaptopropionyl)tyrosine methyl ester. This gave the title compound as a clear oil, an approximately equimolar mixture of diastereoisomers.

$\delta_H$ (O=C(CD$_3$)$_2$) 2.35–2.55 (1H, m, CH$_2$C$\underline{H}$CH$_2$), 2.70–3.20 (7H, m, C$\underline{H}_2$CHC$\underline{H}_2$, CH$_2$Ar), 4.65–4.75 (1H, m, HCN), 6.65–7.35 (11H, m, Ar-H, NH), 8.2 (1H, bs, OH); m/z (ESI) 358 (M-H$^-$, 100%).

Example 9

N-[2'-Benzyl-3'-mercaptopropionyl]phenylglycine a) L-Phenylglycine methyl ester hydrochloride Prepared by Method A of Example 19 but using L-phenylglycine (Aldrich). The title compound was obtained as a white crystalline solid in quantitative yield.

$\delta_H$ (CD$_3$OD) 3.80 (3H, s, MeO), 5.19 (1H, s, HCN), 7.42–7.50 (5H, m, Ar-H).

b) D-Phenylglycine methyl ester hydrochloride

Prepared by method A of Example 19 but using D-phenylglycine (Aldrich). The title compound was obtained as a white crystalline solid in quantitative yield with an identical n.m.r. spectrum to the L-isomer.

c) D-Phenylglycine ethyl ester hydrochloride

Prepared by Method A of Example 19 but using D-phenylglycine and ethanol in place of methanol. This gave the title compound as a white crystalline solid in quantitative yield.

$\delta_H$ (CD$_3$OD) 1.20 (3H, bt, MeC), 4.29 (2H, dq, CH$_2$O), 5.18 (1H, s, HCN), 7.42–7.50 (5H, m, Ar-H).

d) N-[S-Acetyl-2'-benzyl-3'-mercaptopropionyl]-phenylglycine methyl ester

Prepared by Method B of Example 19 but using a mixture of L- and D-phenylglycine methyl ester hydrochloride (201 mg, 1.0 mmol). This gave the title compound in 70% yield as a racemic mixture of the diastereomers.

Less polar: $\delta_H$ (CDCl$_3$) 2.26 (3H, s, MeCOS), 2.59 (1H, m, CH$_2$C$\underline{H}$CH$_2$), 2.80–3.11 (4H, m, C$\underline{H}_2$CHC$\underline{H}_2$), 3.65 (3H, MeO), 5.43 (1H, d, HCN), 6.32 (1H, bd, NH), 6.95–7.35 (10H, m, Ar-H).

More polar: $\delta_H$ (CDCl$_3$) 2.34 (3H, s, MeCOS), 2.69 (1H, m, CH$_2$C$\underline{H}$CH$_2$), 2.82,–3.12 (4H, m, C$\underline{H}_2$CHC$\underline{H}_2$), 3.68 (3H, MeO), 5.49 (1H, app.dq HCN), 6.37 (1H, bd, NH), 7.00–7.35 (10H, m, Ar-H).

e) N-[2'-Benzyl-3'-mercaptopropionyl]phenylglycine

Prepared by Method C of Example 19 but using N-(S-acetyl-2'-benzyl-3'-mercaptopropionyl)-phenylglycine methyl ester. This afforded the title compound as a clear oil, an approximately equimolar mixture of diastereoisomers.

$\delta_H$ (O=C(CD$_3$)$_2$) 2.45–2.55 (1H, m, CH$_2$C$\underline{H}$CH$_2$), 2.70–3.10 (4H, m, C$\underline{H}_2$CHC$\underline{H}_2$) 3.10–3.40 (2H, m, $\underline{H}_2$CHCN), 4.95,5.05 (1H, $\underline{H}$CN), 7.10–7.50 (10H, m, Ar-H), 7.78, 7.83 (1H, 2d, NH).

f) [2'S]-N-[2'-Benzyl-3'-mercaptopropionyl]-D-phenylglydne methyl ester and g) [2'R]-N-[2'-Benzyl-3'-mercaptopropionyl]-D-phenylglycine metlyl ester Prepared by the method described above for the racemate (Example 9d and 9e), using the D-phenylglycine methyl ester hydrochloride enantiomer and separating the diastereomers by chromatography. The (2'-S) isomer corresponds to the more polar isomer.

Less polar isomer $[\alpha_D^{20}]$ −29.5° (c, 1.425, CHCl$_3$).
More polar isomer $[\alpha_D^{20}]$ −134.7° (c, 1.425, CHCl$_3$).

h) N-[S-Acetyl-2'-benzyl-3'-mercaptopropionyl]-D-phenylglycine

A stirred suspension of D-phenylglycine (302 mg, 2 mmol) in chloroform (5 ml) and acetonitrile (0.5 ml) was treated with chlorotrimethylsilane (0.26 ml, 2 mmol) and the mixture refluxed for 1 hour. It was cooled in an ice-bath. A solution of 2-acetylthiomethyl-3-phenylpropanoyl acid chloride (prepared from the carboxylic acid and oxalyl chloride by Method B of Example 19) (1 mmol) in chlorofonn (5 ml) was added dropwise to the ice-cold silyl ester, followed by triethylamine (0.62 ml, 4.4 mmol). The mixture was allowed to gain room temperature and stirred for 2 hours, washed with 1M hydrochloric acid (10 ml), water (2×10 ml), saturated brine (10 ml), dried (MgSO$_4$), and evaporated. The residue was purified by flash chromatography on silica, eluting with mixtures of methanol in dichloromethane to give N-[S-acetyl-2'-benzyl-3'-mercaptopropionyl]-D-phenylglycine (355 mg, 95%).

$\delta_H$ (CDCl$_3$) 2.23 (3H, s, COCH$_3$), 2.62–3.18 (5H, m, 2×CH$_2$, 2'-CH), 4.30 (1H, CO$_2$H), 5.42 (1H, bs, α-CH), 6.56 (1H, bs, NH), 7.20 (10H, m, 2×Ph) ppm. EIMS M$^+$ 371. DCIMS MH 372.

i) [2'S]-N-[2'-Benzyl-3'-mercaptopropionyl]-D-phenylglycine

Prepared by the method described above for the racemate (Example 9e) but using the (2'S)-N-(2'-benzyl-3'-mercaptopropionyl)-D-phenylglycine methyl ester diastereomer.

j) [2'R]-N-[2'-Benzyl-3'-mercaptopropionyl]-D-phenylglycine

Prepared by the method described above for the racemate (Example 9e) but using the (2'R)-N-(2'-benzyl-3'-mercaptopropionyl)-D-phenylglycine methyl ester diastereomer.

k) N-[2'-Benzyl-3'-mercaptopropionyl]-D-phenylglycine

A solution of N-(S-acetyl-2'-benzyl-3'-mercaptopropionyl)-D-phenylglycine (100 mg) in methanol (1 ml) at room temperature was treated with 0.880S.G. ammonia (0.5 ml). After 0.25 h the solution was diluted with ethyl acetate (10 ml), washed with 1M hydrochloric acid (5 ml), water (2×5 ml), saturated brine (5 ml), dried (MgSO$_4$) and evaporated. Purified by flash chromatography on silica eluting with mixtures of methanol in dichloromethane, it gave N-(2'-benzyl-3'-mercaptopropionyl)-D-phenylglycine as a mixture of diastereomers (3:2, 2'S:2'R). $\delta_H$[(CD$_3$)$_2$SO] 2.09 (0.6H, t, J 7.8 Hz, 2'S-SH), 2.30–3.05 (5.4H, m, 2×CH$_2$, α-CH, 2'R-SH), 5.03 (1H, 2d, J 7.1, 7.0 Hz, 2×α-H), 7.25 (10H, m, 2×Ph), 8.08 (0.4H, d, J 7.0 Hz, NH), 8.21 (0.6H, d, J 7.1 Hz, NH). EIMS M$^+$ 329. DCIMS MH$^+$ 330.

Example 10

N-[(R)- and N-[(S)-2'-Benzyl-3'-mercaptopropionyl] glycine a) N-[S-Acetyl-2'-benzyl-3'-mercaptopropionyl]glycine methyl ester Prepared by Method B of Example 19 but utilising glycine methyl ester hydrochloride (Aldrich). This afforded the title compound as a colourless oil in 62% yield.

$\delta_H$ (CDCl$_3$) 2.32 (3H, s, MeCS), 2.65 (1H, dddd, CH4CH$_2$C$\underline{H}_2$), 2.85, 2.97, 3.04, 3.11 (4H, 4dd, C$\underline{H}_2$CHC$\underline{H}_2$), 3.70 (3H, s, MeO), 3.80, 4.00 (2H, 2dd, CH$_2$CO$_2$), 5.90 (1H, bt, NH), 7.15–7.30 (5H, m, Ar-H).

b) N-[2'-Benzyl-3 '-mercaptopropionyl]glycine

Prepared by Method C of Example 19 but using N-(S-acetyl-2'-benzyl-3'-mercaptopropionyl)glycine methyl ester. Thiorphan-was obtained as a white solid.

$\delta_H$ (O=C(CD$_3$)$_2$) 2.50 (1H, m, CH$_2$C$\underline{H}$CH$_2$), 2.70–3.10 (4H, m, C$\underline{H}_2$CHC$\underline{H}_2$), 3.2 (2H, bs, SH, CO$_2$H), 3.85, 4.01 (2H, 2dd, CH$_2$CO$_2$), 7.15–7.30 (5H, m, Ar-H), 7.5 (1H, bt, NH).

c) [2'S]-N-[2'-Benzyl-3'-mereaptopropionyl]glycine and [2'R]-N-[2'-Benzyl-3'-mercaptopropionyl]glycine Racemic N-(S-acetyl-2'-benzyl-3'-mercaptopropionyl) glycine methyl ester (15 mg) was separated into its two component isomers using chiral HPLC (Chiralpak-AD, mobile phase 80:20 hexane:ethanol). Each isomer was hydrolysed by Method C of Example 19 but on a 4 mg scale. The dextrorotatory isomer of the ester gave (2'R)-N-(2thiomethyl-3-phenylpropanoyl)glycine, $\alpha_D^{20}$ −34° (c, 3.5 in EtOH), otherwise spectroscopically identical to thiorphan. The laevorotatory ester enantiomer hydrolysed to give the other antipode of thiorphan with a corresponding but opposite rotation.

Example 11

N-[2'-Benzyl-3'-mercaptopropionyl]-3-hydroxyphenylglycine a) 3-Hydroxyphenyiglycine methyl ester hydrochloride Prepared by Method A of Example 19 but using 3-hydroxyphenylglycine, obtained from 3-hydroxybenzaldehyde (Aldrich) via the Strecker synthesis. This gave the title compound as a white crystalline solid in quantitative yield.

$\delta_H$ (MeOD) 3.80, (3H, s, ), 5.10 (1H, s, HCN), 6.90–7.36 (4H, m, Ar-H).

b) N-[S-Acetyl-2'-benzyl-3'-mercaptopropionyl]-3-hydroxyphenylglycine methyl ester Prepared by Method B of Example 19 but using 3-hydroxyphenylglycine methyl ester hydrochloride. This gave the title compound as a colourless oil in 41% yield, as an approximately equimolar mixture of diastereoisomers.

$\delta_H$ (CDCl$_3$) 2.28, 2.35 (3H, 2d, AcS), 2.70–3.15 (5H, m, CH$_2$CHCH$_2$), 3.65, 3.70 (3H, 2s, OMe), 5.40, 5.43 (1H, 2d, HCN), 6.50–7.60 (10H, m, Ar-H, NH).

c) N-[2'-Benzyl-3'-mercaptopropionyl]-3-hydroxyphenylglycine

Prepared by Method C of Example 19 but using N-(S-acetyl-2'-benzyl-3'-mercaptopropionyl)-3-hydroxyphenylglycine methyl ester. This gave the title compound as a colourless oil, an approximately equimolar mixture of diastereoisomers.

$v_{max}$ (film) 3358 (OH), 3025–2931 (CH-Str), 2566 (SH), 1731 (C═O, Acid), 1642 (C═O, Amide), 1525–1454 (Ar-Str); δH (O═C(CD$_3$)$_2$) 2.40–2.58 (1H, m, CH$_2$CHCH$_2$), 2.70–3.13 (4H, CH$_2$CHCH$_2$), 5.40, 5.49 (1H, 2d; HCN), 6.70–7.30 (9H, m, Ar-H), 7.75, 7.80 (1H, 2bd, NH), 8.5 (1H, bs, CO$_2$H).

Example 12

N-[2'-Benzyl-3'-mercaptopropionyl]-4-hydroxy-D-phenylglycine a) N-(S-Acetyl-2'-benzyl-3'-mercaptopropionyl]-4-hydroxy-D-phenylglycine ethyl ester Prepared by Method B of Example 19 but using 4-hydroxy-D-phenylglycine methyl ester hydrochloride, prepared from 4-hydroxy-D-phenylglycine (Aldrich) by Method A of Example 19. This gave the title compound as a colourless oil in 38% yield, as an approximately equimolar mixture of diastereoisomers.

δH (CDCl$_3$) 1.19 (3H, dt, CH$_2$CH$_3$), 2.28, 2.34 (3H, 2s, AcS), 2.68–2.78 (1H, m, CH$_2$CHCH$_2$), 2.85–3.15 (4H, CH$_2$CHCH$_2$), 4.00–4.22 (2H, m, OCH$_2$), 5.30–5.32 (1H, 2d, HCN), 6.50–7.34 (10H, m, Ar-H, NH).

b) N-[2'-Benzyl-3'-mercaptopropionyl]-4-hydroxy-D-phenylglycine

Prepared by Method C of Example 19 but using N-(S-acetyl-2'-benzyl-3'-mercaptopropionyl)-4-hydroxy-D-phenylglycine methyl ester. This gave the title compound as a colourless oil, an approximately equimolar mixture of diastereoisomers.

$v_{max}$ (film) 3310 (OH), 3015–2940 (CH-Str), 2567 (SH), 1731 (C═O, Acid), 1635 (C═O, Amide), 1535–1445 (Ar-Str); δH (O═C(CD$_3$)$_2$) 2.40–2.58 (1H, m, CH$_2$CHCH$_2$), 2.75–3.15 (4H, CH$_2$CHCH$_2$), 5.38, 5.34 (1H, 2d, HCN), 6.70–7.35 (9H, m, Ar-H), 7.69, 7.78 (1H, 2bd, NH), 8.5 (1H, bs, CO$_2$ H).

Example 13

N-[2'-Benzyl-3'-mercaptopropionyl]4-methoxyphenylglycine a) 4-Methoxyphenylglycine methyl ester hydrochloride Prepared by Method A of Example 19 but using 4-methoxyphenylglycine (Doyle, et al., *J. Chem. Soc.*, 1962, 1440 and refs. therein). This gave the title compound as a white crystalline solid in quantitative yield.

δH (MeOD) 3.80, 3.82 (3H, 2s, 2×OMe), 5.10 (1H, s, HCN), 7.01–7.36 (4H, 2d, Ar-H).

b) N-[S-Acetyl-2'-benzyl-3'-mercaptopropionyl]-4-methoxyphenylglycine methyl ester Prepared by Method B of Example 19 but using 4-methoxyphenylglycine methyl ester hydrochloride. This gave the title compound as a colourless oil in 57% yield, an approximately equimolar mixture of diastereoisomers.

δH (CDCl$_3$) 2.30, 2.34 (3H, 2d, AcS), 2.60–2.75 (5H, m, CH$_2$CHCH$_2$), 2.80–3.10 (4H, m, CH$_2$CHCH$_2$), 3.63, 3.67, 3.77, 3.78 (6H, m, 2×OMe), 5.38, 5.41 (1H, 2d, HCN), 6.35, 6.38 (1H, s, NH), 6.75–7.30 (9H, m, Ar-H).

c) N-[2'-Benzyl-3'-mercaptopropionyl]-methoxyphenylglycine

Prepared by Method C of Example 19 but using N-(S-acetyl-2'-benzyl-3'-mercaptopropionyl)-4-methoxyphenylglycine methyl ester. This gave the title compound as a colourless oil, an approximately equimolar mixture of diastereoisomers.

$v_{max}$ (film) 3271 (OH), 3055–2935 (CH-str), 2550 (SH), 1731 (C═O, Acid), 1633 (C═O, Amide), 1513–1454 (Ar-Str); δH (CDCl$_3$) 2.48–3.10 (5H, CH$_2$CHCH$_2$), 3.78, 3.79 (3H, 2s, MeO), 5.38–5.45 (1H, 2d, HCN), 6.42, 6.48 (1H, 2d, NH), 6.75–7.25 (9H, m, Ar-H).

Example 14

N-[2'-Benzyl-3'-mercaptopropionyl]-4-hydroxy-3-nitrophenylglycine a) 4-Hydroxy-3-nitrophenylglycine methyl ester hydrochloride Prepared by Method A of Example 19 but using 4-hydroxy-3-nitrophenylglycine, obtained from 4-hydroxy-3-nitrobenzaldehyde (Aldrich) via the Strecker synthesis. This gave the title compound as a cream solid in quantitative yield.

$\delta_H$ (MeOD) 3.85 (3H, s, OMe), 5.25 (1H, s, HCN), 7.24, 8.24 (2H, 2d, Ar-H), 7.66 (2H, dd, Ar-H).

b) N-[S-Acetyl-2'-benzyl-3'-mercaptopropionyl]-4-hydroxy-3-nitrophenylglycine methyl ester Prepared by Method B of Example 19 but using 4-hydroxy-3-nitrophenylglycine methyl ester hydrochloride. This gave the title compound as a yellow oil in 40% yield, an approximately equimolar mixture of diastereoisomers.

$\delta_H$ (CDCl$_3$) 2.35, 2.40 (3H, 2s, AcS), 2.70–3.30 (5H, m, CH$_2$CHCH$_2$), 3.67, 3.72 (3H 2s, OMe), 5.35, 5.53 (1H, 2dd, HCN), 6.49–6.52 (1H, bm, NH), 6.70–8.1 (8H, m, Ar-H)

c) N-[2'-Benzyl-3'-mercaptopropionyl]-[4-hydroxy-3-nitrolphenylglycine

Prepared by Method C of Example 19 but using N-(S-acetyl-2'-benzyl-3'-mercaptopropionyl)-4-hydroxy-3-nitrophenylglycine methyl ester. This gave the title compound as a yellow oil, an approximately equimolar mixture of diastereoisomers.

$\nu_{max}$ (film) 3305 (OH), 3028–2931 (CH-Str), 2573 (SH), 1731 (C=O, Acid), 1630 (C=O, Amide), 1538–1432 (Ar-Str).

Example 15

N-[2'-Benzyl-3'-mercaptopropionyl]-3,4-dihydroxy-D-phenylglycine a) 3,4-Dihydroxy-D-phenylglycine methyl ester hydrochloride Prepared by Method A of Example 19 but using 3,4-dihydroxy-D-phenylglycine, obtained from 3,4-dihydroxybenzaldehyde by the Strecker synthesis. This gave the title compound as a white solid in quantitative yield.

δH (MeOD) 3.8 (3H, s, OMe), 5.1 (1H, s, HCN), 6.7–7.3 (3H, m, Ar-H).

b) N-[S-Acetyl-2'-benzyl-3'-mercaptopropionyl]-3,4-dihydroxy-D-phenylglycine methyl ester Prepared by Method B of Example 19 but using 3,4-dihydroxy-D-phenylglycine methyl ester hydrochloride. This gave the title compound as a clear oil in 11% yield an approximately equimolar mixture of diastereoisomers.

δH (CDCl$_3$) 2.36, 2.38 (3H, 2d, AcS), 2.65–3.30 (5H, m, CH$_2$CHCH$_2$), 3.65, 3.70 (3H, 2s, OMe), 5.28, 5.35 (1H, 2d, HCN), 6.50 (1H, bs, NH), 6.70–8.10 (8H, m, Ar-H).

c) N-[2'-Benzyl-3'-mercaptopropionyl]-3,4dihydroxy-D-phenylglycine

Prepared by Method C of Example 19 but using N-(S-acetyl-2'-benzyl-3'-mercaptopropionyl)-3,4-dihydroxy-D-phenylglycine methyl ester (21 mg). This gave the title compound as a clear oil, an approximately equimolar mixture of diastereoisomers νmax(film) 3317 (OH), 3025–2922 (CH-Str), 2630 (SH), 1734 (C=O, Acid), 1691 (C=O, Amide), 1515–1446 (Ar-Str)

Example 16

N-[2'-Benzyl-3'-mercaptopropionyl]-4-fluoro-D-phenylglycine a) N-[S-Acetyl-2'-benzyl-3'-mercaptopropionyl]-4-fluoro-D-phenylglycine methyl ester N-[Benzyloxycarbonyl]-4-fluoro-D-phenylglycine (1.0 g, 3.3 mmol) was dissolved in ethanol (5 ml) and treated with cyclohexene (0.5 ml) and 10% palladium on carbon. The mixture was heated to reflux for 1 hour then cooled and poured onto celite. A 1:1 mixture of water and ethanol (50 ml) was introduced and the resulting suspension acidified to pH 1 with hydrochloric acid. The mixture was heated to 80° C., hot filtered and evaporated then coevaporated with toluene to give 4-fluoro-D-phenylglycine (D. Landini, et al, Synthesis, 1970, 1, 26) as an oil (50 mg). This was dissolved in a mixture of acetyl chloride (1 ml) in methanol (4 ml) (CARE) and maintained-at RT for 24 hours. The solvent was removed to give a white solid 4-fluorophenylglycine methyl ester hydrochloride which was used in Method B of Example 19 without further purification. This gave the tiLle compound as a clear oil in 44% yield, an approximately equimolar mixture of diastereoisomers.

δH (CDCl$_3$) 2.30, 2.40 (3H, 2d, AcS), 2.65–3.15 (5H, m, CH$_2$CHCH$_2$), 3.62, 3.68 (3H, 2d, OMe), 5.40–5.45 (1H, 2d, HCN), 6.35 (1H, bs, NH), 6.90–7.35 (9H, m, Ar-H).

b) N-[2'-Benzyl-3'-mercaptopropionyl]-4-fluoro-D-phenylglycine

Prepared by Method C of Example 19 but using N-(S-acetyl-2'-benzyl-3'-mercaptopropionyl)-4-fluoro-D-phenylglycine methyl ester hydrochloride. This gave the title compound as a clear oil, an approximately equimolar mixture of diastereoisomers.

νmax(film) 3320 (OH), 3028–2931 (CH-Str), 2569 (SH), 1731 (C=O, Acid), 1651 (C=O, Amide), 1510–1454 (Ar-Str).

Example 17

N-[2'-Benzyl-3'-mercaptopropionyl]-3-fluorophenylglycine a) 3-Fluorophenylglycine methyl ester hydrochloride Prepared by Method A of Example 19 but using 3-fluorophenylglycine (Aldrich). This gave the title compound as a white solid in quantitative yield.

δH (MeOD) 3.83 (3H, s, OMe), 5.27 (1H, s HCN), 7.2–7.6 (4H, m, Ar).

b) N-[S-Acetyl-2'-benzyl-3'-mercaptopropionyl]-3-fluorophenylglycine methyl ester Prepared by Method B of Example 19 but using 3-fluorophenylglycine methyl ester hydrochloride and triethylamine (101 mg). This gave the title compound as a clear oil in 42% yield, an approximately equimolar mixture of diastereoisomers.

δH (CDCl$_3$) 2.32, 2.36 (3H, 2s, AcS), 2.65–3.15 (5H, m, CH$_2$CHCH$_2$), 3.65–3.71 (3H, 2s, OMe), 5.42–5.48 (1H, 2d, HCN), 6.4 (1H, bs, NH), 6.65–7.4 (9H, m, Ar-H).

c) N-[2'-Benzyl-3'-mercaptopropionyl]-3-fluorophenylglycine

Prepared by Method C of Example 19 but using N-[S-acetyl-2'-benzyl-3'-mercaptopropionyl]-3-fluorophenylglycine methyl ester hydrochloride. This gave the title compound as a clear oil, an approximately equimolar mixture of diastereoisomers.

νmax(film) 3312 (OH), 3029–2934 (CH-Str), 2569 (SH), 1731 (C=O, Acid), 1659 (C=O, Amide), 1537–1453 (Ar-Str).

Example 18

N-[2'-Benzyl-3'-mercaptopropionyl]-3-nitro-D-phenylglycine a) 3-Nitro-D-phenylglycine methyl ester hydrochloride Prepared by Method A of Example 19 but using 3-Nitro-D-phenylglycine (Doyle et al., *J. Chem Soc.*, 1962, 1440 and refs. therein). This gave the title compound as a cream solid in quantitative yield.

δH (MeOD) 3.85 (3H, s, OMe), 5.45 (1H, s), 7.7–8.5 (4H, m, Ar-H).

b) N-(S-Acetyl-2'-benzyl-3'-mercaptopropionyl]-3-nitro-D-phenylglycine methyl ester Prepared by Method B of Example 19 but using 3-Nitro-D-phenylglycine methyl ester hydrochloride and triethylamine (101 mg). This gave the title compound as a yellow oil in 63% yield, an approximately equimolar mixture of diastereoisomers.

$\delta_H$ (CDCl$_3$) 2.34, 2.35 (3H, 2s, AcS), 2.60–3.15 (SH, m, CH$_2$CHCH$_2$), 3.67, 3.72 (3H, 2s, OMe), 5.47–5.56 (1H, 2dd, HCN), 6.50–6.65 (1H, bm, NH), 6.95–8.2 (9H, m, Ar-H).

c) N-[2'-Benzyl-3'-mercaptopropionyl]-3-nitro-D-phenylglycine

Prepared by Method C of Example 19 but using N-[S-acetyl-2'-benzyl-3'-mercaptopropionyl]-3-nitro-D- phenylglycine methyl ester. This gave the title compound as a yellow oil, an approximately equimolar mixture of diastereoisomers.

$v_{max}$ (film) 3326 (OH), 3175–2930 (CH-Str), 2600 (SH), 1738 (C=O, Acid), 1650 (C=O, Amide), 1530–1349 (Ar-Str); $\delta_H$ (CDCl$_3$) 2.55–2.31 (5H, m, CH$_2$CHCH$_2$), 5.45, 5.50 (1H, 2d, HCN), 6.48, 6.52 (1H, 2bd, NH), 7.00–8.15 (9H, m, Ar-H).

Example 19

N-[2'-Benzyl-3'-mercaptopropionyl]-2-fluorophenylglycine a) 2-Fluorophenylglycine methyl ester hydrochloride (Method A)

Acetyl chloride (4 ml) was added cautiously and dropwise to methanol (20 ml) at 0° C. over 2 minutes. When the addition was completed, the 2-fluorophenylglycine (1 g, 5.9 mmol, Aldrich) was introduced in a single portion. The mixture was stirred until dissolved then allowed to stand at RT for 24 hours. The solvent was evaporated then coevaporated twice from toluene to afford the title compound as a white crystalline solid in quantitative yield.

$\delta_H$ (CD$_3$OD) 3.82 (3H, s, Me), 5.42 (1H, s, CHCO), 7.20–7.60 (4H, m, Ar-H).

b) N-[S-Acetyl-2'-benzyl-3'-mercaptopropionyl]-2-fluorophenylglycine methyl ester (Method B)

2-Acetylthiomethyl-3-phenylpropanoic acid [EP03613651] (0.2 g, 0.84 mmol) was added to a solution of dichloromethane (3 ml) and oxalyl chloride (0.25 ml). A drop of dimethylformamide was introduced and the mixture stirred under argon, permitting the escape of evolved gases. After 1 hour, the solvent was evaporated then coevaporated twice with toluene. A sample of the 2-fluorophenylglycine methyl ester hydrochloride was introduced (0.183 g, 1 mmol) and pyridine (2 ml) added and the mixture was stirred for 30 minutes. The mixture was evaporated, then partitioned between 0.1M aq. HCl (20 ml) and ethyl acetate (3×20 ml). The combined, dried (MgSO$_4$) organic phase was evaporated and subjected to flash chromatography (hexane—ethyl acetate) to afford the racemic diastereomers of the title compound in 34% yield and approximately equimolar ratio.

$v_{max}$ (film); 3424 (OH), 3013–2919 (CH-Str), 2390 (SH), 1725 (C=O, Acid), 1672 (C=O, Amide), 1513–1419 (Ar-Str): $\delta_H$ (CD$_3$OD) 2.20, 2.34 (3H, 2s, AcS), 2.7–3.2 (5H, m, CH$_2$CHCH$_2$), 3.63, 3.70 (3H, 2s, OMe), 5.65 (1H, d, HCN), 7.0–7.5 (9H, m, 2×Ar).

c) N-[2'-Benzyl-3'-mercaptopropionyl]-2-fluorophenylglycine (Method C)

A solution of the N-(S-acetyl-2'-benzyl-3'-mercaptopropionyl)-2-fluorophenylglycine methyl ester of Example 19b (0.2 mmol) in methanol (2 ml) was degassed with argon for 20 minutes then treated with a solution of sodium sulphide (1 mmol) in degassed water (2 ml). After 30–90 minutes, 0.25M aq. HCl (20 ml) was introduced and the mixture extracted with ethyl acetate (3×20 ml). The dried (MgSO$_4$) organic phases were evaporated to give the title compound as a clear oil, an approximately equimolar mixture of diastereoisomers.

$\delta_H$ (O=C(CD$_3$)$_2$) 2.45–3.10 (3H, m, CH$_2$S, CHCO), 4.0 (2H, vbs, CO$_2$H, SH), 5.80, 5.75 (1H, 2d, HCN), 7.10–7.50 (9H, m, Ar-H), 7.85, 7.95 (1H, bd, NH).

Example 20

N-[2'-Benzyl-3'-mercaptopropionyl]-2-thienylglycine a) 2-Thienylglycine methyl ester hydrochloride Prepared by Method A of Example 19 but using 2-thienylglycine (Ger. Offen. DE 3,528,631). This gave the title compound as a white solid in quantitative yield.

δH (MeOD) 3.85 (3H, s, OMe), 5.5 (1H, s), 7.1, 7.28, 7.62 (3H, m, Ar-H).

b) N-[S-Acetyl-2'-benzyl-3'-mercaptopropionyl]-2-thienylglycine methyl ester

Prepared by Method B of Example 19 but using 2-thienylglycine methyl ester hydrochloride and triethylamine (101 mg, 1 mmol). This gave the title compound as a yellow oil in 44% yield, an approximately equimolar mixture of diastereoisomers.

$\delta_H$ (CDCl$_3$) 2.30–2.35 (3H, 2s, AcS), 2.65–3.15 (5H, m, CH$_2$CHCH$_2$), 3.71–3.77 (3H, 2d, OMe), 5.75, 5.78 (1H, 2d, HCN), 6.3 (1H, bd, NH), 6.7 (0.5H, d, Ar-H), 6.85–7.40 (7.5H, m, 2×Ar).

c) N-[2'-Benzyl-3'-mercaptopropionyl]-2-thienylglycine

Prepared by Method C of Example 19 but using N-(S-acetyl-2'-benzyl-3'-mercaptopropionyl)-2-thienylglycine methyl ester. This afforded the title compound as a clear oil, an approximately equimolar mixture of diastereoisomers.

$v_{max}$ (film) 3412 (OH), 3013–2931 (CH-Str), 2367 (SH), 1737 (C=O, Acid), 1660 (C=O, Amide), 1513–1425 (Ar-Str); $\delta_H$ (O=C(CD$_3$)$_2$) 2.45–2.60 (1H, bm, CHCO), 2.75–3.10 (2H, m, CH$_2$S), 5.3 (2H, vbs CO$_2$H, SH), 5.78, 5.83 (1H, 2d, HCN), 6.8–7.40 (8H, m, Ar-H), 7.90–7.80 (1H, bm, NH).

Example 21

N-[2'-Benzyl-3'-mereaptopropionyl]-N-benzyl-phenylglycine a) N-Benzyl-phenylglycine methyl ester hydrochloride Prepared by Method A of Example 19 but using N-benzyl-phenylglycine (W. Dickinson Burrows, *J. Org. Chem.*, 1966, 31, 3435). This gave the title compound as a white solid in quantitative yield.

δH (MeOD) 3.8 (3H, s, OMe), 4.1–4.3 (2H, q, CH$_2$Ph), 5.25 (1H, s), 7.2 (1H, m, NH), 7.4–7.6 (10H, m, Ar-H).

b) N-[S-Acetyl-2'-benzyl-3'-mercaptopropionyl]-N-benzyl-phenylglycine methyl ester Prepared by Method B of Example 19 but using N-benzyl-phenylglycine methyl ester hydrochloride and triethylamine (101 mg, 1 mmol). This gave the title compound as a colourless oil in 11% yield, as an approximately equimolar mixture of diastereoisomers.

$\delta_H$ (CDCl$_3$) 2.3, 2.4 (3H, 2s, AcS), 2.8–3.2 (5H, m, CH$_2$CHCH$_2$), 3.68, 3.75 (3H, 2s, OMe), 5.55–5.60 (1H, 2s, HCPh), 7.20–7.4 (15H, m, Ar-H).

c) N-[2'-Benzyl-3'-mercaptopropionyl]-N-benzyl-phenylglycine

Prepared by Method C of Example 19 but using N-(S-acetyl-2'-benzyl-3'-mercaptopropionyl)-N-benzyl-phenylglycine methyl ester. This afforded the title compound as a clear oil, an approximately equimolar mixture of diastereoisomers.

$v_{max}$ (film) 3300 (OH), 3028–2917 (CH-Str), 2652 (SH), 1703 (C=O, Acid), 1597 (C=O, Amide), 1498–1419 (Ar-Str).

Example 22

N-[2'-Methyl-3'-mercaptopropionyl]-D-phenylglycine a) N-[S-Acetyl-2'-methyl-3'-mercaptopropionyl]-D-phenylglycine ethyl ester Prepared by Method B of Example 19 but using D-phenylglycine ethyl ester hydrochloride (Example 9c) and S-acetyl-2-methyl-3-mercaptopropionic acid [U.S. Pat. No. 4,046,889]. The title compound was obtained as a white crystalline solid in 78% yield, an approximately equimolar mixture of diastereoisomers.

$\nu_{max}$ (film) 3325, 1728, 1691 and 1647; $\delta_H$ (CDCl$_3$) 1.20 (3H, t, C$\underline{H}$3CH$_2$), 2.31 (3H, s, AcN), 2.54 (1H, ddq, CHC=O), 2.95, 3.14 (2H, 2dd, CH$_2$S), 4.10–4.20 (2H, 2dq, CH$_3$C$\underline{H}_2$), 5.54 (1H, d, HCN), 6.69 (1H, bd, NH), 7.30–7.40 (5H, m, Ar-H); m/z (NH$_3$ DCI), 224 (M+H$^+$, 100%) 341 (M+NH4$^+$, 60%.).

b) N-[2'-Methyl-3'-mercaptopropionyl]-D-phenylglycine.

Prepared by Method C of Example 19 on N-[S-acetyl-2'-methyl-3'-mercaptopropionyl]-D-phenylglycine ethyl ester (0.15 mmol). This gave the title compound in 91% yield as a waxy solid, an approximately equimolar mixture of diastereoisomers.

$\nu_{max}$ (film) 1510, 1600, 1680, 2950 & 3300 cm$^{-1}$; $\delta_H$ (O=C(CD$_3$)$_2$)1.12, (3H, d, Me), 2.45–2.90 (3H, m, CH$_2$S, CHCO), 5.2 (2H, vbs, CO$_2$H, SH), 5.55, (1H, d, HCN), 7.30–7.50 (5H, m, Ar-H), 7.9 (1H, bd, NH).

Example 23

N-(4-Methyl-2-mercaptomethylpentanoyl]-D-phenylglycine.

a) S-Acetyl-4-Methyl-2-mercaptomethylpentanoic acid (Method A)

A solution of 2-isobutylacrylic acid methyl ester (W. H. Parsons, et al, *J. Med. Chem.*, 1988, 31(9), 1772; prepared by the method of Atta-ur-Rahman, et al, *Tetrahedron*, 1980, 36, 1063) (30 mmol) in ethanol (100 ml) was refluxed with a solution of potassium hydroxide (10 g) in water (5 ml) for 5 hours. The mixture was cooled, evaporated to low bulk and extracted with dichloromethane (10 ml). The aqueous phase was acidified with 5M HCl (20 ml) then extracted with dichloromethane (3×20 ml). These combined organic phases were dried (MgSO$_4$), filtered and evaporated.

The residue was dissolved in thiolacetic acid (10 ml) and heated to 80° C. for 3 days then cooled to RT and left for a further seven days. The solvent was evaporated and the residue partitioned between dichloromethane (3×10 ml) and saturated sodium hydrogen carbonate (500 ml). The aqueous phases was acidified with 5M aq. HCl and extracted with dichloromethane (3×50 ml). The combined organic phases were dried (MgSO$_4$), filtered and evaporated and the residue purified by flash chromatography (EtOAc) on silica gel to the title compound contaminated with 30% of the starting material.

$\delta_H$ (CDCl$_3$) 0.93, 0.97 (6H, d, (C$\underline{H}_3$)$_2$CH), 1.35–1.75 (3H, m, Me$_2$C$\underline{H}$CH$_2$), 2.35 (3H, s, Ac), 2.70 (1H, dddd, CHCO), 2.98, 3.14 (2H, 2dd, CH$_2$S).

b) N-[S-Acetyl-4-methyl-2-mercaptomethylpentanoyl]-D-phenylglycine methyl ester (Method B)

A stirred solution of the acid from Example 23a), (1.25 mmol) in dichloromethane (2 ml) at 0° C. was treated with 1-hydroxybenzotriazole (1.34 mmol) and N,N'-dicyclohexylcarbodiimide (1.30 mmol). After 2 minutes, D-phenylglycine methyl ester (1.5 mmol) obtained from the hydrochloride of Example 9b by treatment with triethylamine, was added and the mixture allowed to warm to 20° C. After 24 hours the mixture was filtered, 20 ml of dichloromethane added and the filtrate washed successively with 20 ml portions of saturated sodium hydrogen carbonate, water, and aqueous citric acid. The dichloromethane layer was dried (MgSO$_4$), filtered, and evaporated to afford a gum which was purified by flash chromatography (ethyl acetate-hexane) to give the title compound as a 1:1 mixture of diastereomers.

$\delta_H$ (CDCl$_3$) 0.80–0.95 (6H, m, $\underline{Me}_2$C), 1.30–1.70 (3H, m, Me$_2$C$\underline{H}$C$\underline{H}_2$), 2.26, 2.33 (3H, 2s, AcS), 2.45–2.55 (1H, m, CHCO), 2.90–3.05 (2H, m, CH$_2$S), 3.74 (3H, s, MeO), 5.40, 5.42 (1H, 2d, HCN), 6.68–6.90 (6H, m, Ar-H, NH). m/z (CI) 352 (M+H$^+$, 100%).

c) N-[4-Methyl-2-mercaptomethylpentanoyl]-D-phenylglycine

Prepared by Method C of Example 19 using N-[S-acetyl-4-methyl-2-mercaptomethylpentanoyl]-D-phenylglycine methyl ester. This gave the title compound as a clear oil, an approximately equimolar mixture of diastereoisomers.

$\nu_{max}$ (film) 1520, 1610, 1680, 2950 & 3300 cm$^{-1}$; $\delta_H$ (O=C(CD$_3$)$_2$) 0.75–1.00 (6H, m, $\underline{Me}_2$C), 1.20–1.80 (3H, m, Me$_2$C$\underline{H}$C$\underline{H}_2$), 2.45–2.95 (3H, m, CH$_2$S, CHCO), 5.30–5.50 (1H, bs, HCN), 6.75–7.00 (5H, m, Ar-H, 7.75 (1H, bs, NH).

Example 24

N-[2'-Benzyl-3'-mercaptopropionyl]-4-methylphenylglycine a) 2-Acetylthiomethyl-3-phenylpropanoic thiol acid 2-Acetylthiomethyl-3-phenylpropanoic acid [EP0361365] (1.185 g, 5 mmol) and 1,1-carbonyldiimidazole were dissolved in dichloromethane (20 ml). H$_2$S was bubbled through for 1 hour then the solvent evaporated and the residue dissolved in ether (50 ml). This solution was evaporated and the product partitioned between ether (3×50 ml) and 1M HCl (20 ml). The combined organic phases were dried (MgSO$_4$), filtered and evaporated to give the title compound in 89% yield as a colourless oil.

$\delta_H$ (CDCl$_3$) 2.31 (3H, s, CH$_3$CO), 2.85–3.20 (5H, m , PhC$\underline{H}_2$C$\underline{H}$C$\underline{H}_2$), 7.15–7.35 (5H, m Ar-H); m/z (NH$_3$ DCI), 272 (M+NH$_4^+$).

b) 2-Azido-2-[4-methylphenyl]acetic acid ethyl ester.

Potassium bis(trimethylsilyl)amide (12.32 ml, 6.16 mmol) was dissolved in anhydrous tetrahydrofuran (62 ml) and cooled to −78° C. The 4-methylphenylacetic acid ethyl ester (5 mmol, Aldrich) was dissolved in THF (19 ml) then slowly added to the potassium bis(trimethylsilyl)amide solution. After 30 minutes a cooled solution of 2,4,6-triisopropylsulfonyl azide (2.08 g, 6.72 mmol) in THF (22 ml) was slowly added. After a further 2 minutes, glacial acetic acid (1.47 ml) was introduced. The mixture was stood at room temperature for 16 hours then the solvents evaporated, and the residue partitioned between dichloromethane (3×50 ml) and brine (50 ml). The dichloromethane layers were combined, dried (MgSO$_4$) and the solvent evaporated. Purification was achieved by flash chromatography on silica gel (hexane-ether) to afford the title compound in 30% yield.

$\delta_H$ (CDCl$_3$) 1.30 (3H, t, C$\underline{H}_3$CH$_2$), 2.36 (3H, s, Ar-CH$_3$), 4.10–4.35 (2H, 2dq, CH$_3$C$\underline{H}_2$), 4.40 (1H, s, CHN), 7.1–7.3 (4H, abq, Ar-H); $\nu_{max}$ (KBr disc) 2105 (N$_3$), 1742 (CO), 1187, 1027 cm$^{-1}$; m/z (CI$^+$) 237 (M+NH4$^+$ 100%).

c) N-[S-Acetyl-2'-benzyl-3'-mercaptopropionyl]4-methylphenylglycine ethyl ester

The 2-Azido-2-(4-methylphenyl)acetic acid ethyl ester (0.45 mmol) and 2-acetylthiomethyl-3-phenylpropanoic thiol acid (0.23 g, 0.9 mmol) were dissolved in toluene (2 ml) and the mixture refluxed at 120° C. for 60 hours. The solvent was evaporated and the residue washed with brine (5 ml). The product was extracted into ethyl acetate (3×25 ml), evaporated and the product purified by flash chromatography on silica gel eluting with ethyl acetate-hexane to afford the racemic diastereomers of the title compound in 42% yield as an approximately equimolar mixture of isomers.

$\delta_H$ (CDCl$_3$) 1.20 (3H, t, C$\underline{H}_3$CH$_2$), 2.35, 2.37 (3H, 2s, AcS), 2.5–3.2 (SH, m, PhC$\underline{H}_2$C$\underline{H}$CH$_2$), 4.15 CH$_3$C$\underline{H}_2$), 5.38, 5.40 (1H, 2d, CHN), 6.25 (1H, bd, NH), 6.90–7.30 (9H, m, Ar-H); m/z (NH$_3$ DCI), 413 (M+NH$_4^+$).

d) N-[2'-Benzyl-3'-mereaptopropionyl]-4-methylphenylglycine

Prepared by Method C of Example 19 using N-[S-acetyl-2'-benzyl-3'-mercaptopropionyl]-4-methylphenylglycine ethyl ester. This gave the title compound as a clear oil, an approximately equimolar mixture of diastereoisomers.

$v_{max}$ (film) 3314 (OH), 3125–2926 (CH-Str), 25816 (SH), 1731 (C=O, Acid), 1651 (C=O, Amide), 1513–1425 (Ar-Str)

Example 25

N-[2'-Benzyl-3'-mercaptopropionyl]4-[1-methylisoiinidazolyl]glycine a) 4-[1-Methylisoimidazolyl]glycine methyl ester hydrochloride Prepared by Method A of Example 19 but using 4-(1-methylpyrazolyl)-glycine, prepared in turn from 4-formyl-1-methylpyrazole (Finar, et al, *J. Chem. Soc.*, 1957, 3314) via the hydrantoin using the Strecker synthesis. This gave the title compound as a white solid in quantitative yield.

δH (MeOD) 3.8 (3H, s, OMe), 4.1 (3H, s, NMe), 5.4 (1H, s), 7.2 (1H, d, NH), 8.0–8.25 (2H, m, Ar-H).

b) N-[S-Acetyl-2'-benzyl-3'-mercaptopropionyl]-4-[1-methylisoinidazolyl]glycine methyl ester Prepared by Method B of Example 19 but using 4-(1-methylisoimidazolyl)glycine methyl ester hydrochloride and triethylamine (101 mg, 1 mmol). This gave the title compound as a colourless oil in 33% yield, an approximately equimolar mixture of diastereoisomers.

δH (CDCl$_3$) 2.33, 2.47 (3H, 2s, AcS), 2.60–2.75 (1H, m, CH$_2$C$\underline{H}$CH$_2$), 2.83–3.14 (4H, m, C$\underline{H}_2$CHCH$_2$), 3.70, 3.75, 3.81, 3.86 (6H, 3s, OMe, NMe), 5.45–5.52 (1H, m, HCN), 6.15 (1H, bd, NH), 6.83 (0.5H, s, Ar-H 7.10–7.40 (6.5H, m, Ar-H); m/z (NH$_3$DCI) 390 (M+H' 100%).

c) N-[2'-Benzyl-3'-mercaptopropionyl]-4-[1-methylisoimidazolyl]glycine

Prepared by Method C of Example 19 but using, N-[S-acetyl-2'-benzyl-3'-mercaptopropionyl]-4-[1-methylisoimiazolyl]glycine methyl ester. This afforded the title compound as a clear oil, an approximately equimolar mixture of diastereoisomers.

$\delta_{max}$ (film) 3257 (OH), 3068–2939 (CH-Str), 2535 (SH), 1717 (C=O, Acid), 1631 (C=O, Amide), 1571–1451 (Ar-Str)

Example 26

N-[2'-Benzyl-3'-mercaptopropionyl]-3-methylphenylglycine (Isomer A and B)

a) 2-Azido-2-[3-methylphenyl]acetic acid ethyl ester

Prepared by the method of Example 24b) but on 2-(3-methylphenyl)acetic acid ethyl ester (Aldrich). This gave the title compound as-a clear oil in 90% yield.

$\delta_H$ (CDCl$_3$) 1.25 (3H, t, C$\underline{H}_3$CH$_2$), 2.38 (3H, s, $\underline{Me}$-Ar), 4.15–4.32 (2H, 2dq, CH$_3$C$\underline{H}_2$) 4.90 (1H, s, CHN), 7.15–7.33 (4H, m, Ar-H).

b) N-[S-Acetyl-2'-benzyl-3'-mercaptopropionyl]-3-methylphenylglycine ethyl ester A solution of 2-azido-2-(3-methylphenyl)acetic acid ethyl ester (0.5 mmol) in ethyl acetate (5 ml) with 10% palladium on carbon was hydrogenated for 2.5 hours. The catalyst was filtered off and the solvent evaporated to give 3-methylphenylglycine ethyl ester, $\delta_H$ (CDCl$_3$) 1.22 (3H, t, C$\underline{H}_3$CH$_2$), 2.32 (3H, s, $\underline{Me}$Ar), 4.12, 4.18 (2H 2dq, CH$_3$C $\underline{H}_3$), 4.53, (1H, s, HCN), 7.05–7.25 (4H, m, Ar-H) and used immediately in the next stage. 2-Acetylthiomethyl-3-phenylpropanoic acid [EP0361365]) (0.5 mmol) was added to a solution of dichloromethane (2 ml) and oxalyl chloride (0.25 ml). A drop of dimethylformnamide was introduced and the mixture stirred under argon, permitting, the escape of evolved gases. After 1 hour, the solvent was evaporated then coevaporated twice with dichloromethane. The amino acid was introduced followed by pyridine (2 ml) and triethylamine (0.5 mmol) and the mixture was stirred at RT for 1 hour. The mixture was evaporated then partitioned between 0.1M aq. HCl (25 ml) and ethyl acetate (3×25 ml). The combined, dried (MgSO$_4$) organic phase was evaporated and subjected to silica gel flash chromatography (hexane-ethyl acetate) to the title compound as a 1:1 mixture of separable diastereomers in 83% yield.

Less polar isomer: $\delta_H$ (CDCl$_3$) 1.12 (3H, t, C$\underline{H}_3$CH$_2$), 2.29, 2.31, (6H, s, eAr, AcS), 2.66 (1H, CH$_2$C$\underline{H}$CH$_2$), 2.80–3.13 (4H, C$\underline{H}_2$CHCH$_2$), 4.10, 4.20 (2H, 2dq, CH$_3$C$\underline{H}_2$) 5.41 (1H, d, HCN), 6.25 (1H, bd, NH), 6.70–7.25 (9H, m, Ar-H) More polar isomer: $\delta_H$(CDC$_3$) 1.11 (3H, t, C$\underline{H}_3$CH$_2$), 2.29, 2.33, (6H, s, $\underline{Me}$Ar, AcS), 2.70 (1H, CH$_2$C$\underline{H}$CH$_2$), 2.85–3.15 (4H, C$\underline{H}_2$CHCH$_2$), 4.05, 4.20 (2H, 2dq, CH$_3$C$\underline{H}_2$) 5.37 (1H, d, HCN), 6.30 (1H, bd, NH), 6.70–7.25 (9H, Ar-H).

c) N-[2'-Benzyl-3'-mercaptopropionyl]-3-methylphenylglycine

Prepared by Method C of Example19 but using the two diastereomeric N-[S-acetyl-2'-benzyl-3'-mercaptopropionyl]-3-methylphenylglycine ethyl esters separately. This procedure afforded the title compound as clear oils, pairs of racemates.

From less polar ester isomer A: $v_{max}$ (film) 3330 (OH), 3923 (CH-Str), 2535 (SH), 1731 (C=O, Acid), 1643 (C=O, Amide), 1530 (Ar-Str)

From more polar ester isomer B: $\delta_H$ (DMSO-d6) 2.25, (3H, s, MeAr), 2.35–3.00 (5H, m, CH$_2$CHCH$_2$), 5.30 (1H, d, HCN), 6.85–7.30 (9H, m, Ar-H), 8.70 (1H, d, NH), 12.5 (1H, bs, CO$_2$H); $v_{max}$ (CHCl$_3$) 3413 (OH), 3019 (CH-Str), 2530 (SH), 1722 (C=O, Acid), 1643 (C=O, Amide), 1496 (Ar-Str)

Example 27

N-[2'-Isobutyl-3'-mercaptobutanoyl]-D phenylglycine a) S-Acetyl-2-isobutyl-3-mercaptobutanoic acid Prepared by Method A of Example 23 but using 2-isobutyl-3-methylacrylic acid methyl ester [U.S. Pat. No. 4,595,700]. This gave the title compound as a yellow oil in 7% yield.

$\delta_H$ (CDCl$_3$) 0.82–0.95 (6H, m, (C$\underline{H}_3$)$_2$CH), 1.35–1.80 (6H, m, Me$_2$C$\underline{H}$C$\underline{H}_2$CHCHC$\underline{H}_3$), 2.35,2.36 (3H, 2s, Ac), 2.50–2.70 (1H, m, CHCO), 3.50–3.75 (1H, m, CHS).

b) N-[S-Acetyl-2'-isobutyl-3'-mercaptobutanoyl]-D-phenylglycine ethyl ester

Prepared by Method B of Example 23 but using S-acetyl-2-isobutyl-3-mercaptobutanoic acid and D-phenylglycine ethyl ester, obtained from the hydrochloride of Example 9c and triethylamine. This gave the title compound as a yellow oil in 20% yield and as an approximately 4:4:1:1 mixture of diastereomers.

δH(CDCl₃) 0.78–0.93 (6H, m, Me₂C), 1.20–1.80 (9H, m, Me₂CHCH₂CHCHCH₃, OCH₂CH₃), 2.27, 2.29, 2.32 (3H, 3s, 4×AcS), 2.40–2.60 (1H, m, CHCO), 3.60–3.85 (1H, m, CHS), 4.054.25 (3H, m, OCH₂CH₃), 5.5–5.62 (1H, m, HCN), 6.55, 6.68, 6.72, 6.79 (1H, m, NH), 7.30–7.30 (5H, m, Ar-H).

c) N-[2'-Isobutyl-3'-mercaptobutanoyl]-D-phenylglycine

Prepared by Method C of Example 19 but using N-[S-acetyl-2'-isobutyl-3'-mercaptobutanoyl]-D-phenylglycine ethyl ester. This afforded the title compound as a clear oil, an approximately 1:1:4:4 mixture of diastereoisomers.

$\delta_H$, (DMSO-d6) 0.75–0.90 (6H, m, Me₂C), 1.10–1.60 (6H, m, Me₂CHCH₂CHCHCH₃), 2.25–3.0 (2H, m, CHCO, CHS), 5.30–5.40 (1H, m, HCN), 7.3–7.4 (5H, m, Ar-H), 8.60–8.80 (1H, m, NH), 12.7 (1H, bs, CO₂H); $v_{max}$ (CHCl₃) 3280 (OH), 3018 (CH-Str), 2530 (SH), 1725 (C=O, Acid), 1640 (C=C, Amide), 1498 (Ar-Str).

Example 28

N-[2'Benzyl-3'-mercaptopropionyl]-N-methyl-phenylglycine (Isomers A and B)

a) N-Methyl-phenylglycine methyl ester hydrochloride

Prepared by Method A of Example 19 but using N-methyl-phenylglycine (prepared in turn from 2-chlorophenylacetic acid and methylamine) (3.5 g) methanol (20 ml) and acetyl chloride (40 ml) over 48 hours. The title compound was obtained in 94% yield, after trituration with methanol, as a white solid.

δH (CD₃OD) 2.62, (3H, s, MeN), 3.80 (3H, s, MeO), 5.18 (1H, s, HCN), 7.50–7.55 (5H, m, Ar-H).

b) N-[S-Acetyl-2'-benzyl-3'-mercaptopropionyl]-N-methyl-phenylglycine methyl ester Prepared by Method B of Example 19 but using N-methyl-phenylglycine methyl ester hydrochloride and additional triethylamine (1 mmol). The title compound was obtained as a 1:1 mixture of diastereomers, both colourless oils, in 42% yield. The diastereomers were separated.

Less polar isomer: $\delta_H$ (CDCl₃) 2.28 (3H, s, AcS), 2.54 (3H, s, MeN), 2.80–3.35 (5H, m, CH₂CHCH₂), 3.75 (3H, s, MeO), 6.43 (1H, s, HCN), 7.10–7.38 (10H, m, Ar-H).

More polar isomer: $\delta_H$ (CDCl₃) 2.38 (3H, s, AcS), 2.44 (3H, s, MeN), 2.85–3.40 (5H, m, CH₂CHCH₂), 3.78 (3H, s, MeO), 6.36 (1H, s, HCN), 6.80–6.88 (2H, m, Ar-H) 7.18–7.36 (8H, m, Ar-H).

c) N-[2'-Benzyl-3'-mercaptopropionyl]-N-methyl-phenylglycine

Prepared by Method C of Example 19 but using N-[S-acetyl-2'-benzyl-3'-mercaptopropionyl]-N-methyl-phenylglycine methyl ester. The isomers were purified by flash chromatography (CHCl₃-methanol) Each component was obtained as a white foam.

Less polar isomer A: $v_{max}$ (CHCl₃) 3410 (OH), 2930 (CH-Str), 2540 (SH), 1738 (C=O, Acid), 1602 (C=O, Amide), 1496 (Ar-Str).

More polar isomer B: $v_{max}$ (CHCl₃) 3420 (OH), 2930 (CH-Str), 2530 (SH), 1725 (C=O, Acid), 1601 (C=O, Amide), 1495 (Ar-Str).

Example 29

N-[2'-Benzyl-3'-mercaptopropionyl]-2-(4"-thiazolyl)glycine a) Ethyl 2-oxo-2-(4-thiazolyl)acetate A solution of amyl nitrite (5.4 ml) in tetrahydrofuran (45 ml) was added dropwise to a stirred solution of ethyl 2-amino-4-thiazoleglyoxylate (4.00 g) (Aldrich) in tetrahydrofuran (25 ml) at 60° C. When the addition was complete (1 h) the mixture was stirred at 60° C. for a further 2 h. The solvent was evaporated and the residue partitioned between ethyl acetate and sodium bicarbonate solution. The organic phase was washed with water and brine, dried over magnesium sulphate and evaporated. The product (2.54 g) was isolated by column chromatography of the residue using gradient elution (Kieselgel: 2:1 to 1:1 hexane:ethyl acetate). $v_{max}$ (CHCl₃)/cm⁻¹ 1737 and 1696. δ (250 MHz, CDCl₃), 1.42 (3H, t, J 7.11), 4.46 (2H, q, J 7.22), 8.84 (1H, J 1.95), 8.91 (1H, d, J 1.98).

b) Ethyl 2-hydroxyimino-2-(4thiazolyl)acetate

Hydroxylamine hydrochloride (1.37 g) was added to a stirred solution of ethyl 2-oxo-2-(4-thiazolyl)acetate (2.54 g) in ethanol (50 ml). The mixture was stirred for 3 h, the solvent was evaporated and the residue partitioned between ethyl acetate and sodium bicarbonate solution. The organic phase was washed with brine, dried over magnesium sulphate and evaporated. The residue was recrystallised from ethyl acetate to give the title oxime as a single isomer (1.315 g), m.p. 171–175° C.

$v_{max}$ (CHCl₃)/cm⁻¹ 1736. $\delta_H$(250 MHz, CD₃COCD₃) 1.35 (3H, t, J 6.95), 4.39 (2H, q, J 7.03), 7.98 (1H, d, J 1.97), 9.07 (1H, d, J 1.96), 11.05 (1H, s).

c) N-[2'-Benzyl-3'-acetylthiopropionyl]-2-(4"-thiazolyl)glycine ethyl ester

A stirred suspension of ethyl 2-hydroxyimino-2-(4-thiazolyl)acetate (400 mg) in 50% aqueous formic acid (4 ml) was cooled in an ice bath and zinc dust (300 mg) was added in small portions over one hour. The mixture was stirred at 0° C. for 3–5 h and then the solid was filtered off and washed with 50% formic acid. The combined filtrates were evaporated and the residue stirred with water and chloroform. The aqueous phase was neutralised with potassium carbonate and extracted with four portions of chloroform. The combined extracts were washed with brine, dried over magnesium sulphate and evaporated to ca: 1 ml. The residue was dissolved in dichloromethane (5 ml). Meanwhile, oxalyl chloride (0.1 ml) was added to a stirred solution of 2-acetylthiomethyl-3-phenylpropanoic acid [EP0361365] (238 mg) in dichloromethane (10 ml). Dimethylformamide (1 drop) was added and the mixture stirred for 1 h. The solvent was evaporated and the residue was triturated with chloroform and evaporated twice. The residue was dissolved in dichloromethane (2 ml) and added to the amine solution previously prepared. Triethylamine (0.28 ml) was added and the mixture stirred for 3 h. The mixture was washed successively with citric acid solution, water, sodium bicarbonate solution, water and brine. The solution was dried over magnesium sulphate and evaporated, and the product (304 mg) isolated by column chromatography of the residue as a mixture of isomers. (Kieselgel:1:1 ethyl acetate: hexane). $\delta_{max}$ (CHCl₃)/cm⁻¹ 3422, 1740, 1682.

$\delta_H$(250 MHz, CDCl₃) 1.19 and 1.22 (3H, two t's, J 7.17), 2.26 and 2.35 (3H, two s's), 2.66–3.14 (4H, m), 4.05–4.26 (2H, m,), 5.72 and 5.74 (1H, two d's, J 7.37), 6.60 and 6.69 (1H, two d's, J 7.33), 7.01–7.41 (6H, m,), 8.67 and 8.77 (1H, two d's, J 2.04), mlz (EI) 406 (M⁺).

d) N-[2'-Benzyl-3'-mercaptopropionyl]-2-(4"-thiazolyl)glycine

Sodium sulphide (491 mg) was added to a stirred solution of N-[2'-benzyl-3'-acetylthiopropionyl]-2-(4"-thiazolyl)glycine ethyl ester (227 mg) in a mixture of methanol (5 ml) and water (5 ml) under argon. After stirring for 15 min. the mixture was acidified with dilute hydrochloric acid (1 ml) and partitioned between ethyl acetate and water. The organic phase was washed with water and brine, dried over magnesium sulphate and evaporated. The product was purified by column chromatography (Kieselgel 20% methanol in chloroform with 0.1% acetic acid). The product was partitioned between ethyl acetate and sodium bicarbonate solution, the aqueous phase was acidified with dilute hydrochloric acid and extracted with ethyl acetate. The organic phase was washed with water and brine, dried over magnesium sulphate and evaporated to give the product (59 mg) as a mixture of isomers. (Found: M$^+$, 336.0598. $C_{15}H_{16}N_2O_3S_2$ requires 336.0602). $v_{max}$ (CHCl$_3$)/cm$^{-1}$ 3418, 3302, 1727 and 1672. $\delta_H$(250 MHz, CDCl$_3$), 1.45 and 1.69 (1H, two t's, J 7.88), 2.49–3.55 (4H, m), 5.86 and 5.87 (1H, two d's, J 7.65), 7.01–7.51 (7H, m), 8.72 and 8.80 (1H, two d's, J 2.00); m/z (EI) 336 (M$^+$).

Example 30

N-[2'-Benzyl-3'-mercaptopropionyl]-2-(2"-furanyl) glycine a) Methyl 2-oxo-2-(2-furanyl)acetate Methyl iodide (3.34 ml) was added to a stirred mixture of potassium carbonate (7.4 g) and furan α-oxoacetic acid (5 g) (Fluka) in dimethylformamide (70 ml). The mixture was stirred for 3 days and then partitioned between ethyl acetate and water. The organic phase was washed three times with water, then brine, dried over magnesium sulphate and evaporated. The product (2.1 g) was isolated by column chromatography using gradient elution (Kieselgel:3:1 going to 1:1 hexane:ethyl acetate. $\delta_H$ (250 MHz, CDCl$_3$), 3.96 (3H, s), 6.62–6.65 (1H, m), 7.75–7.78 (2H, m).

b) Methyl 2-hydroxyimino-2-(2-furanyl)acetate

Hydroxylamine hydrochloride (0.951 g) was added to a stirred solution of methyl 2-oxo-2-(2-furanyl)acetate (2.107 g) in methanol (30 ml). The mixture was stirred for 3 h, then the solvent was evaporated and the residue partitioned between ethyl acetate and water. The organic phase was washed with brine, dried over magnesium sulphate and evaporated. The title oxime was isolated by column chromatography of the residue using gradient elution (Kieselgel:3:1 to 1:1 hexane:ethyl acetate). (Found: M$^+$, 169.0378. $C_7H_7NO_4$ requires M, 169.0375). $v_{max}$ (CHCl$_3$/cm$^{-1}$ 3555, 3278 and 1739. $\delta_H$ (250 MHz, CDCl$_3$), 3.95 (3H, s), 6.57 (1H, dd, J 1.58 and 3.48), 7.45 (1H, d, J 3.22), 7.58 (1H, d, J 2.11), 9.75 (1H, br.s), m/z (EI) 169 (M$^+$).

c) N-[2'-Benzyl-3'-acetylthiopropionyl]-2-(2"-furanyl) glycine methyl ester

Zinc dust (300 mg) was added in portions to a stirred suspension of methyl 2-hydroxyimino-2-(2-furanyl)acetate (338 mg) in methanol (2 ml) and 50% aqueous formic acid (4 ml) at 0° C. When the addition was complete the mixture was stirred for a further 4 h at 0° C. The solid was filtered off and washed with 50% formic acid. The combined filtrates were evaporated and the residue stirred with chloroform and water. The aqueous phase was neutralised with potassium carbonate, the chloroform layer was separated and the aqueous phase extracted with four portions of chloroform. The combined organic extracts were washed with brine, dried over magnesium sulphate and evaporated to about 1 ml. The residue was dissolved in dichloromethane (10 ml). Meanwhile, oxalyl chloride (0.2 ml) was added to a stirred solution of 2-acetylthiomethyl-3-phenylpropanoic acid [EP0361365] (476 mg) in dichloromethane (10 ml). Dimethylformamide (1 drop) was added and the mixture stirred for 1 h. The solvent was evaporated and chloroform evaporated from the residue twice. The residue was dissolved in dichloromethane (2 ml) and added to a stirred solution of the amine previously prepared. Triethylamine (0.56 ml) was added and the mixture stirred for 2.5 h. The solution was washed with citric acid solution, water and brine, dried over magnesium sulphate and evaporated. The product (336 mg) was isolated by column chromatography of the residue using gradient elution (Kieselgel:2:1 to 1:1 hexane:ethyl acetate). $v_{max}$ (CHCl$_3$)/cm$^{-1}$ 3427, 1749 and 1682. $\delta_H$(250 MHz, CDCl$_3$), 2.29 and 2.35 (3H, two s's), 2.55–3.19 (5H, m), 3.70 and 3.74 (3H, two s's), 5.66 (1H, t, J 7.62), 6.12–6.35 (3H, m), 7.04–7.35 (6H, m); m/z (CI) 376 (M+H)$^+$.

d) N-[2'-Benzyl-3'-mercaptopropionyl]-2-(2"-furanyl) glycine

This compound was prepared from N-[2'-benzyl-31-acetylthiopropionyl]-2-(2"-furanyl)glycine methyl ester by the method described in Example 29d). (Found: M$^+$, 319.0878. $C_{16}H_{17}NO_4S$ requires 319.0878). $v_{max}$ (CHCl$_3$/cm$^{-1}$ 3431, 1725, 1677.

$\delta_H$(250 MHz, CHCl$_3$), 1.44 and 1.69 (1H, two t's), 2.45–3.05 (5H, m), 5.60–5.75 (1H, m), 6.12–6.88 (2H, m), 6.64 (1H, br.s), 7.04–7.26 (6H, m); m/z (EI) 319 (M$^+$).

Example 31

N-[2'-Benzyl-3'-mercaptopropionyl]-2-(2"-benzothienyl)glycine a) Ethyl 2-hydroxyimino-2-(2-benzothienyl)acetate n-Butyllithium (25 ml of 1.6N solution in hexanes) was added dropwise to a stirred solution of benzothiophene (5.36 g, Lancaster) in tetrahydrofuran (80 ml) under argon and cooled to −78° C. When the addition was complete the reaction was stirred at −78° C. for 10 min and then at room temperature for 20 min. The solution was then added via a cannula to a stirred solution of diethyl oxalate (11.68 g), cooled to −78° C. The mixture was stirred at −78° C. for 0.5 h and then at room temperature for 1 h. Acetic acid (1.5 ml) was added to the mixture which was then partitioned between ethyl acetate and water. The organic phase was washed three times with water, then with sodium bicarbonate solution, water and brine. The solution was dried over magnesium sulphate and evaporated. Column chromatography using gradient elution (Kieselgel:9:1 to 4:1 hexane:ethyl acetate) gave a mixture of ethyl-2-oxo-2-(2-benzothienyl) acetate and diethyl oxalate. The mixture was dissolved in ethanol (50 ml) and hydroxylamine hydrochloride (435 mg) was added. The mixture was stirred at room temperature for 3 days, then the solvent was evaporated and the residue partitioned between ethyl acetate and water. The organic phase was washed with water and brine, dried over magnesium sulphate and evaporated. The isomers of the title oxime were separated by column chromatography of the residue (Kieselgel:4:1 hexane:ethyl acetate). Isomer A: 887 mg, $v_{max}$ (CHCl$_3$)/cm$^{-1}$ 3564, 3309 and 1736. $\delta_H$(250 MHz; CDCl$_3$), 1.46 (3H, t, J 7.08), 4.53 (2H, q, J 7.11), 7.31–7.42 (2H, m), 7.46 (1H, s), 7.72–7.82 (2H, m), 8.83 (1H, s); m/z (EI) 249 (M$^+$). Isomer B: 624 mg, $v_{max}$ (CHCl$_3$)/cm$^{-1}$ 3545, 3249, 1731. $\delta_H$(250 MHz; CDCl$_3$), 1.49 (3H, t, J 7.19), 4.49 (2H, q, J 7.25), 7.35–7.47 (2H, m), 7.86–7.93 (2H, m), 8.40 (1H, s), 10.43 (1H, br.s); m/z (EI) 249 (M$^+$).

b) N-[2'-Benzyl-3'-acetylthiopropionyl]-2-(2"-benzothienyl)glycine ethyl ester

This compound was prepared from ethyl 2-hydroxyimino-2-(2-benzothienyl) acetate by the method described in Example 30c). (Found: M$^+$455.1230. $C_{24}H_{25}NO_4S_2$ requires 455.1225). $v_{max}$ (CHCl$_3$)/cm$^{-1}$ 3418, 1738 and 1682. $\delta_H$ (250 MHz, CDCl$_3$), 1.25 and 1.28 (3H, two t's, J 6.95), 2.29 and 2.36 (3H, two s's), 2.70–3.15 (5H, m), 4.08–4.31 (2H, m), 5.79–5.88 (1H, m), 6.37–6.44 (1H, m), 7.07–7.38 (8H, m) 7.65–7.79 (2H, m); m/z (EI) 455 (M$^+$).

c) N-[2'-Benzyl-3'-mercaptopropionyl]-2-(2"-benzothienyl) glycine

This compound was prepared from N-(2-benzyl-3-acetylpropionyl)-2-(2-benzothienyl)glycine ethyl ester by the method described in Example 29d), except that the eluent was 10% methanol in chloroform. (Found: M$^+$ 385.0811. $C_{20}H_{19}NO_3S_2$ requires 385.0806). $\nu_{max}$ (CHCl$_3$)/cm$^{-1}$ 3414, 3256, 1714 and 1635. 8H(250 MHz, CD$_3$SOCD$_3$), 2.20–3.03 (6H, m), 5.49–5.55 (1H, m), 7.17–7.35 (8H, m), 7.67–7.91 (2H, m), 8.64 and 8.72 (1H, two d's, J 7.24).

Example 32

N-[2'-Benzyl-3'-mercaptopropionyl]-2-(3"-furanyl) glycine a) 3-(2-Methylsulphinyl-2-methylthio)acetyl furan A stirred solution of ethyl 3-furoate (5 g) (Aldrich) and methyl methylsulphinylmethylsulphide (4 ml) in dimethylformamide (80 ml) under argon was cooled in an ice bath and sodium hydride (3.5 g of 50% oil dispersion) was added in small portions over 1 h. The mixture was stirred at room temperature for 6 h then acetic acid (5 ml) was added. The mixture was partitioned between ethyl acetate and water and filtered through Celite. The organic phase was washed four times with water, then brine, dried over magnesium sulphate and evaporated. The product (978 mg) was isolated by column chromatography of the residue (Kieselgel:ethyl acetate). (Found: M$^+$ 218.0068. $C_8H_{10}O_3S_2$ requires 218.0071). $\nu_{max}$(CHCl$_3$)/cm$^{-1}$ 1666. δH(250 MHz, CDCl$_3$), 2.22 and 2.29 (3H, two s's), 2.63 and 2.84 (3H, two s's), 4.80 and 4.82 (1H, two s's), 6.84 (1H, dd, J 1.86 and 2.88), 7.48 (1H, d, J 1.77), 8.19 and 8.22 (1H, two d's J 1.09); m/z (EI) 218 (M$^+$).

b) Methyl 2-oxo-2-(3-furanyl)acetate

A mixture of 3-(2-methylsulphinyl-2-methylthio)acetyl furan (976 mg) and potassium periodate (238 mg) in acetic acid (20 ml) was heated at 70° C. for 45 min. The mixture was cooled and the solvent evaporated. The residue was partitioned between ethyl acetate and water, and the organic phase washed with sodium thiosulphate solution, water and brine, dried over magnesium sulphate and evaporated. The residue was dissolved in methanol (5 ml) and added to a stirred solution of sodium (103 mg) in methanol (20 ml). After 20 mins the solution was partitioned between ethyl acetate and dilute hydrochloric acid. The organic phase was washed with water and brine, dried over magnesium sulphate and evaporated. The residue was stirred with potassium carbonate (614 mg) and methyl iodide (0.5 ml) in dimethylformamide (20 ml) for 17 h. The mixture was partitioned between ethyl acetate and water, the organic phase was washed three times with water, then brine, dried over magnesium sulphate and evaporated. The product (138 mg) was isolated by column chromatography of the residue (Kieselgel:3:1 hexane:ethyl acetate).

$\nu_{max}$ (CHCl$_3$)/cm$^{-1}$ 1736, 1683. δ$_H$(250 MHz, CDCl$_3$), 3.95 (3H, s), 6.91 (1H, dd, J 0.68 and 1.91), 7.48 (1H, t, J 1.80), 8.56 (1H, d, J 1.31).

c) Methyl 2-hydroxyimino-2-(3-furanyl)acetate

Hydroxylamine hydrochloride (70 mg) was added to a stirred solution of methyl 2-oxo-2-(3-furanyl)acetate (138 mg) in methanol (5 ml). After 6 h a further portion of hydroxylamine hydrochloride (60 mg) was added and the mixture stirred for 3 days. The solvent was evaporated and the residue partitioned between ethyl acetate and water. The organic phase was washed with water and brine, dried over magnesium sulphate and evaporated. The product (131 mg) was isolated by column chromatography of the residue (Kieselgel:3:2 hexane:ethyl acetate).

$\nu_{max}$ (CHCl$_3$)/cm$^{-1}$ 3263, 1735. δ$_H$(250 MHz, CDCl$_3$), 3.94 (3H, s), 7.15 (1H, d, J 1.91), 7.47 (1H, t, J 1.68), 8.48 (1H, d, J 1.24), 10.26 (1H, br.s).

d) N-[2'-Benzyl-3'-acetylthiopropionyl]-2-(3"-furanyl) glycine methyl ester

This compound was prepared from methyl 2-hydroxyimino-2-(3-furanyl)acetate by the method described in Example 30c), except the eluent used was 3:1 going to 1:1 hexane:ethyl acetate. (Found: M$^+$ 375.1140. $C_{19}H_{21}NO_5S$ requires 375.1140).

$\nu_{max}$ (CHCl$_3$)/cm$^{-1}$ 3424, 1745, 1682. δ$_H$(250 MHz, CDCl$_3$), 2.32 and 2.36 (3H, two s's), 2.61–3.20 (5H, m), 3.70 and 3.75 (3H, two s's), 5.46 and 5.48 (1H, two d's, J 7.13), 6.06 and 6.32 (1H, two s's), 6.13 (1H, d, J 7.32), 6.96–7.43 (7H, m); m/z (EI) 375 (M$^+$).

e) N-[2'-Benzyl-3'-mercaptopropionyl]-2-(3"-furanyl) glycine

This compound was prepared from N-[2'-benzyl-3'-acetylthiopropionyl]-2-(3"-furanyl)glycine methyl ester by the method described in Example 29d), except that the eluent used was 10% methanol in chloroform. (Found: M$^+$ 319.0878. $C_{16}H_{14}NO_4S$ requires 319.0878). $\nu_{max}$ (CHCl$_3$)/cm$^{-1}$ 3428, 1725 and 1675. δ$_H$(250 MHz, CDCl$_3$), 1.49 and 1.70 (1H, two t's, J 8.15), 2.50–2.99 (5H, m), 5.45 and 5.52 (1H, two d's, J 6.97), 6.10 and 6.36 (1H, two s's), 6.40 (1H, s), 7.09–7.46 (7H, m); m/z (EI) 319 (M$^+$).

Example 33

N-[2'-Benzyl-3'-mercaptopropionyl]-2.(1"-naphthyl) glycine a) Methyl 2-oxo-2-(1naphthyl)acetate Methyl 1-naphthyl acetate was prepared from methyl 1-naphthyl acetic acid (Aldrich) and methyl iodide in dimethylformamide in the presence of potassium carbonate, by the method of Example 34a). A mixture of methyl 1-naphthyl acetate (2.00 g) and selenium dioxide (1.12 g) was heated at 190° C. for 1.5 h. The mixture was cooled and stirred with ethyl acetate. The solid was filtered off and washed with ethyl acetate. The combined filtrates were washed with sodium bicarbonate solution, water and brine. The solution was dried over magnesium sulphate and evaporated. The product (1.806 g) was isolated by column chromatography of the residue (Kieselgel:3:1 hexane:ethyl acetate). (Found: M$^+$ 214.0630. $C_{13}H_{10}O_3$ requires 214.0630).

$\nu_{max}$ (CHCl$_3$)/cm$^{-1}$ 1738, 1680. δ$_H$(250 MHz, CDCl$_3$) 4.02 (3H, s), 7.53–7.74 (3H, m), 7.91–8.00 (2H, m), 8.13 (1H, d, J 8.25), 9.04 (1H, d, J 8.08); m/z (EI) 214 (M$^+$).

b) Methyl 2-hydroxyimino-2-(1-naphthyl)acetate

Hydroxylamine hydrochloride (834 mg) was added to a stirred solution of methyl 2-oxo-2-(1-naphthyl)acetate (1.72 g) in methanol. The mixture was left overnight then the solvent was evaporated and the residue partitioned between ethyl acetate and water. The organic phase was washed with water and brine, dried over magnesium sulphate and evaporated. The title oxime (828 mg) was obtained by recrystallisation of the residue from ethyl acetate/hexane. (Found: M$^+$ 229.0743. $C_{13}H_{11}NO_3$ requires 229.0739). $\nu_{max}$ (CHCl$_3$) 3311, 1725. δ$_H$(250 MHz, CDCl$_3$), 3.84 (3H, s), 7.43 (1H, dd, J 1.21 and 7.12), 7.46–7.64 (4H, m), 7.89–7.97 (2H, m); m/z (EI) 229 (M$^+$).

c) N-[2'-Benzyl-3'-acetylthiopropionyl]-2-(1"-naphthyl) glycine methyl ester

Prepared from methyl 2-hydroxyimino-2-(1-naphthyl) acetate by the procedure described in Example 30c), except that the eluent used was 3:1 to 1:1 hexane:ethyl acetate. δ$_H$(250 MHz, CDCl$_3$), 2.10 and 2.34 (3H, two s's), 2.59–3.22 (5H, m), 3.68 and 3.70 (3H, two s's), 6.23–6.31 (2H, m), 6.90–6.94 (3H, m), 7.14–7.57 (7H, m), 7.86–8.14 (2H, m); m/z (EI) 435 (M$^+$).

d) N-[2'-Benzyl-3'-mercaptopropionyl]-2-(1"-naphthyl)glycine

This compound was prepared from N-[2'-benzyl-3'-acetylthiopropionyl]-2-(1"-naphthyl)glycine methyl ester by the procedure described in Example 32e). (Found: M$^+$ 379.1248. $C_{22}H_{21}NO_3S$ requires 379.1242). $v_{max}$ (CHCl$_3$)/cm$^{-1}$ 3428, 3297, 1718, 1651. $\delta_H$(250 MHz, CD$_3$SOCD$_3$), 2.00–2.98 (6H, m), 5.86 and 5.91 (1H, two d's J 7.08), 7.07–7.55 (9H, m), 7.78–7.92 (2H, m), 8.10–8.28 (1H, m), 8.50 and 8.62 (1H, two d's, J 6.98); m/z (EI) 379 (M$^+$).

Example 34

N-[2'-Benzyl-3'-mercaptopropionyl]-2-(4"-biphenyl)glycine a) Methyl 4biphenylacetate Methyl iodide (0.75 ml) was added to a stirred mixture of 4-biphenylacetic acid (2.12 g) (Lancaster) and potassium carbonate (1.38 g) in dimethylformamide (25 ml) and the mixture left overnight. The mixture was partitioned between ethyl acetate and water, the organic phase was washed five times with water, then brine, dried over magnesium sulphate and evaporated. The product (2.1 g) was isolated by column chromatography of the residue (Kieselgel:3:1 hexane:ethyl acetate).

$v_{max}$ (CHCl$_3$)/cm$^{-1}$ 1735. $\delta$H(250 MHz, CDCl$_3$), 3.69 (2H, s), 3.73 (3H, s), 7.32–7.49 (5H, m), 7.55–7.62 (4H, m).

b) Methyl 2-oxo-2-(4-biphenyl)acetate

This compound was prepared from methyl 4-biphenyl acetate by the procedure described in Example 33a). (Found: M$^+$ 240.0786. $C_{15}H_{12}O_3$ requires 240.0786).

$v_{max}$ (CHCl$_3$)/cm$^{-1}$ 1738, 1683, 1602. $\delta_H$(250 MHz, CDCl$_3$), 4.01 (3H, s), 7.40–7.53 (3H, m), 7.62–7.67 (2H, m), 7.72–7.77 (2H, m), 8.08–8.14 (2H, m); m/z (EI) 240 (M$^+$).

c) Methyl 2-hydroxyimino-2-(4-biphenyl)acetate

A solution of methyl 2-oxo-2-(4-biphenyl)acetate (1.22 g) and hydroxylamine hydrochloride (706 mg) in methanol (20 ml) was allowed to stand overnight. The solvent was evaporated and the residue partitioned between ethyl acetate and water. The organic phase was washed with water and brine, dried over magnesium sulphate and evaporated. The title oxime (800 mg) was obtained by recrystallisation of the residue from ethyl acetate. $v_{max}$ (nujol)/cm$^{-1}$ 3216 and 1736. 6 (250 MHz, CD$_3$SOCD$_3$), 3.78 (3H, s), 7.36–7.54 (5H, m), 7.69–7.74 (4H, m), 12.55 (1H, s).

d) N-[2'-Benzyl-3'-acetylthiopropionyl]-2-(4"-biphenyl)glycine methyl ester

Prepared from methyl 2-hydroxyimino-2-(4-biphenyl)acetate by the procedure described in Example 30c), except that the eluent used was 3:1 to 1:1 hexane:ethyl acetate. (Found: M$^+$ 461.1651. $C_{27}H_{27}NO_4S$ requires 461.1661). $v_{max}$ (CHCl$_3$)/cm$^{-1}$ 3420, 1740 and 1682. $\delta_H$(250 MHz, CDCl$_3$), 2.30 and 2.37 (3H, two s's), 2.64–3.15 (5H, m), 3.69 and 3.73 (3H, two s's), 5.48 and 5.54 (1H, two d's J 7.05), 6.35–6.40 (1H, m), 6.84–7.59 (14H, m); m/z (EI) 461 (M$^+$).

e) N-[2'-Benzyl-3'-mercaptopropionyl]-2-(4"-biphenyl)glycine

This compound was prepared from N-[2'-benzyl-3'-acetylthiopropionyl]-2-($^{4"}$-biphenyl)glycine methyl ester by the procedure described in Example 32e).

$v_{max}$ (CHCl$_3$)/cm$^{-1}$ 3413, 3283, 1653 and 1620. $\delta_H$(250 MHz, CD$_3$SOCD$_3$), 2.10–3.00 (6H, m), 5.04 (1H, d, J 6.55), 7.16–7.63 (14H, m), 8.09 and 8.24 (1H, two d's, J 6.5); m/z (CI) 423 (M+NH$_4$)$^+$.

Example 35

N-[2'-Benzyl-3'-mercaptopropionyl]-2-(4"-isopropylphenyl)-glycine a) Methyl 4-isopropylphenylacetate Prepared from 4-isopropylphenylacetic acid (Lancaster) by the method described in Example 34a). $v_{max}$ (CHCl$_3$)/cm–1 1735. $\delta_H$(250 MHz, CDCl$_3$), 1.24 (6H, d, J 6.96), 2.90 (1H, heptet, J 6.93), 3.60 (2H, s), 3.69 (3H, s), 7.16–7.24 (5H, m).

b) Methyl 2-oxo-2-(4-isopropylphenyl)acetate

Prepared from methyl 4-isopropylphenylacetate by the method described in Example 33a), except that the eluent used was 4:1 hexane:ethyl acetate and the product contained starting material. $\delta_H$(250 MHz, CDCl$_3$), 1.28 (6H, d, J 6.87), 2.99 (1H, heptet), 3.98 (3H, s), 7.37 (2H, d, J 8.25), 7.95 (2H, d, J 8.33).

c) Methyl 2-hydroxyimino-2-(4isopropylphenyl)acetate

Hydroxylamine hydrochloride (0.87 g) was added to a stirred solution of the previously obtained mixture of methyl 2-oxo-2-(4-isopropyl-phenyl)acetate and methyl 4-isopropylphenyl acetate (1.29 g) in methanol (20 ml). When the solid had dissolved the mixture was left overnight. The solvent was evaporated and the residue partitioned between ethyl acetate and water, the organic phase was washed with water and brine, dried over magnesium sulphate and evaporated. The product (307 mg) was obtained by column chromatography of the residue using gradient elution (Kieselgel 3:1 to 1:1 hexane:ethyl acetate). $v_{max}$ (CHCl$^3$)/cm$^{-1}$ 3568, 3295 and 1738. $\delta_H$(250 MHz, CDCl$_3$), 1.28 (6H, d, J 6.87), 2.95 (1H, heptet, J 6.92), 3.88 (3H, s), 7.32 (2H, dd, J 1.81 and 6.47), 7.47 (2H, dd, J 1.83 and 6.65), 9.59 (1H, s).

d) N-[21-Benzyl-3'-acetylthiopropionyl]-2-(4"-isopropylphenyl)glycine methyl ester Prepared from methyl 2-hydroxyimino-2-(4-isopropylphenyl)acetate by the procedure described in Example 30c) except that the eluent used was 3:1 going to 1:1 hexane:ethyl acetate. (Found: M$^+$ 427.1816. $C_{24}H_{29}NO_4S$ requires 427.1817).

$v_{max}$ (CHCl$_3$)/cm$^{-1}$ 3422, 1740 and 1681. $\delta_H$(250 MHz, CDCl$_3$), 1.21–1.25 (6H, m), 2.28 and 2.35 (3H, two s's), 2.59–3.19 (6H, m), 3.66 and 3.70 (3H, two s's), 5.41 and 5.46 (1H, two d's, J 6.85), 6.22–6.28 (1H, m), 6.94–7.33 (9H, m); m/z (CI) 428 (M+H)$^+$.

e) N-[2'-Benzyl-3'-mercaptopropionyl]-2-(4"-isopropylphenyl)glycine

Prepared from N-[2'-benzyl-3'-acetylthiopropionyl]-2-(4"-isopropylphenyl)glycine methyl ester by the procedure described in Example 32e). (Found: M$^+$ 371.1549. $C_{21}H_{25}NO_3S$ requires 371.1555). $v_{max}$ (CHCl$_3$)/cm$^{-1}$ 3427, 3292, 2562, 1720 and 1652.

$\delta_H$(250 MHz, CD$_3$SOCD$_3$), 1.177 and 1.184 (6H, two d's, J 6.88), 2.05–2.94 (7H, m), 5.13 and 5.19 (1H, two d's, J 7.17), 7.07–7.33 (9H, m), 8.41 and 8.49 (1H, two d's, 6.85); m/z (EI) 371 (M$^+$).

Example 36

N-[2'-Benzyl-3'-mercaptopropionyl]-2-(3"-benzothienyl)glycine a) Methyl 2-oxo-2-(3-benzothienyl)acetate A mixture of methyl 2-(3-benzothienyl)acetate (2.26 g), (J. Chem. Soc., Perkin Trans. 1, 1983, (5), 909–14) and selenium dioxide (1.34 g) was heated to 160° C. for 2 h. The mixture was cooled and triturated with ethyl acetate. The solid was filtered off and washed with ethyl acetate. The combined filtrates were washed with sodium bicarbonate solution, water and brine, dried over magnesium sulphate and evaporated. The product (0.79 g) was isolated by column chromatography of the residue (Kieselgel:4:1 hexane:ethyl acetate as eluent). $v_{max}$ (CHCl$_3$)/cm$^{-1}$ 1736 and 1668.

$\delta_H$(250 MHz, CDCl$_3$) 4.00 (3H, s), 7.44–7.59 (2H, m), 7.90 (1H, dd, J 1.16 and 7.70), 8.72 (1H, dd, J 1.16 and 7.51), 8.94 (1H, s).

b) Methyl 2-hydroxyimino-2-(3-benzothienyl)acetate

Hydroxylamine hydrochloride (503 mg) was added to a stirred solution of methyl 2-oxo-2-(3-benzothienyl)acetate (790 mg) in methanol (30 ml). When all the solid had dissolved the mixture was allowed to stand overnight. The solvent was evaporated and the residue partitioned between ethyl acetace and water. The organic phase was washed with water and brine, dried over magnesium sulphate and evaporated. The title oxime (622 mg) was isolated as a mixture of isomers by column chromatography of the residue (Kieselgel: 3:1 going to 1:1 hexane:ethyl acetate. $v_{max}$ (CHCl$^3$)/cm$^{-1}$ 3568, 3296, 1737. $\delta_H$(250 MHz, CDCl$_3$), 3.90 and 4.00 (3H, two s's), 7.37–7.59 (2H, m), 7.61 and 7.77 (1H, two s's), 8.30 and 9.15 (1H, two broad s's), 8.43–8.47 (1H, m); m/z (EI) 235 (M$^+$).

c) N-[2'-Benzyl-3'-acetylthiopropionyl]-2-(3"-benzothienyl) glycine methyl ester Prepared from methyl 2-hydroxyimino-2-(3-benzothienyl)acetate by the procedure described in Example 30c), except that the eluent used was 3:1 to 1: 1 hexane:ethyl acetate. (Found: M$^+$ 441.1072. C$_{23}$H$_{23}$NO$_4$S$_2$ requires 441.1069). $v_{max}$ (CHCl$_3$)/cm$^{-1}$ 3429, 1742, 1681. $\delta_H$(250 MHz, CDCl$_3$), 2.14 and 2.35 (3H, two s's), 2.59–3.22 (5H, m), 3.69 and 3.72 (3H, two s's), 5.92 (1H, d, J 7.45), 6.26 (1H, d, J 7.38), 6.95–7.01 (3H, m), 7.20–7.40 (5H, m), 7.65–7.88 (2H, m); m/z (EI) 441 (M$^+$).

d) N-[2'-Benzyl-3'-mereaptopropionyl]-2-(3"-benzothienyl) glycine

Prepared from N-[2'-benzyl-3'-acetylthiopropionyl]-2-(3"-benzothienyl)glycine methyl ester by the procedure described in Example 32e).

$v_{max}$ (CHCl$_3$)/cm$^{-1}$ 3405, 3291, 1650 and 1605. $\delta_H$(250 MHz, CD$_3$SOCD$_3$), 2.05–3.00 (6H, m), 5.41 and 5.46 (1H, two d's, J 7.17), 6.96–7.50 (8H, m), 7.88–8.10 (2H, m), 8.24 and 8.38 (1H, two d's, J 7.30); m/z (CI) 403 (M+NH$_4$)$^+$.

Example 37

N-[(R)- and N-[(S)-2'-Mercaptomethyl-4'-phenylbutanoyl]-D-phenylglycine a) Diethyl 2-phenylethylmalonate A solution of diethyl malonate (6.07 ml, 40 mmol) in dimethyl formamide (60 ml) at 0° C. was treated portionwise with sodium hydride (1.6 g, 40 mmol, 60% dispersion in oil) and stirred for 0.25 h. 2-Phenylethyl bromide (5.48 ml, 40 mmol) in dimethylformarnmide (30 ml) was added dropwise. The mixture was warmed to room temperature and stirred for 1 h. The mixture was diluted with diethyl ether (300 ml), washed with water (4×200 ml), saturated brine (100 ml), dried (MgSO$_4$) and evaporated. Flash chromatography on silica, eluting with 1% ethyl acetate in hexane, gave the title compound as a colourless oil (7.55 g, 71%); $v_{max}$ (CH$_2$Cl$_2$), 1726 cm$^{-1}$;

$\delta_H$(CDCl$_3$), 1.27 (6H, t, J 7 Hz, 2×CH$_3$), 2.21 (2H, m, CH$_2$), 2.68 (2H, m, CH$_2$), 3.34 (1H, t, J 7.6 Hz, CH), 4.18 (4H, q, J 7 Hz, 2×OCH$_2$), 7.25 (5H, m, Ph). EIMS M$^+$ 264, DCIMS+265.

b) 2-Phenylethylmalonic Acid

A mixture of diethyl 2-phenylethylmalonate (3.61 g) and potassium hydroxide (1.69 g, 2.5 eq) in water (15 ml) was refluxed for 2 h and cooled to room temperature. The solution was washed with diethyl ether (2×10 ml) and then acidified to pH 2 (5M hydrochloric acid). The aqueous phase was extracted with diethyl ether (2×20 ml). The combined extracts were washed with water (2×20 ml), saturated brine (20 ml), dried (MgSO$_4$) and evaporated to give the title compound as a white solid (1.85 g, 65%); $v_{max}$ (KBr) 3080(br), 1705 cm$^{-1}$; $\delta_H$[(CD$_3$)$_2$CO], 2.18 (2H, m, CH$_2$), 2.70 (2H, m, CH$_2$), 3.40 (1H, t, J 7.4 Hz, CH), 7.25 (5H, m, Ph). DCIMS MNH$_4^+$ 226.

c) 2-Acetylthiomethyl-4phenylbutanoic Acid

A mixture of 2-phenylethylmalonic acid (1.8 g), 40% aqueous dimethylamine (1.08 ml, 1 eq) and 37% aqueous formaldehyde (0.64 ml, 1 eq) in water (10 ml) was stirred at room temperature overnight. After cooling at 0° C. the solid was filtered off, washed with water and dried. The white solid was heated at 170° C. for 10 minutes and cooled to room temperature. The resulting gum was dissolved in ethyl acetate (20 ml), washed with 10% potassium hydrogen sulphate solution (10 ml), water (2×10 ml), saturated brine (10 ml), dried (MgSO$_4$) and evaporated to give crude 2-methylene4-phenylbutanoic acid. $\delta_H$(CDCl$_3$) 2.55–2.90 (4H, m, 2×CH$_2$), 5.65, 6.85 (2H, 2×s,

7.25 (5H, m, Ph). The solid was dissolved in thioacetic acid (1 ml) and heated at 100° C. for 1 hour. After evaporation the gum was dissolved in ethyl acetate (10 ml) and extracted with saturated sodium hydrogen carbonate solution (2×10 ml). The combined extracts were washed with ethyl acetate (2×10 ml) and acidified with 10% potassium hydrogen sulphate solution (pH 3). The aqueous layer was extracted with ethyl acetate (2×10 ml) and the combined extracts washed with water (2×10 ml), dried (MgSO$_4$) and evaporated to yield the title compound as a yellow oil (0.52 g, 24%); $\delta_H$(CDCl$_3$) 2.00 (2H, m, CH$_2$), 2.71 (3H, m, CH$_2$, CH), 3.14 (2H, m, CH$_2$), 7.24 (5H, m, Ph). EIMS M$^+$ 252 DCIMS MNH$_4^+$ 270.

d) N-[2'-Acetylthiomethyl-4'-phenylbutanoyl]-D-phenylglycine

2-Acetylthiomethyl4-phenylbutanoic acid (513 mg, 2.03 mmol) in dichloromethane (20 ml) at room temperature was treated with oxalyl chloride (0.5 ml) followed by dimethylformnamide (1 drop). After 45 minutes the solution was evaporated and then re-evaporated from toluene (2×10 ml). The acid chloride was used to acylate (D)-phenylglycine as described in the method of Example 9h). Work-up and careful chromatography on silica, eluting with mixtures of methanol and dichloromethane allowed separation of the two diastereomers of the title compound:

(Isomer A), N-[(R)-2'-acetylthiomethyl-4'-phenylbutanoyl]-D-phenylglycine (170 mg, 22%); $\delta_H$[(CD$_3$)$_2$SO] 1.81 (2H, m, CH$_2$), 2.28 (3H, s, COCH$_3$), 2.65 (3H, m, CH, CH$_2$), 3.02 (2H, m, CH$_2$), 5.32 (1H, d, J 7.0 Hz, α-CH), 7.10–7.50 (10H, m, 2×Ph), 8.75 (1H, d, J 7.0 Hz, NH), DCIMS MH$^+$ 386 MNH$_4^+$ 403.

(Isomer B), N-[(S)-2'-Acetylthiomethyl-4'-phenylbutanoyl]-D-phenylglycine (170 mg, 22%); $\delta_H$[(CD$_3$)$_2$SO] 1.71 (2H, m, CH$_2$), 2.32 (3H, s, COCH$_3$), 2.34–2.76 (3H, m, CH, CH$_2$), 3.02 (2H, m, CH$_2$), 5.22 (1H, d, J 7.1 Hz. α-CH), 7.01–7.46 (10H, m, 2×Ph), 8.49 (1H, d, J 7.1 Hz, NH). DCIMS MH$^+$ 386, MNH$_4^+$ 403.

e) N-[(R)-2'-Mercaptomethyl-4'-phenylbutanoyl]-D-phenylglycine

N-[(R)-2'-Acetylthiomethyl-4'-phenylbutanoyl]-D-phenylglycine (150 mg) was deacylated as described in the method of Example 9k) to give the 2'(R)-isomer of the title compound (111 mg, 83%); $\nu_{max}$ (CH$_2$Cl$_2$) 3418, 1654, 1620 and 1497 cm$^{-1}$; $\delta_H$ [(CD$_3$)$_2$SO] 1.75 (2H, m, CH$_2$), 2.10 (1H, bt, SH), 2.60 (5H, m, 2×CH$_2$, CH), 5.18 (1H, d, J 7.1 Hz, α-CH), 7.10–7.50 (10H, m, 2×Ph), 8.31 (1H, d, J 7.1 Hz, NH).

Electrospray [M-H]$^-$ 342.

f) N-[(S)-2'-Mercaptomethyl-4'-phenylbutanoyl]-D-phenylglycine

N-[(S)-2'-Acetylthiomethyl-4'-phenylbutanoyl]-D-phenylglycine (140 mg) was deacetylated as described in the method of Example 9k) to give the $^2$'(S)-isomer of the title compound (84 mg, 67%); $\delta_H$[(CD$_3$)$_2$SO] 1.70 (2H, m, CH$_2$), 2.25–2.75 (6H, m, 2×CH$_2$, CH, SH), 5.11 (1H, d, J 6.9 Hz, α-CH), 7.0–7.5 (10H, 2×Ph), 8.24 (1H, d, J 6.9 Hz, NH). Electrospray MS [M-H]$^-$ 342.

Example 38

N-[(R)- and N-[(S)-2'-Mercaptomethyl-5'-phenylpentanoyl]-D-phenylglycine a) Diethyl 3-phenylpropylmalonate An ice-cold solution of diethyl malonate (5.81 ml, 40 mmol) in dimethylformamide (60 ml) was treated portionwise with sodium hydride (1.6 g, 40 mmol 60% dispersion in oil). After 0.25 h 3-phenylpropylbromide (6.71 ml, 44 mmol) was added and the reaction stirred overnight at room temperature. Work-up and chromatography as described in Example 37a) gave the title compound as a colourless oil (10.8 g, 97%);

$\nu_{max}$ (CH$_2$Cl$_2$) 2960 (br), 1750 (br) and 1457 cm$^{-1}$; $\delta_H$(CDCl$_3$) 1.26 (6H, t, J 7 Hz, 2×CH$_3$), 1.68 (2H, m, CH$_2$), 1.95 (2H, m, CH$_2$), 2.65 (2H, t, J 7.6 Hz, CH$_2$), 4.19 (4H, q, J 7 Hz, 2×OCH$_2$), 7.23 (5H, m, Ph), EIMS M$^+$ 278, DCIMS MH$_4$$^+$ 279, MNH$_4$$^+$ 296.

b) 3-Phenylpropylmalonic Acid

A mixture of diethyl 3-phenylpropylmalonate (5.5 g) and potassium hydroxide (2.8 g, 2.5 eq) in ethanol (20 ml) and water (30 ml) was refluxed for 5 hours. Work-up as described in Example 37b) gave the title compound (4.3 g, 98%); $\nu_{max}$ (CH$_2$Cl$_2$) 2940 (br), 1727 and 1413cm$^{-1}$; $\delta_H$(CDCl$_3$) 1.73 (2H, m, CH$_2$), 2.00 (2H, m, CH$_2$), 2.66 (2H, t, J 7.5 Hz, CH$_2$), 3.44 (1H, t, J 6.8 Hz, CH), 6.84 (2H, bs, 2×CO$_2$H), 7.26 (5H, m, Ph). EIMS M$^+$ 222, DCIMS MNH$_4$$^+$ 240.

c) 2-Acetylthiomethyl-5-phenylpentanoic Acid

3-Phenylpropylmalonic acid (6.14 g) was converted to 2-methylene-5-phenylpentanoic acid (2.1 g, 40%) by the method described in Example 37c).

$\delta_H$(CDCl$_3$) 1.88 (2H, m, CH$_2$), 2.37 (2H, t, J 7.6 Hz, CH$_2$), 2.67 (2H, t, J 7.6 Hz, CH$_2$), 5.68 and 6.33 (2H, 2×s,)

7.26 (5H, m, Ph). The solid was dissolved in thioacetic acid (5 ml) and heated at 100° C. for 2 hours. Evaporated to give the title compound (2.9 g, 100%); $\delta_H$(CDCl$_4$) 1.71 (4H, m, 2×CH$_2$), 2.33 (3H, s, COCH$_3$), 2.64 (3H, m, CH, CH$_2$), 3.08 (2H, m, CH$_2$), 7.27 (5H, m, Ph).

d) N-[2'-Acetylthiomethyl-5'-phenylpentanoyl]-D-phenylglycine

2-Acetylthiomethyl-5-phenylpentanoic acid (756 mg) was converted to the acid chloride as described in Example 37d). This was used to acylate D-phenylglycine as described in the method of Example 9 h) to give the two separated diastereomers.

(Isomer A), N-[(R)-2'-Acetylthiomethyl-5'-phenylpentanoyl]-D-phenylglycine (298 mg, 31%). $\delta_H$[(CD$_3$)$_2$SO] 1.35–1.72 (4H, m, 2×CH$_2$), 2.26 (3H, s, COCH$_3$), 2.37–3.00 (5H, m, 2×CH$_2$, CH), 5.31 (1H, d, J 7.1 Hz, α-CH), 7.0–7.5 (10H, m, Ph), 8.74 (1H, d, J 7.1 Hz, NH). EIMS MH$^+$ 400 DCIMS MH$^+$ 400.

(Isomer B), N-[(5)-2'-Acetylthiomethyl-5'-phenylpentanoy]-D-phenylglycine (150 mg, 16%). $\delta_H$[(CD$_3$)$_2$SO] 1.41 (4H, m, 2×CH$_2$), 2.32 (3H, s, COCH$_3$), 2.38–3.00 (5H, m, 2×CH$_2$, CH), 5.18 (1H, d, J 7.4 Hz, α-CH), 7.0–7.5 (10H, m, Ph), 8.48 (1H, d, J 7.4 Hz, NH). EIMS MH$^+$ 400, DCIMS MH$^+$ 400.

e) N-[(R-2'-Mercaptomethyl-5'-phenvipentanoyl]-D-phenylglycine

N-[(R)-2'-Acetylthiomethyl-5'-phenylpentanoyl]-D-phenylglycine (280 mg) was deacetylated as described in the method of Example 9k) to give the title compound (95 mg, 38%). $\nu_{max}$ (CH$_2$Cl$_2$) 1662 and 1620 cm$^{-1}$. $\delta_H$[(CD$_3$)$_2$SO] 1.53 (4H, m, 2×CH$_2$), 2.04 (1H, bt, J 7.5 Hz, SH), 2.51 (5H, m, 2×CH$_2$, CH), 5.10 (1H, d, J 7.0 Hz, α-CH), 7.03–7.50 (10H, m, Ph),8.24 (1H, d, J 7.0 Hz, NH). EIMS M$^+$ 357, DCIMS MH$^+$ 358, MNH$_4$$^+$ 375.

f) N-[(S)-2'-Mercaptomethyl-5'-phenylpentanoyl]-D-phenylglycine

N-[(S)-2'-Acetylthiomethyl-5'-phenylpentanoyl]-D-phenylglycine (140 mg) who deacetylated as described in the method of Example 9k) to give the title compound (62 mg, 49%). $\delta_H$[(CD$_3$)$_2$SO] 1.48 (4H, m, 2×CH$_2$), 2.25 (1H, br, SH), 2.55 (5H, m, 2×CH$_2$, CH), 5.09 (1H, d, J 7.0 Hz, α-CH), 7.02–7.48 (10H, m, Ph), 8.28 (1H, d, J 7 Hz, NH). EIMS M$^+$ 357, DCIMS MH$^+$ 358.

Example 39

N-[2'-Mercaptomethyl-6'-phenylhexanoyl]-D-phenylglycine a) Diethyl 4phenylbutylmalonate 4-Phenylbutyl chloride (5.48 g) was converted to the title compound (5.8 g, 64%) as described in Example 38a), except that the reaction was heated at 70° C. for 48 hours.

$\nu_{max}$ (CH$_2$Cl,) 2936, 1725 and 1180 cm$^-$; $\delta_H$(CDCl$_3$) 1.24 (6H, t, J 7.2 Hz, 2×CH$_3$), 1.37 (2H, m, CH$_2$), 1.66 (2H, m, CH$_2$), 1.92 (2H, m, CH$_2$), 2.62 (2H, t, J 7.6 Hz, CH$_2$), 3.31 (1H, t, J 7.5 Hz, CH), 4.17 (4H, q, J 7.2 Hz, 2×OCH$_2$), 7.24 (5H, m, Ph). EIMS M$^+$ 292, DCIMS MH$^+$ 293.

b) 4-Phenylbutylmalonic Acid

Diethyl 4-phenylbutylmalonate (5.5 g) was converted to the title compound (4.2 g, 94%) by the method described in Example 37b). $\nu_{max}$ (KBr) 3022 (br), 1696 and 1423 cm$^{-1}$. $\delta_H$(CD$_3$OD) [(CD$_3$)$_2$CO] 1.42 (2H, m, CH$_2$), 1.68 (2H, m, CH$_2$), 1,90 (2H, m, CH$_2$), 2.64 (2H, t, J 7.5 Hz, CH$_2$), 3.38 (1H, t, J 7.4 Hz, CH), 7.22 (5H, m, Ph). EIMS M$^+$ 236, DCIMS MNH$_4$$^+$ 254.

c) 2-Acetylthiomethyl-6-phenylhexanoic Acid

4-Phenylbutylmalonic acid (4.1 g) was converted to 2-methylene-6-phenyl-hexanoic acid (2.0 g, 56%) by the method described in Example 37c). $\delta_H$(CDCl$_3$) 1.61 (4H, m, 2×CH$_2$), 2.35 (2H, t, J 7.0 Hz, CH$_2$), 2.65 (2H, t, J 7.2 Hz, CH$_2$), 5.65, 6.31 (2H 2×s,

7.25 (5H, m, Ph). The solid was converted to the title compound (3.0 g, 100%) by the method described in Example 38c). $\delta_H$(CDCl$_3$) 1.36–1.80 (6H, m, 3×CH$_2$), 2.37 (3H, s, COCH$_3$), 2.50–2.70 (3H, m, CH$_2$CH), 3.08 (2H, m, CH$_2$), 7.23 (5H, m, Ph).

d) N-(2'-Acetylthiomethyl-6'-phenylhexanoyl)-D-phenylglycine

2-Acetylthiomethyl-6-phenylhexanoic acid (1.18 g) was converted to the acid chloride as described in Example 37d). This was used to acylate D-phenylglycine as described in the method of Example 9h) to give the title compound (670 g, 40%).

$\delta_H$[(CD$_3$)$_2$SO] 1.05–1.68 (6H, m, 3×CH$_2$), 2.26, 2.32 (3H, 2×s, COCH$_3$), 2.35–3.05 (5H, m, 2×CH$_2$, CH), 5.32 (0.5H, d, J 7.3 Hz, α-CH), 5.38 (0.5H, d, J 7.8 Hz, α-CH), 7.05–7.50 (10H, m, Ph), 8.72 (0.5H, d, J 7.3 Hz, NH), 8.80 (0.5H, d, J 7.8 Hz, NH).

e) N-(2'-Mercaptomethyl-6'-phenylhexanoyl)-D-phenylglycine

N-(2'-Acetylthiomethyl-6'-phenylhexanoyl)-D-phenylglycine (660 mg) was deacetylated as described in the method of Example 9k) to give the title compound (206 mg, 35%). $\delta_H$[(CD$_3$)$_2$SO] 1.00–1.68 (6H, m, 3×CH$_2$), 2.02 (0.5H, bt, SH), 2.20 (0.5H, bt, SH), 2.35–2.68 (5H, m, 2×CH$_2$, CH), 5.38 (0.5H, d, J 7.4 Hz, α-CH), 5.39 (0.5H, d, J 7.5 Hz, α-CH), 7.10–7.50 (10H, m, Ph), 8.70 (0.5H, d, J 7.5 Hz, NH), 8.78 (0.5H, d, J 7.4 Hz, NH). Electrospray MS MH$^+$ 372.

Example 40

N-[(R)- and N-[(S)-2'-Mercaptomethyl-7'-phenylheptanoyl]-D-phenylglycine a) Diethyl 5-phenylpentylmalonate 5-Phenylpentyl chloride (4.5 g) was converted to the title compound (3.67 g, 47%) as described in Example 38a), except that the reaction was heated at 70° C. for 20 hours.

$\nu_{max}$ (CH$_2$Cl$_2$) 2934, 1724 and 1180 cm$^{-1}$. $\delta_H$(CDCl$_3$) 1.24 (6H, t, J 7.2 Hz, 2×CH$_3$), 1.36 (4H, m, 2×CH), 1.62 (2H, m, CH$_2$), 1.87 (2H, m, CH$_2$), 2.60 (2H, t, J 7.5 Hz, CH$_2$), 3.31 (1H, t, J 7.5 Hz, CH), 4.17 (4H, q, J 7.2 Hz, 2×OCH$_2$), 7.23 (5H, m, Ph). EIMS M$^+$ 306, DCIMS MH$^+$ 307.

b) 5-Phenylpentylmalonic acid

Diethyl 5-phenylpentylmalonate (3.56 g) was converted to the title compound (2.9 g, 100%) by the method described in Example 38b). $\nu_{max}$ (KBr) 3022 (br), 1700 and 1418 cm$^{-1}$. $\delta_H$(CDCl$_3$) 1.32 (4H, m, 2×CH$_2$), 1.52 (2H, m, CH$_2$), 1.85 (2H, m, CH$_2$), 2.50 (2H, t, J 7.4 Hz, CH$_2$), 3.29 (1H, t, J 7.2 Hz, CH), 7.12 (5H, m, Ph). EIMS M$^+$ 250, DCIMS MNH$_4^+$ 268.

c) 2-Acetylthiomethyl-7-phenylheptanoic Acid

5-Phenylpentylmalonic acid (2.6 g) was converted to 2-methylene-7-phenylheptanoic acid (1.56 g, 70%) by the method described in Example 37c). $\delta_H$(CDCl$_3$) 1.20–1.75 (6H, m, 3×CH$_2$), 2.31 (2H, t, J 7.8 Hz, CH$_2$), 2.62 (2H, t, J 7.5 Hz, CH$_2$), 5.64, 6.28 (2H, 2×s,

7.25 (5H, m, Ph). The solid was converted to the title compound (2.0 g, 100%) by the method described in Example 38c). $\delta_H$(CDCl$_3$) 1.25–1.80 (8H, m, 4×CH$_2$), 2.35 (3H, s, COCH$_3$), 2.5–3.1 (5H, m, 2×CH$_2$, CH), 7.23 (5H, m, Ph).

d) N-[2'-Acetylthiomethyl-7'-phenylheptanoy]-3-D-phenylglycine

2-Acetylthiomethyl-7-phenyiheptanoic acid (1.27 g) was converted to the acid chloride as described in Example 37d). This was used to acylate D-phenylglycine as described in the method of Example 9h) to give the two diastereomers; N-[(R)-2'-acetylthiomethyl-7'-phenylheptanoyl]-D-phenylglycine (420 mg, 25%). $\delta_H$[(CD$_3$)$_2$SO] 1.05–1.70 (8H, m, 4×CH$_2$), 2.25 (3H, s, COCH$_3$), 2.40–3.03 (5H, m, 2×CH$_2$, CH), 5.32 (1H, d, J 7.4Hz, α-H), 7.10–7.50 (10H, m, Ph), 8.71 (1H, d, J 7.4 Hz, NH), 12.81 (1H, s, CO$_2$H), DCIMS MH$^+$ 428; N-[(S)-2'-acetylthiomethyl-7'-phenylheptanoyl]-D-phenylglycine (360 mg, 22%). $\delta_H$[(CD$_3$)$_2$SO] 1.05–1.55 (8H, m, 4×CH$_2$), 2.31 (3H, s, COCH$_3$), 2.42–2.69 (3H, m, CH$_2$CH), 2.92 (2H, m, CH$_2$), 5.13 (1H, d, J 7.4 Hz, α-H), 7.23 (10H, m, Ph), 8.33 (1H, d, J 7.4 Hz, NH). DCIMS MH$^+$ 428.

e) N-[(R)-2'-Mercaptomethyl-7'-phenylheptanoyl]-D-phenylglycine

N-[(R)-2'-Acetylthiomethyl-7'-phenylheptanoyl]-D-phenylglycine (400 mg) was deacetylated as described in the method of Example 9k) to give the title compound (240 g, 72%). $\delta_H$[(CD$_3$)2SO] 1.05–1.60 (8H, 4×CH$_2$), 1.96 (1H, bt, SH), 2.30–2.60 (5H, m, 2×CH$_2$, CH), 5.21 (1H, d, J 7.0 Hz, α-H), 7.01–7.45 (10H, m, Ph), 8.48 (1H, d, J 7.0 Hz, NH). DCIMS MH$^+$ 386.

f) N-[(S)-2'-Mercaptomethyl-7'-phenylheptanoyl]-D-phenylglycine

N-[(S)-2'-Acetylthiomethyl-7'-phenylheptanoyl)-D-phenylglycine (350 mg) was deacetylated as described in the method of Example 9k) to give the title compound (164 mg, 52%). $\delta_H$[(CD$_3$)$_2$SO] 1.05–1.60 (8H, m, 4×CH$_2$), 2.13–2.95 (6H, m, 2×CH$_2$, CH, SH), 5.08 (1H, d, J 7.0 Hz, α-H), 7.25 (10H, m, Ph), 8.18 (1H, d, J 7.0 Hz, NH). Electrospray MS [M+H]$^+$ 386.

Example 41

N-[2'-(Indan-1-yl)-3'-mercaptopropanoyl]-D-phenylglycine a) Diethyl indan-1-ylmalonate A mixture indan (6.11 ml, 50 mmol), N-bromosuccinimide (8.9 g, 50 mmol) and azo-iso-butyronitrile (10 mg) in carbon tetrachloride was refluxed under strong illumination for 1.25 h. Cooled in ice, filtered and evaporated, the crude 1-bromoindan was converted to the title compound (8.1 g, 59%) as described in Example 38a). $\nu_{max}$ (CH$_2$Cl$_2$) 1730 (b)cm$_{31\ 1}$. $\delta_H$(CDCl$_3$) 1.23 (6H, m, 2×CH$_3$), 2.00, 2.32 (2H, 2×m, CH$_2$), 2.91 (2H, m, CH$_2$), 3.58 (1H, d, J 8.8 Hz, CH), 3.92 (1H, m, CH), 7.18 (4H, m, Ar). EIMS M$^+$ 276, DCIMS MNH$_4^+$ 294.

b) Indan-1-ylmalonic acid

Diethyl indan-1-ylmalonate (7.74 g) was converted to the title compound (6.1 g, 98%) by the method described in Example 38b). $\nu_{max}$ (CH$_2$Cl$_2$) 2950 (br), 1731 (br)cm$^{-1}$.

$\delta_H$[(CD$_3$)$_2$CO] 2.02–2.43 (2H, m, CH$_2$), 2.73–3.10 (2H, m, CH,), 3.60 (1H, d, J 7.8 Hz), 3.85 (1H, m, CH), 7.19 (4H, m, Ar). EIMS M$^+$ 220 DCIMS MNH$_{4+}$ 238.

c) 3-Acetylthio-2-(indan-1-yl)propanoic Acid

Indan-1-ylmalonic acid (5.9 g) was converted to 2-(indan-1-yl)-acrylic acid (2.9 g, 58%) by the method described in Example 37c). $\nu_{max}$ (CH$_2$Cl$_2$) 2948 (br), 1696 cm$^{-1}$.

$\delta_H$(CDCl$_3$) 1.95, 2.51 (2H, 2×m, CH$_2$), 2.96 (2H, m, CH$_2$), 4.30 (1H, t, J 7.8 Hz, CH), 5.48, 6.42 (1H, 2×s,

7.20 (4H, m, Ar). EIMS M$^+$ 188. The solid (2.64 g) was converted to the title compound (3.7 g, 100%) by the method described in Example 37c). $\delta_H$(CDCl$_3$) 1.91–3.80 (11H, m, 3×CH$_2$, CH$_3$, 2×CH), 7.23 (4H, m, Ar).

d) N-[3'-Acetylthio-2'-(indan-1-yl)propanoyl]-D-phenylglycine

3-Acetylthio-2-(indan-1-yl)propanoic acid (1.53 g) was converted to the acid chloride as described in Example 37d). This was used to acylate D-phenylglycine as described in the method of Example 9h) to give the title compound (1.1 g, 48%).

$\delta_H$[(CD$_3$)$_2$SO] 1.81–3.48 (1H, m, 2×CH, 3×CH$_2$, CH$_3$), 5.38 (1H, m, α-H), 6.95–7.46 (9H, m, Ar), 8.82 (1H, m, NH), 12.88 (1H, bs, CO$_2$H), EIMS M$^+$ 397, DCIMS MH$^+$ 398.

e) N-[2'-(Indan-1-yl)-3'-mercaptopropanoyl]-D-phenylglycine

N-[3'-Acetylthio-2'-(indan-1-yl)propanoyl]-D-phenylglycine (1.1 g) was deacetylated as described in the method of Example 9k) to give the title compound (610 mg, 62%) as a mixture of four diastereomers in a ratio of 2.5:2.5: 1:1. $\nu_{max}$ (CH$_2$Cl$_2$) 3419, 2946 (br), 1722, 1674 and 1500 cm$^{-}$. $\delta_H$[(CD$_3$)$_2$SO] 1.75–3.62 (9H, m, 3×CH$_2$, 3×CH), 5.37 (1H, m, α-H), 6.99–7.48 (9H, m, Ar), 8.77 (1H, m, NH). EIMS M$^+$ 355. DCIMS MH$^+$ 356.

Example 42

N-[2'- and N-[(S)-2'-Mercaptomethyl-4'-phenoxybutanoyl]-D-phenylglycine a) Diethyl 2-phenoxyethylmalonate β-Bromophenetole (5.81 ml, 40 mmol) was converted to the title compound (10.3 g, 92%) by the method described in Example 37a). δ (CDCl$_3$) 1.26 (6H, t, J 7.1 Hz, 2×CH$_2$), 2.40 (2H, m, CH$_2$CH), 3.68 (1H, t, J 7.3 Hz, CH), 4.05 (2H, t, J 7.1 Hz, OCH$_2$), 6.90, 7.28 (5H, 2×m, Ph).

b) 2-Phenoxyethylmalonic acid

Diethyl 2-phenoxyethylmalonate (1 g) was treated with sodium hydroxide (285 mg, 2 eq) in ethanol (10 ml) and water (5 ml). After 16 h the solution was diluted with water (10 ml), washed with diethyl ether (3×20 ml), acidified to pH 2 (5M hydrochloric acid) and extracted with ethyl acetate (2×20 ml). The combined extracts were washed with water (3×20 ml), saturated brine (20 ml), dried (MgSO$_4$) and evaporated to yield the title compound (510 mg, 64%). $\nu_{max}$ (KBr) 2915 (br), 1730 and 1243 cm$^{-1}$. $\delta_H$[(CD$_3$)$_2$CO] 2.36 (2H, m, CH$_2$CH), 3.69 (1H, t, J 7.2 Hz, CH), 4.12 (2H, t, J 7.3 Hz, OCH$_2$), 6.94, 7.28 (5H, m, Ph). EIMS M$^+$ 224, DCIMS MNH$_4^+$ 242.

c) 2-Acetylthiomethyl-4-phenoxybutanoic Acid

2-Phenoxyethylmalonic acid (5.4 g) was converted to 2-methylene-4-phenoxybutanoic acid (2.8 g, 60%) by the method described in Example 37c). $\nu_{max}$ (CH$_2$Cl$_2$) 2937 (br), 1695, 1244 cm$^{-1}$. $\delta_H$(CDCl$_3$) 2.86 (2H, t, J 6.8 Hz, CH$_2$), 4.14 (2H, t, J 6.8 Hz, OCH$_2$), 5.88, 6.46 (2H, 2×d, J 1.0 Hz,

6.92, 7.31 '(5H, m, Ph). EIMS M$^+$ 192. The solid (2.6 g) was converted to the tite compound (3.6 g, 100%) by the method described in Example 38c). $\delta_H$(CDCl$_3$) 1.95–2.45 (5H, m, CH$_3$, CH$_2$), 2.95 (1H, m, CH), 3.20 (2H, m, CH$_2$), 4.09 (2H, m, OCH$_2$), 6.93, 7.31 (5H, m, Ph), inter alia.

d) N-[2'-Acetylthiomethyl-4'-phenoxybutanoyl]-D-phenylglycine

2-Acetylthiomethyl-4-phenoxybutanoic acid (1.6 g) was converted to the acid chloride as described in Example 37d). This was used to acylate D-phenylglycine as described in the method of Example 9h) to give the title compound (610 mg, 25%).

$\delta_H$[(CD$_3$)$_2$SO] 1.89 (2H, m, CH$_2$), 2.28, 2.34 (3H, 2×s, COCH$_3$), 2.73–3.15 (3H, m, CH$_2$ CH), 3.70–4.15 (2H, m, OCH$_2$), 5.30–5.36 (1H, 2×d, J 7.0, 7.6 Hz), 6.70–7.45 (10H, m, 2×Ph), 8.77, 8.83 (1H, 2×d, J 7.0, 7.6 Hz, NH), DCIMS MH$^+$ 402.

e) N-[2'-Mercaptomethyl-4'-phenoxybutanoyl]-D-phenylglycine

N-[2'-Acetylthiomethyl4'-phenoxybutanoyl]-D-phenylglycine (600 mg) was deacetylated as described in the method of Example 9k) to give a mixture of diastereomers from which N-[(S)-2'-mercaptomethyl-4-phenoxybutanoyl]-D-phenylglycine (120 mg, 22%) was isolated. $\nu_{max}$ (CH$_2$Cl$_2$) 3415, 2934, 1722, 1675 and 1498 cm$^{-1}$. $\delta_H$[(CD$_3$)$_2$SO] 1.92 (2H, m, CH$_2$), 2.32 (1H, br, SH), 2.71 (3H, m, CH$_2$, CH), 3.72 (2H, m, OCH$_2$), 5.21 (1H, d, J 7.1 Hz, α-H), 6.71–7.48 (10H, m, 2×Ph), 8.51 (1H, d, J 7.1 Hz, NH). EIMS M$^+$ 359 DCIMS MH$^+$ 360.

Example 43

N-[2'-Benzyl-3'-mercaptopropionyl]-2-(3"-thienyl) glycine a) N-[2'-Benzyl-3'-acetylthiopropionyl]-2-(3"-thienyl) glycine methyl ester Oxalyl chloride (0.05 ml) was added to a stirred solution of 2-acetylthiomethyl-3-phenylpropanoic acid [EP0361365] (119 mg) in dichloromethane (5 ml). Dimethylformamide (1 drop) was added and the mixture stirred at room temperature for 0.5 h and then at reflux for a further 0.5 h. The mixture was cooled and the solvent evaporated and chloroform was evaporated from the residue twice. The residue was dissolved in dichloromethane (5ml) and added to a stirred solution of 2-(3-thienyl)glycine methyl ester hydrochloride (Ger. Offen. DE 3,528,631: CA 106: P 133819c) (104 mg) and triethylamine (0.14 ml) in dichloromethane (5 ml). The mixture was stirred at room temperature for 2 h, then diluted with chloroform and washed successively with citric acid solution, water, sodium bicarbonate solution, water and brine, dried over magnesium sulphate and evaporated. The product (190 mg) was isolated by column chromatography of the residue using gradient elution (Kieselgel: 3:1 going to 1:1 hexane:ethyl acetate). $\nu_{max}$ (CHCl$_3$)/cm$^{-1}$ 3423, 1742, and 1681. $\delta_H$250 MHz, CDCl$_3$) 2.31 and 2:36 (3H, two s's), 2.56–3.14 (5H, m), 3.69 and 3.74 (3H, two s's), 5.60 (1H, t, J 6.64), 6.23 (2H, t, J 6.20), 6.74–6.77 (1H, m), 6.98–7.33 (7H, m).

b) N-[2'-Benzyl-3'-mercaptopropionyl]-2-(3"-thienyl)glycine

Water (2.6 ml) was added to a stirred solution of N-[2'-benzyl-3'-acetylthiopropionyl]-2-(3"-thienyl)glycine methyl ester (162 mg) in methanol (2.6 ml) under argon. Sodium sulphide nonahydrate (400 mg) was added and the mixture stirred for 20 min. Dilute hydrochloric acid (2 ml of 5N) was then added and the mixture partitioned between ethyl acetate and water. The organic phase was washed with water and brine, dried over magnesium sulphate and evaporated. The title product (102 mg) was isolated by column chromatography of the residue (Kieselgel: 10% methanol in chloroform). $\nu_{max}$ (CHCl$_3$)/cm$^{-1}$ 3411, 3290, 1646 (s), 1619. $\delta_H$(250 MHz, CDCl$_3$), 2.10–2.97 (6H, m), 5.14 and 5.19 (1H, two d's, J 7.51), 6.94–6.90 (1H, m), 7.15–7.40 (7H, m), 8.10 and 8.25 (1H, two d's. J 7.54); m/z (electrospray) 334 [M-H]$^-$.

Example 44

N-[2'-(1"-Mercaptoethyl)-4'-phenylbutanoyl]-D-phenylglycine a) (+/−) Triethyl 4-phenyl-2-phosphonoacetate A mixture of 2-bromoethylbenzene (5 ml, 36 mmol), potassium carbonate (8.28 g, 60 mmol), triethyl phosphonoacetate (6.71 ml, 30 mmol) and sodium iodide (2.25 g, 15 mmol) was stirred at 70° for 48 h. The reaction was diluted with ethyl acetate (60 ml), washed with water (4×40 ml), saturated brine (40 ml), dried (MgSO$_4$) and evaporated. Flash chromatography on silica eluting with 20% grading to 50% ethyl acetate in hexane gave the title compound (3.3 g, 34%); $\nu_{max}$ (CH$_2$Cl$_2$) 1732.5 cm$^{-1}$; $\delta_H$ (CDCl$_3$), 1.31 (9H, m, 3×CH$_3$), 2.10–3.10 (4H, m, 2×CH$_2$), 4.18 (6H, m, 2×OCH$_2$), 7.27 (5H, m, Ph); m/z (CI) 329 [M+H]$^+$.

b) Ethyl 2-(2'-phenylethyl)crotonate

A suspension of sodium hydride (0.45 g, 60% dispersion in oil) in dry tetrahydrofuran (20 ml) at rt was treated dropwise with a solution of Example 44a (2.93 g) in dry tetrahydrofuran (20 ml). The mixture was stirred 1 h and then acetaldehyde (0.75 ml) was added. Stirring was continued for 2 h, and the mixture was diluted with ethyl acetate (50 ml), washed with saturated ammonium chloride solution (20 ml), saturated brine (2×20 ml), dried (MgSO$_4$) and evaporated. Flash chromatography on silica eluting with 2% grading to 10% ethyl acetate in hexane gave the title compound as a 3:1 mixture of isomers, in favour of the trans-crotonate (1.4 g, 72%); $\nu_{max}$ (CH$_2$Cl$_2$) 1710 cm$^{-1}$; $\delta_H$ (CDCl$_3$) 1.33 (3H, m, CH$_3$), 1.63, 1.97 (3H, 2×d, J 7.1 Hz, CH$_3$CH=), 2.67 (4H, m, 2×CH$_2$), 4.22 (4H, m, OCH$_2$), 5.97, 6.89 (1H, 2×q, J 7.1 Hz, CH=), 7.25 (5H, m, Ph); m/z (EI) 218 (M$^+$).

c) 2-(2'-Phenylethyl)crotonic acid

A mixture of Example 44b (1.1 g) and sodium hydroxide (0.3 g) in ethanol (15 ml) and water (15 ml) was refluxed overnight and cooled to room temperature. The aqueous phase was washed with ether (3×20 ml) and acidified to pH2 (5M HCl). The aqueous was then extracted with further portions of ether (2×20 ml). The combined extracts were washed with water (2×20 ml), saturated brine (20 ml), dried (MgSO$_4$) and evaporated to yield the title compound (0.87 g, 91%); $\nu_{max}$ (CH$_2$Cl$_2$) 1683 cm$^{-1}$; $\delta_H$ (CDCl$_3$) 1.63, 2.04 (3H, 2×d J 7.3 Hz, CH$_3$CH=) 2.68 (4H, m, 2×CH$_2$), 6.12, 7.04 (1H, 2×q, J 7.3 Hz, CH=), 7.23 (5H, m, Ph); m/z (E1) 190 (M$^+$).

d) (R,S)-2-((R,S)-1'-Acetylthioethyl)-4-phenylbutanoic acid

A solution of Example 44c (800 mg) in thioacetic acid was heated at 100° C. for 5 h and evaporated to give the title compound (1.12 g, 100%); $\delta_H$ (CDCl$_3$) 1.23–2.80 (8H, m, 2×CH$_2$, CH, CH$_3$), 2.33–2.55 (3H, m, COCH$_3$), 3.88 (1H, m, CH), 7.23 (5H, m, Ph); m/z (EI), 266 (M$^+$).

e) N-[2'-(1"-Acetylthioethyl)-4'-phenylbutanoyl]-D-phenylglycine methyl ester

The acid of Example 44d (296 mg) was converted to the title compound (150 mg, 33%) by Method B of Example 23; $\delta_H$ (CDCl$_3$) 1.18–1.48 (3H, m, CH$_3$), 1.62–2.81 (6H, m, 2×CH$_2$, 2×CH), 2.25, 2.28, 2.30, 2.32 (3H, 4×s, COCH$_3$); n/z (EI), 414 [M+H]$^+$.

f) N-[2'-(1"-Mercaptoethyl)-4'-phenylbutanoyl]-D-phenylglycine

The title compound was prepared from Example 44e (120 mg) using Method C of Example 19 (66 mg, 64%). The compound was isolated as a 1:1:2:2 mixture of diastereomers; $\delta_H$[(CD$_3$)$_2$SO] 1.12–1.40 (3H, m, CH$_3$), 1.68–2.08 (2H, m, CH$_2$), 2.28–3.21 (4H, m, PhCH$_2$), 2×CH), 5.28 (1H, m, CH), 7.35 (10H, m, 2×Ph), 8.60 (1H, m, NH); m/z (EI), 357 (MH)$^+$.

Example 45

N-[3'-(3",4"-Dihydroxyphenyl)-(R,S)-2'-mercaptomethyl-propanoyl)-D-phenylglycine a) 3.4-Isopropylidenedioxytoluene A mixture of 4-methylcatechol (12.4 g, 0.1M), 2,2-dimethoxypropane (62 ml, 0.5M) and phosphorous pentoxide (100 mg) in toluene (250 ml) was refluxed under a Soxhlet extractor containing 4A molecular sieves for 4 h. Cooled to room temperature and washed with saturated sodium hydrogen carbonate solution (100 ml), dried (MgSO$_4$) and evaporated. The oil in hexane was filtered through silica to give the title compound (15.14 g, 92%); $\delta_H$ (CDCl$_3$) 1.66 (6H, s, 2×CH$_3$), 2.30 (3H, s, CH$_3$), 6.60 (3H, m, Ar); m/z (EI) 164 (M$^+$).

b) Diethyl 3,4-isopropylidenedioxybenzylmalonate

A solution of Example 45a (8.2 g) in carbon tetrachloride (100 ml) with N-bromosuccinimide (8.9 g) was reluxed under strong illumination for 1 h. Cooled in ice, filtered and evaporated to low volume (ca 20 ml). The crude bromide was converted to the title compound (10.14 g, 63%) by the method described in Example 37a; $\delta_H$ (CDCl$_3$) 1.15–1.35 (6H, m, 2×CH$_3$), 1.64, 1.65 (6H, 2×s, 2×CH$_3$), 3.10 (2H, d, J 7.8 Hz, CH$_2$), 3.57 (1H, t, J 7.8 Hz, CH), 4.08–4.85 (4H, m, 2×OCH$_2$), 6.60 (3H, m, Ar); m/z (ES+) 323 (MH$^+$).

c) 3,4-Isopropylidenedioxybenzylmalonic acid

Example 45b (4.8 g) was converted to the title compound by the method described in Example 37b (2.4 g, 61%); $\delta_H$ [(CD$_3$)$_2$CO] 1.63 (6H, s, 2×CH$_3$), 3.11 (2H, d, J 7.7 Hz, CH$_2$), 3.62 (1H, t, J 7.7 Hz, CH), 7.21 (3H, m, Ar); m/z (ES$^-$) 265 (M-H)$^-$ d) 2-Methylene-3-(3'4'-isopropylidenedioxyphenyl)propanoic acid Example 45c (2.3 g) was converted to the title compound (670 mg, 33%) by the method described in Example 37c; $\delta_H$ (CDCl$_3$) 1.68 (6H, s, 2×CH$_3$), 3.52 (2H, s, CH$_2$), 5.51, 6.68 (2H, 2×s, H$_2$C=), 6.62 (3H, m, Ar); m/z (ES$^-$), 233 (M-H)$^-$ e) N-(2-Methylene-3-(3',4'-isopropylidenedioxyphenyl)propanyl]-D-phenylglycine methyl ester Example 45d (416 mg) was converted to the acid chloride as described in the method of Example 37d. The acid chloride in dichloromethane (5 ml) was added dropwise to an ice-cold solution of D-phenylglycine methyl ester (358 mg) and triethylamine (0.6 ml) in dichloromethane (5 ml), allowed to gain room temperature and stirred for 1 h. The mixture was loaded directly onto a silica flash column and eluted with 10% grading to 30% ethyl acetate in hexane to give the title compound (547 mg, 81%); $\delta_H$ [(CD$_3$)$_2$CO]

1.63 (6H, 2×s, 2×CH$_3$), 3.53 (2H, s, CH$_2$), 3.68 (3H, s, CH$_3$), 5.38, 5.89 (2H, 2×s, H$_2$C=), 5.56 (1H, d, J 6.2 Hz, NH), 6.64 (3H, m, Ar), 7.33 (5H, m, Ph), 7.72 (1H, d, J 6.2 Hz, NH); m/z (ES$^+$) 382 (MH$^+$).

f) N-[3-(3',4'-Dihydroxyphenyl)-2-methyenepropanoyl]-D-phenylglycine

Example 45e (460 mg) in glacial acetic acid (15 ml) and water (5 ml) was refluxed for 3 h and evaporated. Redissolved in ethyl acetate (20 ml), washed with water (2×10 ml), saturated brine (10 ml), dried (MgSO$_4$) and evaporated. Flash chromatography on silica eluting with 35% grading to 40% ethyl acetate in hexane gave the title compound (356 mg, 86%); δ$_H$ (CDCl$_3$) 3.51 (2H, s, CH$_2$), 3.68 (3H, s, CH$_3$), 5.35, 5.88 (2H, 2×H, H$_2$C=, 5.52 (1H, d, J 7.0 Hz, CH), 6.15 (1H, bs, OH), 6.52–7.35 (10H, m, Ar, Ph, NH, OH); m/z (ES$^+$) 342 (MH$^+$).

g) N-[(R,S)-2-Acetylthiomethyl-3-(3,4-dihydroxyphenyl)propanoyl]-D-phenylglycine methyl ester A solution of Example 45f (290 mg) in thiolacetic acid (2 ml) was stood at room temperature for 3 h and evaporated. Flash choromatography on silica eluting 30% grading to 60% ethyl acetate in hexane gave the title compound (280 mg, 79%); δ$_H$ (CDCl$_3$) 2.28, 2.35 (3H, 2×s, COCH$_3$), 2.60–3.12 (5H, m, 2×CH$_2$, CH), 3.66, 3.69 (3H, 2×s, OCH$_3$), 5.45 (1H, m, CH), 6.40–7.40 (1H, m, NH, Ph, Ar, 2×OH); m/z (ES$^+$) 418 (MH$^+$).

h) N-[(R,S)-3-(3,4-Dihydroxyphenyl)-3-mercaptomethylpropanoyl]-D-phenylglycine

Example 45 g (245 mg) was deprotected as described by Method B of Example 23 to give the title compound (115 mg, 54%); δ$_H$ [(CD$_3$)$_2$SO] 2.35–3.15 (6H, m, 2×CH$_2$, CH, SH), 5.01 (1H, m, CH), 6.20–7.46 (1H, m, Ph, Ar, NH, 2×OH).

Example 46

N-[2'-Mercaptomethyl-4'-(4"-hydroxycarbonyl)phenylbutanoyl]-D-phenylglycuine a) 2-Bromomethylacrylic add benzhydryl ester A solution of diphenyldiazomethane in dichloromethane (50 ml) was slowly added to a stirred slurry of 2-bromomethylacrylic acid (Aldrich) (4.95 g), in dichloromethane (50 ml) at room temperature. After 1 hour, the solvent was evaporated and the residue subjected to chromatography on silica gel, eluting with a mixture of hexane and diethyl ether. This afforded 2-bromomethylacrylic acid benzhydryl ester in 67% yield as a colourless oil; δ$_H$ (CDCl$_3$) 4.24 (2H, s, CH$_2$Br), 6.02, 6.48 (2H, 2s, =CH$_2$), 7.07 (1H, s, CHPh$_2$), 7.25–7.45 (10H, m, Ar-H).

b) 2-(2'-(4"-Methoxycarbonylphenyl)ethyl)acrylic acid benzhydryl ester

A sample of zinc foil (0.125 mm thick, 520 mg) in dry THF under an argon atmosphere was treated with chlorotrimethylsilane (15 mg) then 1,2-dibromoethane (188 mg) and stirred for 15 minutes. The mixture was cooled to between 0 and 5° C. and methyl 4-bromomethylbenzoate (Aldrich) (1145 mg) introduced and the reaction was maintained at this temperature for two hours. A 2.5 ml aliquot of this mixture was then added to a solution of CuCN (180 mg) and LiCl (180 mg) in THF (2 ml) at −70° C. The mixture was warmed to 0° C. then evaporated, recooled to −78° C. and treated with a solution of Example 46a (662 mg) in dichloromethane (5 ml). The mixture was warmed to 0° C. and sonicated at this temperature for 1 hour, then partitioned between dichloromethane (3×20 ml) and saturated aqueous ammonium chloride (20 ml). The combined organic phases were dried (MgSO$_4$), filtered and evaporated to give an oil which crystallised from hexane at −20° C. to give the title compound (590 mg). δ$_H$ (CDCl$_3$) 2.67 (2H, dt, CH$_2$CH$_2$Ar), 2.85 (2H, t, CH$_2$CH$_2$Ar), 3.91 (3H, s, Me), 5.55, (1H, d, =CH, J=0.9 Hz), 6.31 (1H, s, =CH) 6.96 (1H, s, CHPh$_2$), 7.12 (2H, d, benzoate-H), 7.25–7.38 (10H, m, Ar-H), 7.94 (2H, d, benzoate-H).

c) N-[2'-(S-Acetylmercaptomethyl)-4'-(4"-methoxycarbonyl)phenylbutanoyl]-D-phenylglycine methyl ester A solution of Example 46b (100 mg) in thiolacetic acid (1 ml) was treated with trifluoroacetic acid (0.5 ml). After 16 hours at room temperature, the solvents were evaporated to give a yellow oil. This was dissolved in dichloromethane (2 ml) and treated with oxalyl chloride (1 ml) and ¼ drop of DMF. A rapid effervescence occurred and the mixture was stirred at RT for 3 hours then evaporated in vacuo and coevaporated with dichloromethane. The residue was dissolved in pyridine (5 ml) containing a suspension of D-phenylglycine hydrochloride methyl ester (1 g) and triethylamine (0.3 ml) was introduced. The reaction mixture was stirred at RT for 8 hours then evaporated and partitioned between dichloromethane (3×25 ml) and aqueous hydrochloric acid (0.1M, 100 ml). The combine organic phase was dried (MgSO$_4$), filtered, evaporated and the residue subjected to silica gel chromatography eluting with ethyl acetate and hexane to afford the title compound (104 mg) as two separate diastereoisomers.

Less polar isomer (49 mg): δH (CDCl$_3$) 1.7–2.1 (2H, m), 2.34 (3H, s, MeC=O), 2.4–3.2 (5H, m), 3.74 (3H, s, MeO-glycine), 3.89 (3H, s, MeO-benzoate), 5.60, (1H, d, HCN), 6.67 (1H, bd, NH), 7.09 (2H, d, benzoate-H), 7.25–7.38 (5H, m, Ar-H), 7.90 (2H, d, benzoate-H); m/z (CI$^+$ NH$_3$) 475 (M+NH$_4$+25%), 458 (M+H$^+$ 100%). More polar isomer (55 mg): δH (CDCl$_3$) 1.7–2.1 (2H, m), 2.27 (3H, s, MeC=O), 2.4–3.2 (5H, m), 3.75 (3H, s, MeO-glycine), 3.90 (3H, s, MeO-benzoate), 5.55, (1H, d, HCN), 6.48 (1H, bd, NH), 7.31 (2H, d, benzoate-H), 7.35–7.38 (5H, m, Ar-H), 7.97 (2H, d, benzoate-H); m/z (CI$^+$ NH$_3$) 475 (M+NH$_4^+$ 60%), 458 (M+H$^+$ 100%).

d) N-[2'-(Mercaptomethyl)-4'-(4"-hydroxycarbonyl)phenylbutanoyl]-D-phenylglycine Isomer A; A solution of the less polar isomer from Example 46c (40 mg) in degassed methanol was added to a solution of sodium sulfide nonahydrate (200 mg) in water (2 ml). The mixture was stirred for 90 minutes, poured into aqueous hydrochloric acid (0.1M, 30 ml) and extracted into ethyl acetate (3×20 ml). The combined organic phases were dried (MgSO$_4$), filtered and evaporated then freeze dried from 1,4-dioxane to give the title compound (29 mg) as a white foam. vmax (KBr disc) 3421, 2954, 1718, 1642 and 1521 cm$^{-1}$; δH (MeOD) 1.75–1.95 (2H, m), 2.50–2.95 (5H, m), 5.49 (1H, bs, HCN), 7.32–7.78 (7H, m, Ar-H), 7.95 (2H, d, benzoate-H); m/z (ESI+MeCN) 429 (M+MeCN+H$^+$ 100%), 242 (65%).

Isomer B; An identical procedure with the more polar ester isomer from Example 46d (45 mg) afforded the corresponding diasteromer of the title compound (33 mg) as a white foam. vmax (KBr disc) 3413, 2949, 1717, 1637 and 1529 cm$^{-1}$; δH (MeOD) 1.75–1.95 (2H, m), 2.50–2.95 (5H, m), 5.52 (1H, bs, HCN), 7.19 (2H, d, benzoate-H), 7.32–7.48 (7H, m, Ar-H), 7.88 (2H, d, benzoate-H); m/z (ESI+MeCN) 429 (M+MeCN+H$^+$ 100%), 277 (15%).

Example 47

N-[2'-Mercaptomethyl-4'-(2"-trifluoromethyl-6"-quinolin-6-yl)butanoyl)-D-phenylglycine a) 2-(2'-(2"-Trifluoromethylquinolin-6"-yl)ethyl)aciylic acid benzhydryl ester

Prepared by the method of Example 46b, but utilising 6-bromomethyl-2-trifluoromethylquinoline (1.1 g) in place of methyl 4-bromomethylbenzoate. The product was purified by flash chromatography to afford the title compound as a white solid (750 mg). δH (CDCl$_3$) 2.78, 3.02 (4H, 2t, CH$_2$CH$_2$), 5.29, 6.32 (2H, 2s, =CH$_2$), 6.98 (1H, s, CHPh$_2$), 7.25–7.40 (10H, m, Ph-H), 7.55–7.70 (3H, m, quinoline-H), 8.10–8.24 (2H, m, quinoline-H).

b) N-[2'-(S-Acetylmercaptomethyl)-4'-(2"-trifluoromethylquinolin-6"-yl)butanoyl]-D-phenylglycine methyl ester A solution of Example 47a (461 mg) in thiolacetic acid (0.5 ml) was treated with TFA (1 ml). after 16 hours, the mixture was warmed to 50° C. for 3 days, cooled and evaporated. The residue was washed with saturated aqueous sodium hydrogen carbonate to afford a yellow oil. This was dissolved in dichloromethane (5 ml) and treated with oxalyl chloride (5 ml) and DMF (1 drop). After 1 hour, the mixture was evaporated, dissolved in pyridine (15 ml) containing a suspension of phenylglycine methyl ester hydrochloride (2 g), triethylamine (3 ml) introduced and the resulting mixture stirred for 12 hours at room temperature. The solvents were evaporated and the residue partitioned between aqueous hydrochloric acid (0.5M, 100 ml) and ethyl acetate (3×100 ml). The combined organic phases were dried (MgSO$_4$), filtered and evaporated then subjected to flash chromatography (ethyl acetate—hexane) to give the title compound (90 mg) as two separate diasteroisomers in approximately 1:1 ratio.

Less polar isomer: νmax (film) 3350, 2940, 1744, 1695, 1657, 1511, 1342, 1179, 1136 and 1081 cm$^{-1}$; δH (CDCl$_3$) 1.8–2.2 (2H, m), 2.26 (3H, s, MeC=O), 2.33–2.45 (1H, m), 2.70–3.05 (4H, m), 3.76 (3H, m, MeO), 5.56 (1H, d, HCN), 6.47 (1H, bd, NH), 7.37 (5H, bs, Ph-H), 7.70–7.80 (3H, m, quinoline-H), 8.16, 8.32 (2H, 2d, quinoline-H); m/z (ES+) 519 (M+H$^+$ 100%).

More polar isomer: νmax (film) 3350, 2940, 1744, 1690, 1500, 1337, 1179, 1130 and 1071 cm$^{-1}$; δH (CDCl$_3$) 1.8–2.15 (2H, m), 2.34 (3H, s, MeC=O), 2.35–2.45 (1H, m), 2.60–3.20 (4H, m), 3.74 (3H, m, MeO), 5.61 (1H, d, HCN), 6.68 (1H, bd, NH), 7.41 (5H, bs, Ph-H), 7.45–7.72 (3H, m, quinoline-H), 8.09, 8.21 (2H, 2d, quinoline-H); m/z (ES+) 519 (M+H$^+$ 100%).

c) N-[2'-(Mercaptomethyl)-4'-(2"-trifluoromethylquinolin-6"-yl)butanoyl]-D-phenylglycine.

Isomer A; Prepared by the method of Example 46d, but using the less polar isomer of Example 47b (30 mg) as the starting material, the title compound was obtained as a gum.

δH (MeOD) 1.95–2.05 (1H, m), 2.55–2.95 (6H, m), 5.50 (1H, d, HCN), 7.25–8.10 (8H, m, Ar-H), 8.37, 8.51 (2H, 2d, quinoline-H).

Isomer B; The more polar isomer from Example 47b was treated likewise and gave a similar gum.

δH (MeOD) 1.95–2.05 (1H, m), 2.55–2.95 (6H, m), 5.40 (1H, d, HCN), 7.25–8.10 (8H, m, Ar-H), 8.41, 8.54 (2H, 2d, quinoline-H).

Example 48

N-[3-Mercaptobutanoyl]-D-phenylglycine a) N-Crotonyl-D-phenylglycine methyl ester

A solution of D-phenylglycine methyl ester hydrochloride (404 mg) in pyridine (10 ml) and triethylamine (400 mg) was cooled to 0° C. and treated to the dropwise addition of crotonyl chloride (202 mg) over 1 minute. The resulting orange suspension was stirred for two days at RT then evaporated, dissolved in ethyl acetate (50 ml) and washed successively with 1M aqueous hydrochloric acid (1M, 2×25 ml), water (10 ml) and saturated sodium hydrogen carbonate (10 ml). The ethyl acetate layer was dried (MgSO$_4$) filtered and evaporated then purified by silica gel flash chromatography (ethyl acetate-hexane) to give the title compound as a white solid in 42% yield. δH (CDCl$_3$) 1.85 (3H, dd, MeC), 3.74 (3H, s, MeO), 5.67 (1H, d, HCN), 5.87 (1H, 2d, =CHCO), 6.4 (1H, bd, NH), 6.88 (1H, dq, =CHMe), 7.30–7.36 (5H, m, Ar-H).

b) N-[3-S-Acetylmercaptobutanoyl]-D-phenylglycine methyl ester

A solution of Example 48a in thiolacetic acid (70 mg) was maintained at room temperature for 12 hours. The solvent was evaporated and the residue subjected to flash chromatography (ether-hexane) to obtain the title compound as a clear oil in 94% yield, an approximately 1:1 mixture of diastereoisomers. δH (CDCl$_3$) 1.32–1.36 (3H, m, MeCH), 2.26, 2.27 (3H, 2s, MeC=O), 2.40–2.65 (2H, 4dd, CH$_2$), 3.71 (3H, s, MeO), 3.78–3.91 (1H, m, SCH), 5.56, 5.57 (1H, 2d, HCN), 6.65, 6.71 (1H, 2bd, NH) 7.34 (5H, bs, Ar-H).

c) N-[3-Mercaptobutanoyl]-D-phenylglycine

Prepared by the method of Example 46d, but using Example 48b (50 mg) as the starting material, the title compound (43 mg) was obtained as a clear oil, an approximately 1:1 mixture of diastereomers. δH (CDCl$_3$) 1.26–1.36 (3H, m, MeCH), 1.75, 1.93 (1H, 2d, SH), 2.30–2.60 (2H, m, CH$_2$), 3.29–3.48 (1H, m, SCH), 5.56, 5.57 (1H, 2d, HCN), 6.87 (1H, bd, NH) 7.30–7.40 (δH, bs, Ar-H), 8.75 (1H, bs, CO$_2$H); m/z (ES$^+$) 254 (M+H$^+$ 100%), (ES$^-$) 252 (M-H$^-$ 50%), 208 (100%).

Example 49

N-[2-Benzyl-3-mercaptopentanoyl]-D-phenylglycine a) 1-Benzyl-1-(tertbutyloxycarbonyl) methylenetriphenylphosphorane

A slurry of tertbutyloxycarbonylmethylenetriphenylphosphonium bromide (4.57 g) caesium carbonate (6.5 g) and benzyl bromide (1.2 ml) in acetonitrile (50 ml) were stirred at room temperature for 18 hours, the mixture was partitioned between dichloromethane (3×100 ml) and 10% aqueous potassium carbonate (200 ml). The combined organic phases were dried (MgSO$_4$), filtered and evaporated. The residue was crystallised from ether-hexane to give the title compound as a yellow solid in 90% yield. δH (CDCl$_3$) 0.98 (9H, s, Me$_3$C), 3.36 (2H, d, CH$_2$), 6.91–7.10 (5H, m, Ar-H), 7.36–7.56 (15H, m, Ar-H).

b) 2-Benzyl-3-ethylacrylic acid tertbutyl ester

A solution of Example 49a (920 mg) in 1,2-dichloroethane (5 ml) was treated with propionaldehyde (174 mg). The mixture was heated to 62° C. for 16 hours then cooled, partitioned between brine (25 ml) and dichloromethane (3×25 ml), the organic phases combined, dried (MgSO$_4$), filtered and evaporated and the residue purified by flash chromatography (hexane-ether). The title compound was obtained in 47% yield as a clear oil. δH (CDCl$_3$) 1.06 (3H, m, CH$_2$CH$_3$), 1.38 (9H, s, Me$_3$C), 2.23 (2H, app.quint., CH$_2$CH$_3$), 3.63 (2H, s, CH$_2$Ph), 7.0–7.5 (6H, m, Ar-H, =CH).

c) 2-Benzyl-3-ethylacrylic acid

A solution of Example 49b (200 mg) in anisole (1 ml) and dichloromethane (1 ml) was treated with trifluoroacetic acid (2 ml). After 2 hours, the solvents were evaporated and the residue subjected to flash chromatography on silica gel (ethyl acetate-hexane-acetic acid) to give the title compound as a white solid (130 mg). δH (CDCl$_3$) 1.09 (3H, m, CH$_2$CH$_3$), 2.33 (2H, app.quint., CH$_2$CH$_3$), 3.70 (2H, s, CH$_2$Ph), 7.10 (1H, t, =CH), 7.18–7.33 (5H, m, Ar-H).

d) N-[2'-Benzyl-3'-ethylacryloyl]-D-phenylglycine methyl ester

A solution of Example 49c (100 mg) in dichloromethane (1 ml) was treated with oxalyl chloride (1 ml) and ¼ drop of DMF. The mixture was stirred for 1 hour then evaporated and coevaporated with toluene to give a clear oil. This was dissolved in dichloromethane (3 ml) and added dropwise to a stirred suspension of D-phenylglycine methyl ester hydrochloride (200 mg) and triethylamine (200 mg) in dichloromethane (5 ml). The mixture was stirred for 12 hours then partitioned between dichloromethane (3×25 ml) and 0.5M hydrochloric acid (25 ml). The combined organic phases were dried (MgSO$_4$), filtered and evaporated and the residue subjected to flash chromatography (ethyl acetate-hexane) to give the title compound as a gum in 85% yield. δH (CDCl$_3$) 1.08 (3H, m, CH$_2$CH$_3$), 2.30 (2H, app.quint., CH$_2$CH$_3$), 3.69 (3H, s, MeO), 3.72 (2H, d, CH$_2$Ph), 5.53 (1H, d, HCN), 6.61 (1H, t, =CH), 6.64 (1H, bd, NH), 7.10–7.33 (10H, m, Ar-H).

e) N-[3'-S-acetylmercapto-2'-benzylpentanoyl]-D-phenylglycine methyl ester

Example 49d (100 mg) was dissolved in thiolacetic acid (1 ml) and stood at RT for 2 days. The solvent was removed and the residue subjected to flash chromatography (ether-hexane) to afford the title compound as a gum, an approximately 1:1:4:4 mixture of diastereomers. δH (CDCl$_3$) 0.86–1.11 (3H, m), 1.23–1.90 (2H, m), 2.34, 2.38 (3H, 2s, MeCS), 2.55–2.97 (4H, m), 3.63, 3.65, 3.70, 3.73 (3H, 4s, MeO), 5.40–5.55 (1H, m, HCN), 6.16, 6.31, 6.47, 6.55 (1H, 4bd, NH), 6.95–7.33 (10H, m, Ar-H).

f) N-[2'-Benzyl-3'-mercaptopentanoyl]-D-phenylglycine

Prepared by the method of Example 46d, but using Example 49e (45 mg) as the starting material, the title compound was obtained as a clear oil, an approximately 1:1:4:4 mixture of diastereomers. νmax 3350, 2965, 1731, 1634, 1519 and 1177 cm$^{-1}$; m/z (ES+) 358 (M$^+$ 100%), 324 (45%).

Example 50

N-[2'-Benzyl-3'-mercaptobutanoyl]-D-phenylglycine a) 2-Benzyl-3-methylacrylic acid tertbutyl ester Prepared by the method of Example 49b but using acetaldehyde (88 mg) in place of propionaldehyde and using 700 mg of the phosphorane, the title compound was obtained as a clear oil (165 mg). δH (CDCl$_3$) 1.39 (9H, s, Me$_3$C), 1.86 (3H, d, =CCH$_3$), 3.65 (2H, s, CH$_2$Ph), 6.95 (1H, q, =CH) 7.13–7.37 (5H, m, Ar-H).

b) 2-Benzyl-3-methylacrylic acid

Prepared by the method of Example 49c but using Example 50a (205 mg), the title compound was obtained (155 mg) as a white solid after purification by crystallisation from ether-hexane. δH (CDCl$_3$) 1.94 (3H, d, =CCH$_3$), 3.71 (2H, s, CH$_2$Ph), 6.89 (1H, q, =CH) 7.17–7.36 (5H, m, Ar-H).

c) N-[2'-Benzyl-3'-methylacryloyl]-D-phenylglycine methyl ester

Prepared by the method of Example 49d but using Example 50b (140 mg), the title compound was obtained as a colourless oil in 89% yield. δH (CDCl$_3$) 1.89 (3H, d, =CCH$_3$), 3.68 (3H, s, MeO), 3.74 (2H, d, CH$_2$Ph), 5.54 (1H, d, HCN), 6.67 (1H, bd, NH), 6.74 (1H, q, =CH), 7.11–7.41 (10H, m, Ar-H).

d) N-[3'-S-acetylmercapto-2'-benzylbutanoyl]-D-phenylglycine methyl ester

Prepared by the method of Example 49e but using Example 50c (200 mg). After chromatography, four separated diastereoisomers of the title compound were obtained, in the ratio 40 mg:40 mg:20 mg:25 mg, in ascending order of polarity.

Least polar isomer: δH (CDCl$_3$) 1.25 (2H, d, =CMe), 2.31 (3H, s, MeCS), 2.64–3.09 (4H, m), 3.64 (3H, s, MeO), 5.42 (1H, d, HCN), 6.34 (1H, bd, NH), 7.12–7.33 (10H, m, Ar-H).

Second least polar: δH (CDCl$_3$) 1.41 (2H, d, =CMe), 2.36 (3H, s, MeCS), 2.54–3.09 (4H, m), 3.71 (3H, s, MeO), 5.45 (1H, d, HCN), 6.18 (1H, bd, NH), 6.95–7.33 (10H, m, Ar-H).

Third least polar: δH (CDCl$_3$) 1.31 (2H, d, =CMe), 2.38 (3H, s, MeCS), 2.55–3.20 (4H, m), 3.71 (3H, s, MeO), 5.43 (1H, d, HCN), 7.44 (1H, bd, NH), 7.20–7.33 (10H, m, Ar-H).

Most polar isomer: δH (CDCl$_3$) 1.47 (2H, d, =CMe), 2.42 (3H, s, MeCS), 2.90–3.30 (4H, m), 3.64 (3H, s, MeO), 5.40 (1H, d, HCN), 7.41 (1H, bd, NH), 7.00–7.33 (10H, m, Ar-H).

e) N-[2'-benzyl-3'-mercaptobutanoyl]-D-phenylglycine

Prepared by the method of Example 49f but using diastereomers of Example 50d (20 mg). The four diastereomeric isomers of were isolated separately.

Isomer A; From least polar isomer: δH (CDCl$_3$) 1.27 (2H, d, =CMe), 2.07 (1H, d, SH), 2.44–3.25 (4H, m), 5.42 (1H, d, HCN), 6.43 (1H, bd, NH), 7.00–7.40 (10H, m, Ar-H); m/z (ES+) 344 (MH$^+$ 100%), 310 (25%).

Isomer B; From second least polar: δH (CDCl$_3$) 1.41 (2H, d, =CMe), 2.07 (1H, d, SH), 2.40–3.25 (4H, m), 5.43 (1H, d, HCN), 6.36 (1H, bd, NH), 7.00–7.35 (10H, m, Ar-H) ; m/z (ES+) 344 (MH$^+$ 100%), 310 (85%).

Isomer C; From third least polar: δH (CDCl$_3$) 1.22 (2H, d, =CMe), 2.10 (1H, bs, SH), 2.35–3.45 (4H, m), 5.43 (1H, d, HCN), 7.44 (1H, bd, NH), 7.00–7.35 (10H, m, Ar-H); m/z (ES+) 344 (MH$^+$ 40%), 204 (100%).

Isomer D; From most polar isomer: δH (CDCl$_3$) 1.25 (2H, d, =CMe), 2.05 (1H, bs, SH), 2.35–3.45 (4H, m), 5.51 (1H, d, HCN), 7.41 (1H, bd, NH), 7.00–7.35 (10H, m, Ar-H); m/z (ES+) 344 (MH$^+$ 10%), 204 (100%).

Example 51

N-[2'-Benzyl-3'-mercapto-4'-methylpentanoyl]-D-phenylglycine

Prepared in an analogous manner to Example 49 but using isobuteraldehyde in place of propionaldehyde.

Example 52

N-[2'-Benzyl-2'-(1"-mercaptocyclopropyl)acetyl]-D-phenylglycine

Prepared in an analogous manner to Example 49 but using 1-trimethylsilyloxy-1-ethoxycyclopropane (Aldrich) and 10 mol % benzoic acid in place of propionaldehyde.

Example 53

N-[2'-(1"phenylethyl)-3'-mercapto-4'-methylpentanoyl]-D-phenylglycine a) 1-(2'-phenylethyl)-1-(tert-butyloxycarbonyl) methylenetriphenylphosphorane A solution of tertbutyloxycarbonylmethylenetriphenylphosphorane (1.85 g) in THF (10 ml) was treated with powdered sodium iodide (151 mg) and phenethyl bromide (0.75 ml). The mixture was heated to reflux under argon for four hours then cooled and sodium hydride (60% oil dispersion, 200 mg) introduced. The mixture was stirred for a further two days at RT then partitioned between saturated aqueous sodium hydrogen carbonate (100 ml) and dichloromethane (3×100 ml). The combined organic phase was dried (MgSO$_4$) filtered and evaporated. The residue was subjected to flash chromatography to give the title compound in 40% yield as a white solid. δH (CDCl$_3$) 0.96 (9H, s, CMe$_3$), 2.13 (2H, dt, PhCH$_2$), 2.51 (2H, bt, CH$_2$C=), 6.84–7.68 (20H, m, Ar-H).

b) N-[2'-(1"phenylethyl)-3'-mercapto-4'-methylpentanoyl]-D-phenylglycine

The title compound was prepared by the method of Example 51 but using Example 53a as the starting phosphorane.

Example 54

N-[2'-(1"-mercaptocyclopropyl)-2'-(1"-phenylethyl)acetyl]-D-phenylglycine

Prepared by the method of Example 53 but using 1-trimethylsilyloxy-1-ethoxycyclopropane (Aldrich) and 10 mol % benzoic acid in place of isobuteraldehyde

Example 55

N-[2'-Mercaptomethyl-4'-(4"-difluoromethoxphenyl)butanoyl)-D-phenylglycine

Prepared in an analogous manner to Example 46 but using 1-bromomethyl-4-difluoromethoxybenzene in place of methyl 4-bromomethylbenzoate.

Example 56

N-[2'-mercaptomethyl-3'-(3"-methyl-2',4",5"-tricarbonylimidazolidin-1"-yl)propanoyl]-D-phenylglycine a) 2-(3'-Methyl-2',4',5'-tricarbonyliinidazolidin-1'-yl)methylacrylic acid benzhydryl ester.

A solution of 2-bromomethylacrylic acid benzhydryl ester (661 mg) in acetonitrile (5 ml) was treated with 1-methyl-2,4,5-tricarbonylimidazolidine (300 mg) and caesium carbonate (700 mg). The resulting mixture was stirred for 3 clays at RT then filtered and passed though a silica gel plug, eluting with ether. The title compound was obtained as a white solid in 82% yield. δH (CDCl$_3$) 3.11 (3H, s, NMe), 4.55 (2H, s, NCH$_2$), 5.86, 6.57 (2H, 2s, =CH$_2$), 6.97 (1H, s, CHPh$_2$), 7.28–7.35 (10H, m, Ph-H).

b) N-[2'-mercaptomethyl-3'-(3"-methyl-2",4",5"-tricarbonylimidazolidin-1"-yl)propanoyl]-D-phenylglycine The title compound was prepared by the method described in Example 46 starting at part (c) but using Example 56a as the starting material.

Compounds of examples 2c, 3c and 10b are described in U.S. Pat. No. 4,513,009.

Compounds of examples 1b, 5d, 5f and 8c are described in DE3819539

BIOLOGICAL ACTIVITY

I$_{50}$ Screen

The inhibitory activity of the compounds of the invention was measured in 25 mM PIPES pH 7 buffer at 10 concentrations (1000, 333, 111, 37, 12.3, 4.1, 1.4, 0.46, 0.15 and 0.05 μM) at 37° C. using nitrocefin (91 μM final concentration) as the reporter substrate. The assays were performed with a 5 minute preincubation of enzyme and inhibitor and were conducted in the presence of added zinc sulphate (Zn$^{2+}$ 100 μM, final concentration). the methodology is described in detail in the following references: Payne et al (1991), *J. Antimicrob. Chemother.*, 28:255; Payne et al (1994), *Antimicrob. Agents and Chemother.*, 38:767.

Results

Compounds of the Examples exhibit I$_{50}$ values against *B. fragilis* CfiA metallo-β-lactamase of <1000 μM. The I$_{50}$ values for Examples 5d), 5e), 9e), 9i), 9k), 12, 13, 14, 15, 16, 17, 18, 19, 20, 22, 23, 24, 25, 27, 30, 31, 32, 37f), 38f), 39, 40f), 41, 42, 43, 44, 46 (Isomer A), 47 (Isomer B), 50 (Isomers B and C) and 55 were <1 μm.

All compounds of the above Examples exhibited significant inhibition of the *Stenotrophomonas maltophilia* L-1 (formerly *Xanthomonas maltophilia* L-1) and *Bacillus cereus* II metallo-β-lactamases, with I$_{50}$ values in the range 0.08–1000 μM.

Antibacterial activity of compounds of the invention in combination with the carbapenem antibiotic, meropenem, against the *Bacteroides fragis* 262 strain, which produces CfiA metallo-β-lactamase:

[MIC=minimum inhibitory concentration (μg/ml)]

Antibacterial activity of meropenem was potentiated as follows:

MIC (μg/ml) of meropenem alone: >128

| Inhibitor compound | MIC (μg/ml) of compound alone | MIC (μg/ml) of meropenem in the presence of 8 μg/ml of compound |
|---|---|---|
| E9k) | >128 | 32 |
| E12 | >128 | 32 |
| E13 | >128 | 32 |
| E14 | >128 | 64 |
| E19 | >128 | 4 |
| E22 | >128 | 64 |
| E23 | >128 | 128 |
| E24 | >128 | 16 |
| E27 | >128 | 32 |
| E31 | >128 | 32 |
| E32 | >128 | 128 |
| E37f) | >128 | 8 |
| E38f) | >128 | 16 |
| E43 | >128 | 32 |
| E49 | >128 | 16 |
| E50(all isomers) | >128 | 16 |
| E52 | >128 | 16 |
| E55 | >128 | 16 |

We claim:

1. A method of treatment of bacterial infections in humans or animals which comprises administering, in combination with a β-lactam antibiotic, a therapeutically effective amount of a compound of formula (I) or a pharmaceutically acceptable salt, solvate or in vivo hydrolysable ester thereof:

$$R_4S-C(R_5R_6)-CH(R_3)-CON(R_2)-CH(R_1)-CO_2R \quad (I)$$

wherein:

R is hydrogen, a salt forming cation or an in vivo hydrolysable ester-forming group;

R$_1$ is hydrogen, (C$_{1-6}$)alkyl optionally substituted by up to three halogen atoms or by a mercapto, (C$_{1-6}$)alkoxy, hydroxy, amino, nitro, carboxy, (C$_{1-6}$)alkylcarbonyloxy, (C$_{1-6}$)alkoxycarbonyl, formyl or ($C_{1-6}$) alkylcarbonyl group, ($C_{3-7}$)cycloalkyl, ($C_{3-7}$) cycloalkyl($C_{2-6}$)alkyl, ($C_{2-6}$)alkenyl, ($C_{2-6}$)alkynyl, aryl, aryl($C_{1-6}$)alkyl, heterocyclyl or heterocyclyl ($C_{1-6}$)alkyl;

$R_2$ is hydrogen, ($C_{1-6}$)alkyl or aryl($C_{1-6}$)alkyl;

$R_3$ is hydrogen, ($C_{1-6}$)alkyl optionally substituted by up to three halogen atoms, ($C_{3-7}$)cycloalkyl, fused aryl($C_{3-7}$) cycloalkyl, ($C_{3-7}$)cycloalkyl($C_{2-6}$)alkyl, ($C_{2-6}$)alkenyl, ($C_{2-6}$)alkynyl, aryl, aryl-($CHR_{10}$)$_m$—X—($CHR_{11}$)$_n$, heterocyclyl or heterocyclyl-($CHR_{10}$)$_m$—X—($CHR_{11}$)$_n$, where m is 0 to 3, n is 1 to 3 to 3, each $R_{10}$ and $R_{11}$ is independently hydrogen or ($C_{1-4}$)alkyl and X is O, $S(O)_x$ where x is 0–2, or a bond;

$R_4$ is hydrogen, or an in vivo hydrolysable acyl group; and $R_5$ and $R_6$ are independently hydrogen and ($C_{1-6}$)alkyl or together represent ($CH_2$)$_p$ where p is 2 to 5.

2. A method according to claim 1 wherein $R_1$ is aryl or heterocyclyl and $R_3$ is aryl-($CHR_{10}$)$_m$—X—($CHR_{11}$)$_n$.

3. A method according to claim 1 where $R_5$ and $R_6$ are other than hydrogen.

4. A method according to claim 1 wherein the stereochemistry at the carbon marked * is D-.

5. A method according to claim 1 wherein $R_1$ is selected from the group consisting of methyl, isobutyl, carboxymethyl, mercaptomethyl, 1-hydroxyethyl, optionally substituted benzyl, phenyl optionally substituted with up to five, preferably up to three, groups selected from halogen, mercapto, ($C_{1-6}$) alkyl optionally substituted by 1–3 halo, phenyl, ($C_{1-6}$) alkoxy optionally substituted by 1–3 halo, hydroxy($C_{1-6}$)alkyl, mercapto($C_{1-6}$)alkyl, hydroxy, amino, nitro, carboxy, ($C_{1-6}$) alkylcarbonyloxy, ($C_{1-6}$)alkoxycarbonyl, formyl or ($C_{1-6}$) alkylcarbonyl groups, indolyl, thienyl, isoimidazolyl, thiazolyl, furyl and benzothienyl.

6. A method according to claim 5 wherein $R_1$ is unsubstituted phenyl.

7. A method according to claim 1 wherein $R_2$ is selected from the group consisting of hydrogen, methyl and benzyl.

8. A method according to claim 7 wherein $R_2$ is hydrogen.

9. A method according to claim 1 wherein $R_3$ is aryl-($CH_2$)$_m$—X—($CH_2$)$_n$.

10. A method according to claim 1 wherein $R_4$ is hydrogen.

11. A method according to claim 1 wherein $R_5$ and $R_6$ are independently hydrogen or methyl.

12. A method according to claim 1 wherein X is O, S or a bond and $R_{10}$ and $R_{11}$ are each hydrogen.

13. A method according to claim 1 wherein the stereochemistry at the carbon atom marked * is D- and the stereochemistry at the carbon atom marked (+) is S.

14. A method according to claim 1 wherein the compound of formula (I) is selected from the group consisting of:

N-[2'-benzyl-3'-mercaptopropionyl]phenylalanine;
N-[2'-benzyl-3'-mercaptopropionyl]leucine;
N-[2'-benzyl-3'-mercaptopropionyl]alanine;
N-[2'-benzyl-3'-mercaptopropionyl]tryptophan;
N-[2'-benzyl-3'-mercaptopropionyl]tyrosine;
N-[(R)-2'-benzyl-3'-mercaptopropionyl]glycine; and
N-[(S)-2'-benzyl-3'-mercaptopropionyl]glycine;

or a pharmaceutically acceptable salt, solvate or in vivo hydrolysable ester thereof.

15. A method according to claim 1 wherein the compound is selected from the group consisting of N-[2'-benzyl-3'-mercaptopropionyl]aspartic acid;
N-[2'-benzyl-3'-mercaptopropionyl]-D-tryptophan;
N-[2'-benzyl-3'-mercaptopropionyl]threonine;
N-[2'-benzyl-3'-mercaptopropionyl]cysteine;
N-[2'-benzyl-3'-mercaptopropionyl]phenylglycine;
N-[2'-benzyl-3'-mercaptopropionyl]-D-phenylglycine;
[2'S]-N-[2'-benzyl-3'-mercaptopropionyl]-D-phenylglycine;
[2'R]-N-[2'-benzyl-3'-mercaptopropionyl]-D-phenylglycine;
N-[2'-benzyl-3'-mercaptopropionyl]-3-hydroxyphenylglycine;
N-[2'-benzyl-3'-mercaptopropionyl]-4-hydroxy-D-phenylglycine;
N-[2'-benzyl-3'-mercaptopropionyl]-4-methoxyphenylglycine;
N-[2'-benzyl-3'-mercaptopropionyl]-4-hydroxy-3-nitrophenylglycine;
N-[2'-benzyl-3'-mercaptopropionyl]-3,4-dihydroxy-D-phenylglycine;
N-[2'-benzyl-3'-mercaptopropionyl]-4-fluoro-D-phenylglycine;
N-[2'-benzyl-3'-mercaptopropionyl]-3-fluorophenylglycine;
N-[2'-benzyl-3'-mercaptopropionyl]-3-nitro-D-phenylglycine;
N-[2'-benzyl-3'-mercaptopropionyl]-2-fluorophenylglycine;
N-[2'-benzyl-3'-mercaptopropionyl]-2-thienylglycine;
N-[2'-benzyl-3'-mercaptopropionyl]-N-benzyl-phenylglycine;
N-[2'-methyl-3'-mercaptopropionyl]-D-phenylglycine;
N-[4-methyl-2-mercaptomethylpentanoyl]-D-phenylglycine;
N-[2'-benzyl-3'-mercaptopropionyl]-4-methylphenylglycine;
N-[2'-benzyl-3'-mercaptopropionyl]-4-[1-methylisoimidazolyl]glycine;
N-[2'-benzyl-3'-mercaptopropionyl]-3-methylphenylglycine (Isomer A and B);
N-[2'-isobutyl-3'-mercaptobutanoyl]-D phenylglycine;
N-[2'-benzyl-3'-mercaptopropionyl]-N-methyl-phenylglycine (Isomers A and B);
N-[2'-benzyl-3'-mercaptopropionyl]-2-(4"-thiazolyl) glycine;
N-[2'-benzyl-3'-mercaptopropionyl]-2-(2"-furanyl) glycine;
N-[2'-benzyl-3'-mercaptopropionyl]-2-(2"-benzothienyl) glycine;
N-[2'-benzyl-3'-mercaptopropionyl]-2-(3"-furanyl) glycine;
N-[2'-benzyl-3'-mercaptopropionyl]-2-(1"-naphthyl) glycine;
N-[2'-benzyl-3'-mercaptopropionyl]-2-(4"-biphenyl) glycine;
N-[2'-benzyl-3'-mercaptopropionyl]-2-(4"-isopropylphenyl)-glycine;
N-[2'-benzyl-3'-mercaptopropionyl]-2-(3"-benzothienyl) glycine;
N-[(R)-2'-mercaptomethyl-4'-phenylbutanoyl]-D-phenylglycine;
N-[(S)-2'-mercaptomethyl-4'-phenylbutanoyl]-D-phenylglycine;

N-[(R)-2'-mercaptomethyl-5'-phenylpentanoyl]-D-phenylglycine;

N-[(S)-2'-mercaptomethyl-5'-phenylpentanoyl]-D-phenylglycine;

N-(2'-mercaptomethyl-6'-phenylhexanoyl)-D-phenylglycine;

N-[(R)-2'-mercaptomethyl-7'-phenylheptanoyl]-D-phenylglycine;

N-[(S)-2'-mercaptomethyl-7'-phenylheptanoyl]-D-phenylglycine;

N-[2'-(indan-1-yl)-3'-mercaptopropanoyl]-D-phenylglycine;

N-[2'- and N-[(S)-2'-ercaptomethyl-4'-phenoxybutanoyl]-D-phenylglycine;

N-[2'-benzyl-3'-mercaptopropionyl]-2-(3"-thienyl)glycine;

N-[2'-(1"-mercaptoethyl)-4'-phenylbutanoyl]-D-phenylglycine;

N-[3'-(3",4"-dihydroxyphenyl)-(R,S)-2'-mercaptomethyl-propanoyl)-D-phenylglycine;

N-[2'-mercaptomethyl-4'-(4"-hydroxycarbonyl)phenylbutanoyl]-D-phenylglycine;

N-[2'-mercaptomethyl-4'-(2"-trifluoromethyl-6"-quinolin-6-yl)butanoyl]-D-phenylglycine;

N-[3-mercaptobutanoyl]-D-phenylglycine;

N-[2-benzyl-3-mercaptopentanoyl]-D-phenylglycine;

N-[2'-benzyl-3'-mercaptobutanoyl]-D-phenylglycine;

N-[2'-benzyl-3'-mercapto-4'-methylpentanoyl]-D-phenylglycine;

N-[2'-benzyl-2'-(1"-mercaptocyclopropyl)acetyl]-D-phenylglycine;

N-[2'-(1"phenylethyl)-3'-mercapto-4'-methylpentanoyl]-D-phenylglycine;

N-[2'-(1"-mercaptocyclopropyl)-2'-(1"-phenylethyl)acetyl]-D-phenylglycine;

N-[2'-mercaptomethyl-4'-(4"-difluoromethoxphenyl)butanoyl)-D-phenylglycine; and

N-[2'-mercaptomethyl-3'-(3"-methyl-2",4",5"-tricarbonylimidazolidin-1-yl)propanoyl]-D-phenylglycine or a pharmaceutically acceptable salt, solvate or in vivo hydrolysable ester thereof.

16. A pharmaceutical composition for treating bacterial infections in humans or animals comprising a compound of formula (I)

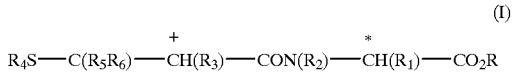

(I)

wherein:

R is hydrogen, a salt forming cation or an in vivo hydrolysable ester-forming group;

$R_1$ is hydrogen, $(C_{1-6})$alkyl optionally substituted by up to three halogen atoms or by a mercapto, $(C_{1-6})$alkoxy, hydroxy, amino, nitro, carboxy, $(C_{1-6})$alkylcarbonyloxy, $(C_{1-6})$alkoxycarbonyl, formyl or $(C_{1-6})$ alkylcarbonyl group, $(C_{3-7})$cycloalkyl, $(C_{3-7})$cycloalkyl$(C_{2-6})$alkyl, $(C_{2-6})$alkenyl, $(C_{2-6})$alkynyl, aryl, aryl$(C_{1-6})$alkyl, heterocyclyl or heterocyclyl $(C_{1-6})$alkyl;

$R_2$ is hydrogen, $(C_{1-6})$alkyl or aryl$(C_{1-6})$alkyl;

$R_3$ is hydrogen, $(C_{1-6})$alkyl optionally substituted by up to three halogen atoms, $(C_{3-7})$cycloalkyl, fused aryl$(C_{3-7})$cycloalkyl, $(C_{3-7})$cycloalkyl$(C_{2-6})$alkyl, $(C_{2-6})$alkenyl, $(C_{2-6})$alkynyl, aryl, aryl-$(CHR_{10})_m$—X—$(CHR_{11})_n$, heterocyclyl or heterocyclyl-$(CHR_{10})_m$—X—$(CHR_{11})_n$, where m is 0 to 3, n is 1 to 3 to 3, each $R_{10}$ and $R_{11}$ is independently hydrogen or $(C_{1-4})$alkyl and X is O, S(O)$_x$ where x is 0–2, or a bond;

$R_4$ is hydrogen, or an in vivo hydrolysable acyl group; and $R_5$ and $R_6$ are independently hydrogen and $(C_{1-6})$alkyl or together represent $(CH_2)_p$ where p is 2 to 5 and a wherein the β-lactam antibiotic is a carbapenem selected from imipenem, meropenem, biapenem, BMS181139 ([4R-[4alpha,5beta,6beta(R*)]]-4-[2-[(aminoiminomethyl)amino]ethyl]-3-[(2-cyanoethyl)thio]-6-(1-hydroxyethyl)-7-oxo-1-azabicyclo[3,2,0]hept-2-ene-2-carboxylic acid), BO2727 ([4R-3[3S*,5S*(R*)],4alpha,5beta,6beta(R*)]]-6-(1-hydroxyethyl)-3-[[5-[1-hydroxy-3-(methylamino)propyl]-3-pyrrolidinyl]thio]-4-methyl-7-oxo-1-azabicyclo[3,2,0] hept-2-ene-2-carboxylic acid monohydrochloride), ER35786 ((1R, 5S, 6S)-6-[1(R)-Hydroxymethyl]-2-[2(S)-[1(R)-hydroxy-1-[pyrrolidin-3(R)-yl] methyl]pyrrolidin-4(S)-ylsulfanyl]-1-methyl-1-carba-2-penem-3-carboxylic acid hydrochloride) and S4661 ((1R,5S,6S)-2-[(3S,5S)-5-(sulfamoylaminomethyl) pyrrolidin-3-yl]thio-6-[(1R)-1-hydroxyethyl]-1-methylcarbapen-2-em-3-carboxylic acid).

17. A composition according to claim 16 wherein, for Formula (I), $R_1$ is aryl or heterocyclyl and $R_3$ is aryl-$(CHR_{10})_m$—X—$(CHR_{11})_n$.

18. A composition according to claim 16 wherein, for Formula (I), $R_5$ and $R_6$ are other than hydrogen.

19. A composition according to claim 16 wherein, for Formula (I), wherein the stereochemistry at the carbon marked * is D-.

20. A composition according to claim 16 wherein, for Formula (I), $R_1$ is selected from the group consisting of methyl, isobutyl, carboxymethyl, mercaptomethyl, 1-hydroxyethyl, optionally substituted benzyl, phenyl optionally substituted with up to five, preferably up to three, groups selected from halogen, mercapto, $(C_{1-6})$ alkyl optionally substituted by 1–3 halo, phenyl, $(C_{1-6})$ alkoxy optionally substituted by 1–3 halo, hydroxy$(C_{1-6})$alkyl, mercapto $(C_{1-6})$alkyl, hydroxy, amino, nitro, carboxy, $(C_{1-6})$ alkylcarbonyloxy, $(C_{1-6})$alkoxycarbonyl, formyl or $(C_{1-6})$ alkylcarbonyl groups, indolyl, thienyl, isoimidazolyl, thiazolyl, furyl and benzothienyl.

21. A composition according to claim 16 wherein, for Formula (I), $R_1$ is unsubstituted phenyl.

22. A composition according to claim 16 wherein, for Formula (I), $R_2$ is hydrogen, methyl or benzyl, $R_3$ is aryl-$(CH_2)_m$—X—$(CH_2)_n$, $R_4$ is hydrogen, $R_5$ and $R_6$ are independently hydrogen or methyl, X is O, S or a bond, $R_{10}$ and $R_{11}$ are each hydrogen, the stereochemistry at the carbon atom marked * is D-, and the stereochemistry at the carbon atom marked (+) is S.

23. A composition according to claim 16 wherein the compound of Formula (I) is

N-[2'-benzyl-3'-mercaptopropionyl]phenylalanine;

N-[2'-benzyl-3'-mercaptopropionyl]leucine;

N-[2'-benzyl-3'-mercaptopropionyl]alanine;

N-[2'-benzyl-3'-mercaptopropionyl]tryptophan;

N-[2'-benzyl-3'-mercaptopropionyl]tyrosine;

N-[(R)-2'-benzyl-3'-mercaptopropionyl]glycine;

N-[(S)-2'-benzyl-3'-mercaptopropionyl]glycine;
N-[2'-benzyl-3'-mercaptopropionyl]aspartic acid;
N-[2'-benzyl-3'-mercaptopropionyl]-D-tryptophan;
N-[2'-benzyl-3'-mercaptopropionyl]threonine;
N-[2'-benzyl-3'-mercaptopropionyl]cysteine;
N-[2'-benzyl-3'-mercaptopropionyl]phenylglycine;
N-[2'-benzyl-3'-mercaptopropionyl]-D-phenylglycine;
[2'S]-N-[2'-benzyl-3'-mercaptopropionyl]-D-phenylglycine;
[2'R]-N-2'-benzyl-3'-mercaptopropionyl]-D-phenylglycine;
N-[2'-benzyl-3'-mercaptopropionyl]-3-hydroxyphenylglycine;
N-[2'-benzyl-3'-mercaptopropionyl]-4-hydroxy-D-phenylglycine;
N-[2'-benzyl-3'-mercaptopropionyl]-4-methoxyphenylglycine;
N-[2'-benzyl-3'-mercaptopropionyl]-4-hydroxy-3-nitrophenylglycine;
N-[2'-benzyl-3'-mercaptopropionyl]-3,4-dihydroxy-D-phenylglycine;
N-[2'-benzyl-3'-mercaptopropionyl]-4-fluoro-D-phenylglycine;
N-[2'-benzyl-3'-mercaptopropionyl]-3-fluorophenylglycine;
N-[2'-benzyl-3'-mercaptopropionyl]-3-nitro-D-phenylglycine;
N-[2'-benzyl-3'-mercaptopropionyl]-2-fluorophenylglycine;
N-[2'-benzyl-3'-mercaptopropionyl]-2-thienylglycine;
N-[2'-benzyl-3'-mercaptopropionyl]-N-benzyl-phenylglycine;
N-[2'-methyl-3'-mercaptopropionyl]-D-phenylglycine;
N-[4-methyl-2-mercaptomethylpentanoyl]-D-phenylglycine;
N-[2'-benzyl-3'-mercaptopropionyl]-4-methylphenylglycine;
N-[2'-benzyl-3'-mercaptopropionyl]-4-[1-methylisoimidazolyl]glycine;
N-[2'-benzyl-3'-mercaptopropionyl]-3-methylphenylglycine (Isomer A and B);
N-[2'-isobutyl-3'-mercaptobutanoyl]-D phenylglycine;
N-[2'-benzyl-3'-mercaptopropionyl]-N-methyl-phenylglycine (Isomers A and B);
N-[2'-benzyl-3'-mercaptopropionyl]-2-(4"-thiazolyl) glycine;
N-[2'-benzyl-3'-mercaptopropionyl]-2-(2"-furanyl) glycine;
N-[2'-benzyl-3'-mercaptopropionyl]-2-(2"-benzothienyl) glycine;
N-[2'-benzyl-3'-mercaptopropionyl]-2-(3"-furanyl) glycine;
N-[2'-benzyl-3'-mercaptopropionyl]-2-(1"-naphthyl) glycine;
N-[2'-benzyl-3'-mercaptopropionyl]-2-(4"-biphenyl) glycine;
N-[2'-benzyl-3'-mercaptopropionyl]-2-(4"-isopropylphenyl)-glycine;
N-[2'-benzyl-3'-mercaptopropionyl]-2-(3"-benzothienyl) glycine;
N-[(R)-2'-mercaptomethyl-4'-phenylbutanoyl]-D-phenylglycine;
N-[(S)-2'-mercaptomethyl-4'-phenylbutanoyl]-D-phenylglycine;
N-[(R)-2'-mercaptomethyl-5'-phenylpentanoyl]-D-phenylglycine;
N-[(S)-2'-mercaptomethyl-5'-phenylpentanoyl]-D-phenylglycine;
N-(2'-mercaptomethyl-6'-phenylhexanoyl)-D-phenylglycine;
N-[(R)-2'-mercaptomethyl-7'-phenylheptanoyl]-D-phenylglycine;
N-[(S)-2'-mercaptomethyl-7'-phenylheptanoyl]-D-phenylglycine;
N-[2'-(indan-1-yl)-3'-mercaptopropanoyl]-D-phenylglycine;
N-[2'- and N-[(S)-2'-ercaptomethyl-4'-phenoxybutanoyl]-D-phenylglycine;
N-[2'-benzyl-3'-mercaptopropionyl]-2-(3"-thienyl) glycine;
N-[2'-(1"-mercaptoethyl)-4'-phenylbutanoyl]-D-phenylglycine;
N-[3'-(3",4"-dihydroxyphenyl)-(R,S)-2'-mercaptomethyl-propanoyl)-D-phenylglycine;
N-[2'-mercaptomethyl-4'-(4"-hydroxycarbonyl) phenylbutanoyl]-D-phenylglycine;
N-[2'-mercaptomethyl-4'-(2"-trifluoromethyl-6"-quinolin-6-yl)butanoyl)-D-phenylglycine;
N-[3-mercaptobutanoyl]-D-phenylglycine;
N-[2-benzyl-3-mercaptopentanoyl]-D-phenylglycine;
N-[2'-benzyl-3'-mercaptobutanoyl]-D-phenylglycine;
N-[2'-benzyl-3'-mercapto-4'-methylpentanoyl]-D-phenylglycine;
N-[2'-benzyl-2'-(1"-mercaptocyclopropyl)acetyl]-D-phenylglycine;
N-[2'-(1"phenylethyl)-3'-mercapto-4'-methylpentanoyl]-D-phenylglycine;
N-[2'-(1"-mercaptocyclopropyl)-2'-(1"-phenylethyl) acetyl]-D-phenylglycine;
N-[2'-mercaptomethyl-4'-(4"-difluoromethoxphenyl) butanoyl)-D-phenylglycine; or
N-[2'-mercaptomethyl-3'-(3"-methyl-2",4",5"-tricarbonylimidazolidin-1"-yl)propanoyl]-D-phenylglycine; or a pharmaceutically acceptable salt, solvate or in vivo hydrolysable ester thereof.

* * * * *